US006511994B2

(12) United States Patent
Kim et al.

(10) Patent No.: US 6,511,994 B2
(45) Date of Patent: Jan. 28, 2003

(54) MODULATORS OF CCR5 CHEMOKINE RECEPTOR ACTIVITY

(75) Inventors: Ronald M. Kim, Hoboken, NJ (US); Jiang Chang, Westfield, NJ (US); Kevin T. Chapman, Scotch Plains, NJ (US); Sander G. Mills, Scotch Plains, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/973,920

(22) Filed: Oct. 10, 2001

(65) Prior Publication Data

US 2002/0193407 A1 Dec. 19, 2002

Related U.S. Application Data

(60) Provisional application No. 60/239,285, filed on Oct. 11, 2000.

(51) Int. Cl.[7] ................. A61K 31/445; C07D 211/08; C07D 211/06
(52) U.S. Cl. .............. 514/319; 514/320; 514/326; 546/192; 546/195; 546/196; 546/205; 546/207
(58) Field of Search ................. 514/320, 319, 514/326; 546/195, 196, 205, 207, 192

(56) References Cited

U.S. PATENT DOCUMENTS

| | | | |
|---|---|---|---|
| 5,468,469 A | 11/1995 | Aszalos et al. |
| 6,136,827 A | 10/2000 | Caldwell et al. |
| 6,140,349 A | 10/2000 | Caldwell et al. |
| 6,166,037 A | 12/2000 | Budhu et al. |
| 6,248,755 B1 | 6/2001 | Chapman et al. |
| 6,265,434 B1 | 7/2001 | Caldwell et al. |

FOREIGN PATENT DOCUMENTS

| | | | |
|---|---|---|---|
| EP | 1013276 | * | 6/2000 |
| WO | WO 00/38680 | | 7/2000 |
| WO | WO 00/39125 | | 7/2000 |
| WO | WO 00/59497 | | 10/2000 |
| WO | WO 00/59498 | | 10/2000 |

OTHER PUBLICATIONS

Ko, CA 133:43445, abstract of WO 200035454, Jun. 2000.*
Ko, CA 133:43444, abstract of WO 200035453, Jun. 2000.*
Carceller, CA 124:176036, abstract of J Med Chem, 1996, 39(2), 487–493.*
Edmonds–Alt, CA 117:26590, abstract of EP 474561, Mar. 1992.*
T. J. Schall, "Biology of the Rantes/sis Cytokine Family", Cytokine, vol. 3, No. 3, May 1991, pp. 165–183.
P. M. Murphy, "The Molecular Biology of Leukocyte Chenoattractant Receptors", Annual Review of Immunology, vol. 12, 1994, pp. 593–633.
H. Deng et al., "Identification of a major co–receptor for primary isolates of HIV–1", Nature, vol. 381, Jun. 1996, pp. 661–666.

R. Horuk, "Molecular properties of the chemokine receptor family", Trends Pharm. Science, vol. 15, 1994, pp. 159–165.
A. Ben–Baruch et al., "Monocyte Chemotactic Protein–3 (MCP3) Interacts with Multiple Leukocyte Receptors", J. Biol. Chem., vol. 270, No. 38, Sep. 1995, pp. 22123–22128.
K. Neote et al., "Molecular Cloning, Functional Expression, and Signaling Characteristics of a C–C Chemokine Receptor", Cell, vol. 72, Feb. 1993, pp. 415–425.
C. Combadiere et al., "Cloning and Functional Expression of a Human Eosinophil CC Chemokine Receptor", J. Biol. Chem., vol. 270, No. 27, Jul. 1995, pp. 16491–16494.
C. A. Power et al., "Molecular Cloning and Functional Expression of a Novel CC Chemokine Receptor cDNA from a Human Basophilic Line", J. Biol. Chem., vol. 270, No. 33, Aug. 1995, pp. 19495–19500.
M. Samson et al., "Molecular Cloning and Functional Expression of a New Human CC–Chemokine Receptor Gene", Biochemistry, vol. 35, 1996, pp. 3362–3367.
A. Chaudhuri et al., "Expression of the Duffy Antigen in K562 Cells,", J. Biol. Chem., vol. 269, No. 11, Mar. 1994, pp. 7835–7838.
H. Kita et al., "Chemokines Active on Eosinophils: Potential Roles in Allergic Inflammation", J. Exp. Med., vol. 183, Jun. 1996, pp. 2421–2426.
D. Smith et al., "Blocking of HIV–1 Infectivity by a Soluable, Secreted Form of the CD4 Antigen", Science, vol. 238, 1987, pp. 1704–1707.
J. A. Levy, "Infection by Human Immunodeficiency Virus— DC4 is not Enough", N. Eng. J. Med., vol. 335, No. 20, Nov. 1996), pp. 1528–1530.
T. Dragic et al., "HIV–1 entry into CD4+ cells is mediated by the chemokine receptor CC–CKR5", Nature, vol. 381, Jun. 1996, pp. 667–673.

(List continued on next page.)

*Primary Examiner*—D. Margaret Seaman
(74) *Attorney, Agent, or Firm*—Kenneth R. Walton; Melvin Winokur

(57) ABSTRACT

Compounds of Formula I:

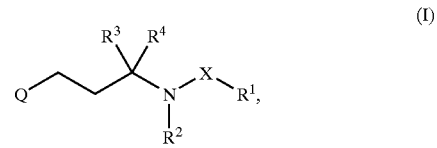

(wherein $R^1$, $R^2$, $R^3$, $R^4$, Q, and X are defined herein) are described. The compounds are modulators of CCR5 chemokine receptor activity. The compounds are useful, for example, in the prevention or treatment of infection by HIV and the treatment of AIDS, as compounds or pharmaceutically acceptable salts, or as ingredients in pharmaceutical compositions, optionally in combination with other antivirals, immunomodulators, antibiotics or vaccines. Methods of treating AIDS and methods of preventing or treating infection by HIV are also described.

24 Claims, No Drawings

OTHER PUBLICATIONS

L. Wu et al., "CD4–induced interaction of primary HIV–1 gp120 glycoproteins with the chemokine receptor CCR–5", Nature, vol. 384, Nov. 1996, pp. 179–183.

A. Trkola et al., "CD4–dependent, antibody–sensitive interactions between HIV–1 and its co–receptor CCR–5", Nature, vol. 384, Nov. 1996, pp. 184–187.

M. Samson et al., "Resistence to HIV–1 infection in caucasian individuals bearing mutant alleles of the CCR–5 cehmokine receptor gene", Nature, vol. 382, Aug. 1996, pp. 722–725.

C. M. Hill et al., "Natural resistance to HIV?", Nature, vol. 382, Aug. 1996, pp. 668–669.

Y. Huang et al., "The Role of a mutant CCR5 allele in HIV–1 transmission and disease progression", Nature Medicine, vol. 2, No. 11, Nov. 1996, pp. 1240–1243.

L. Zhang et al., "HIV–1 subtype and second–receptor use", Nature, vol. 383, Oct. 1996, p. 768.

Armour, et al.; Chemical Abstracts No. 133.58719, Abstract EP 1013276, 2000.

* cited by examiner

MODULATORS OF CCR5 CHEMOKINE RECEPTOR ACTIVITY

This application claims the benefit of U.S. Provisional Application No. 60/239,285, filed Oct. 11, 2000, the disclosure of which is hereby incorporated by reference in its entirety.

BACKGROUND OF THE INVENTION

Chemokines are chemotactic cytokines that are released by a wide variety of cells to attract macrophages, T cells, eosinophils, basophils and neutrophils to sites of inflammation (reviewed in Schall, *Cytokine*, 3, 165–183 (1991) and Murphy, *Rev. Immun.*, 12, 593–633 (1994)). There are two classes of chemokines, C-X-C (α) and C-C (β), depending on whether the first two cysteines are separated by a single amino acid (C-X-C) or are adjacent (C-C). The α-chemokines, such as interleukin-8 (IL-8), neutrophil-activating protein-2 (NAP-2) and melanoma growth stimulatory activity protein (MGSA) are chemotactic primarily for neutrophils, whereas β-chemokines, such as RANTES, MIP-1α, MIP-1β, monocyte chemotactic protein-1 (MCP-1), MCP-2, MCP-3 and eotaxin are chemotactic for macrophages, T-cells, eosinophils and basophils (Deng, et al., *Nature*, 381, 661–666 (1996)).

The chemokines bind specific cell-surface receptors belonging to the family of G-protein-coupled seven-transmembrane-domain proteins (reviewed in Horuk, *Trends Pharm. Sci.*, 15, 159–165 (1994)) which are termed "chemokine receptors." On binding their cognate ligands, chemokine receptors transduce an intracellular signal though the associated trimeric G protein, resulting in a rapid increase in intracellular calcium concentration. There are at least sixteen human chemokine receptors that bind or respond to β-chemokines with the following characteristic pattern: CCR1 (or "CKR-1" or "CC-CKR-1")[MIP-1α, MIP-1β, MCP-3, RANTES] (Ben-Barruch, et al., *J. Biol. Chem.*, 270, 22123–22128 (1995); Beote, et al, *Cell*, 72, 415–425 (1993)); CCR2A and CCR2B (or "CKR-2A"/ "CKR-2A" or "CC-CKR-2A"/"CC-CKR-2A")[MCP-1, MCP-3, MCP-4]; CCR3 (or "CKR-3" or "CC-CKR-3") [eotaxin, RANTES, MCP-3] (Combadiere, et al., *J. Biol. Chem.*, 270, 16491–16494 (1995); CCR4 (or "CKR-4" or "CC-CKR4")[MIP-1α, RANTES, MCP-1] (Power, et al., *J. Biol. Chem.*, 270, 19495–19500 (1995)); CCR5 (or "CKR-5" or "CC-CKR-5")[MIP-1α, RANTES, MIP-1β] (Sanson, et al., *Biochemistry*, 35, 3362–3367 (1996)); and the Duffy blood-group antigen [RANTES, MCP-1] (Chaudhun, et al., *J. Biol. Chem.*, 269, 7835–7838 (1994)). The β-chemokines include eotaxin, MIP ("macrophage inflammatory protein"), MCP ("monocyte chemoattractant protein") and RANTES ("regulation-upon-activation, normal T expressed and secreted").

Chemokine receptors, such as CCR1, CCR2, CCR2A, CCR2B, CCR3, CCR4, CCR5, CXCR-3, CXCR-4, have been implicated as being important mediators of inflammatory and immunoregulatory disorders and diseases, including asthma, rhinitis and allergic diseases, as well as autoimmune pathologies such as rheumatoid arthritis and atherosclerosis. A review of the role of chemokines in allergic inflammation is provided by Kita, H., et al., *J. Exp. Med.* 183, 2421–2426 (1996). Accordingly, agents which modulate chemokine receptors would be useful in such disorders and diseases. Compounds which modulate chemokine receptors would be especially useful in the treatment and prevention of atopic conditions including allergic rhinitis, dermatitis, conjunctivitis, and particularly bronchial asthma.

A retrovirus designated human immunodeficiency virus (HIV-1) is the etiological agent of the complex disease that includes progressive destruction of the immune system (acquired immune deficiency syndrome; AIDS) and degeneration of the central and peripheral nervous system. This virus was previously known as LAV, HTLV-III, or ARV.

Certain compounds have been demonstrated to inhibit the replication of HIV, including soluble CD4 protein and synthetic derivatives (Smith, et al., Science, 238, 1704–1707 (1987)), dextran sulfate, the dyes Direct Yellow 50, Evans Blue, and certain azo dyes (U.S. Pat. No. 5,468,469). Some of these antiviral agents have been shown to act by blocking the binding of gp120, the coat protein of HIV, to its target, the CD4 glycoprotein of the cell.

Entry of HIV-1 into a target cell requires cell-surface CD4 and additional host cell cofactors. Fusin has been identified as a cofactor required for infection with virus adapted for growth in transformed T-cells, however, fusin does not promote entry of macrophagetropic viruses which are believed to be the key pathogenic strains of HIV in vivo. It has recently been recognized that for efficient entry into target cells, human immunodeficiency viruses require a chemokine receptors, most probably CCR5 or CXCR-4, as well as the primary receptor CD4 (Levy, *N. Engl. J. Med.*, 335(20), 1528–1530 (Nov. 14, 1996). The principal cofactor for entry mediated by the envelope glycoproteins of primary macrophage-trophic strains of HIV-1 is CCR5, a receptor for the β-chemokines RANTES, MIP-1α and MIP-1β (Deng, et al., *Nature*, 381, 661–666 (1996)). HIV attaches to the CD4 molecule on cells through a region of its envelope protein, gp120. It is believed that the CD-4 binding site on the gp120 of HIV interacts with the CD4 molecule on the cell surface, and undergoes conformational changes which allow it to bind to another cell-surface receptor, such as CCR5 and/or CXCR-4. This brings the viral envelope closer to the cell surface and allows interaction between gp41 on the viral envelope and a fusion domain on the cell surface, fusion with the cell membrane, and entry of the viral core into the cell. It has been shown that β-chemokine ligands prevent HIV-1 from fusing with the cell (Dragic, et al., *Nature*, 381, 667–673 (1996)). It has further been demonstrated that a complex of gp120 and soluble CD4 interacts specifically with CCR5 and inhibits the binding of the natural CCR5 ligands MIP-1α and MIP-1β (Wu, et al., *Nature*, 384, 179–183 (1996); Trkola, et al., *Nature*, 384, 184–187 (1996)).

Humans who are homozygous for mutant CCR5 receptors which are not expressed on the cell surface appear to be unusually resistant to HIV-1 infection and are not immunocompromised by the presence of this genetic variant (*Nature*, 382, 722–725 (1996)). Absence of CCR5 appears to confer substantial protection from HIV-1 infection (*Nature*, 382, 668–669 (1996)). Other chemokine receptors may be used by some strains of HIV-1 or may be favored by non-sexual routes of transmission. Although most HIV-1 isolates studied to date utilize CCR5 or fusin, some can use both as well as the related CCR2B and CCR3 as co-receptors (*Nature Medicine*, 2(11), 1240–1243 (1996)). Nevertheless, drugs targeting chemokine receptors may not be unduly compromised by the genetic diversity of HIV-1 (Zhang, et al., *Nature*, 383, 768 (1996)). Accordingly, an agent which could block chemokine receptors in humans who possess normal chemokine receptors should prevent infection in healthy individuals and slow or halt viral progression in infected patients. By focusing on the host's cellular immune response to HIV infection, better therapies towards all subtypes of HIV may be provided. These results indicate that inhibition of chemokine receptors presents a viable method for the prevention or treatment of infection by HIV and the prevention or treatment of AIDS.

The peptides eotaxin, RANTES, MIP-1α, MIP-1β, MCP-1, and MCP-3 are known to bind to chemokine receptors. As noted above, the inhibitors of HIV-1 replication present in supernatants of CD8+ T cells have been characterized as the β-chemokines RANTES, MIP-1α and MIP-1β.

The following references are of interest as background:

WO 00/38680 discloses certain azabicycloalkanes to be useful as CCR5 modulators.

WO 00/39125 discloses certain piperidines to be useful as CCR5 modulators.

SUMMARY OF THE INVENTION

The present invention is directed to compounds which inhibit the entry of human immunodeficiency virus (HIV) into target cells and are of value in the prevention of infection by HIV, the treatment of infection by HIV, the prevention and/or treatment of the resulting acquired immune deficiency syndrome (AIDS), and the delay in the onset of AIDS. The present invention also relates to pharmaceutical compositions containing the compounds and to a method of use of the present compounds and other agents for the prevention and treatment of AIDS and viral infection by HIV.

The present invention is further directed to compounds which are modulators of CCR5 chemokine receptor activity and are useful in the prevention or treatment of certain inflammatory and immunoregulatory disorders and diseases, allergic diseases, atopic conditions including allergic rhinitis, dermatitis, conjunctivitis, and asthma, as well as autoimmune pathologies such as rheumatoid arthritis and atherosclerosis. The invention is also directed to pharmaceutical compositions comprising these compounds and the use of these compounds and compositions in the prevention or treatment of such diseases in which chemokine receptors are involved.

DETAILED DESCRIPTION OF THE INVENTION

The present invention includes compounds of Formula I:

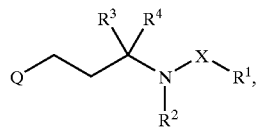

wherein

Q is

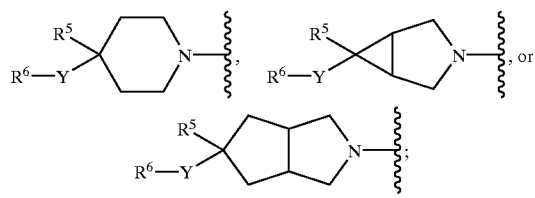

wherein "⁓" denotes the point of attachment;

$R^1$ is $C_{1-8}$ alkyl, $C_{2-8}$ alkenyl, $C_{2-8}$ alkynyl, $C_{3-8}$ cycloalkyl, $C_{5-8}$ cycloalkenyl, —O—$C_{3-8}$ cycloalkyl, —$NR^aR^b$, phenyl, naphthyl, or heterocycle; wherein any one of which except —$NR^aR^b$ is optionally substituted with one or more substituents independently selected from:

(a) halo,
(b) cyano,
(c) —OH,
(d) $C_{1-6}$ alkyl,
(e) —O—$C_{1-6}$ alkyl,
(f) $C_{1-6}$ haloalkyl,
(g) —O—$C_{1-6}$ haloalkyl,
(h) $C_{3-6}$ cycloalkyl,
(i) —O—$C_{3-6}$ cycloalkyl,
(j) $C_{2-6}$ alkenyl,
(k) —$NO_2$,
(l) phenyl, which is optionally substituted with one or more substituents independently selected from $C_{1-4}$ alkyl, —O—$C_{1-4}$ alkyl, halo, and —$CO_2R^c$,
(m) —$CO_2R^c$,
(n) —$NR^cR^d$,
(o) —$NR^c$—$COR^d$,
(p) —$NR^c$—$CO_2R^d$,
(q) —CO—$NR^cR^d$,
(r) —OCO—$NR^cR^d$,
(s) —$NR^cCO$—$NR^cR^d$,
(t) —$S(O)_p$—$R^c$,
(u) —$S(O)_2$—$NR^cR^d$,
(v) —$NR^cS(O)_2$—$R^d$,
(w) —$NR^cS(O)_2$—$NR^cR^d$,
(x) oxo,
(y) heterocyclyl, which is optionally substituted with one or more substituents independently selected from $C_{1-4}$ alkyl, —O—$C_{1-4}$ alkyl, halo, —$CO_2R^c$, and oxo,
(z) —$C_{5-7}$ cycloalkenyl, and
(aa) —C(=O)$R^c$;

X is a direct single bond, —C(=O)—, —C(=O)O—, —C(=O)N($R^e$)—, —$SO_2$—, or —C(=O)N($R^e$)$SO_2$—;

$R^2$ is hydrogen or $C_{1-8}$ alkyl which is optionally substituted with one or more substituents independently selected from halo, —$C_{1-6}$ haloalkyl, —O—$C_{1-6}$ alkyl, —O—$C_{1-6}$ haloalkyl, $C_{3-6}$ cycloalkyl, and —O—$C_{3-6}$ cycloalkyl;

or alternatively $R^1$ and $R^2$ together with the N to which $R^2$ is attached and the X, as defined above, to which $R^1$ is attached, form a 4- to 8-membered monocyclic ring containing from 1 to 3 nitrogen atoms, zero to 2 oxygen atoms, and zero to 2 sulfur atoms; wherein the ring is optionally substituted on one or more ring carbons with one or more substituents independently selected from:

(a) halo,
(b) cyano,
(c) —OH,
(d) $C_{1-6}$ alkyl,
(e) —O—$C_{1-6}$ alkyl,
(f) —$C_{1-6}$ haloalkyl, and
(g) —$S(O)_p$—$R^c$;

$R^3$ is hydrogen, —CO—$NR^cR^d$, or $C_{1-4}$ alkyl; wherein the alkyl is optionally substituted with one or more substituents independently selected from halo, —OH, —O—$C_{1-4}$ alkyl, or —O—$C_{1-4}$ haloalkyl;

$R^4$ is phenyl, naphthyl, or heterocycle, any one of which is optionally substituted with one or more substituents independently selected from (a) halo, (b) —CN,
(c) —OH,
(d) $C_{1-6}$ alkyl,
(e) —O—$C_{1-6}$ alkyl,
(f) $C_{1-6}$ haloalkyl,
(g) —NO$_2$,
(h) phenyl,
(i) —CO$_2$R$^c$,
(j) —NR$^c$R$^d$,
(k) —NR$^c$—COR$^d$,
(l) —NR$^c$—CO$_2$R$^d$,
(m) —CO—NR$^c$R$^d$,
(n) —OCO—NR$^c$R$^d$,
(o) —NR$^c$CO—NR$^c$R$^d$,
(p) —S(O)$_p$—R$^c$, wherein p is an integer selected from 0, 1 and 2,
(q) —S(O)$_2$—NR$^c$R$^d$,
(r) —NR$^c$S(O)$_2$—R$^d$,
(s) —NR$^c$S(O)$_2$—NR$^c$R$^d$,
(t) $C_{3-6}$ cycloalkyl,
(u) —O—$C_{3-6}$ cycloalkyl,
(v) —O—$C_{1-6}$ haloalkyl,
(w) $C_{2-6}$ alkenyl and
(x) oxo;

$R^5$ is:
(1) hydrogen,
(2) $C_{1-6}$ alkyl, which is optionally substituted with 1–4 substituents independently selected from —OH, cyano, and halo,
(3) cyano,
(4) —OH, or
(5) halo;

Y is:
(1) a direct single bond;
(2) —$C_{1-10}$ alkyl- or —($C_{0-6}$ alkyl)$C_{3-6}$cycloalkyl($C_{0-6}$ alkyl)—, either of which is optionally substituted with 1–7 substituents independently selected from:
(a) halo,
(b) —OH,
(c) —O—$C_{1-3}$ alkyl,
(d) trifluoromethyl,
(e) —($C_{1-3}$ alkyl)hydroxy, and
(f) ethylenedioxy;
(3) —($C_{0-6}$ alkyl)-$Z^1$—($C_{0-6}$ alkyl)—, wherein each alkyl is optionally substituted with 1–7 substituents independently selected from:
(a) halo,
(b) —OH,
(c) —O—$C_{1-3}$ alkyl, and
(d) trifluoromethyl;
and where $Z^1$ is selected from —SO$_2$—, —N(R$^f$)—, —N(R$^f$)C(=CHR$^u$)N(R$^f$)—, —N(R$^f$)C(=NR$^u$)N(R$^f$)—, —S—, —O—, —SO—, —SO$_2$N(R$^f$)—, —N(R$^f$)SO$_2$—, and —PO$_2$—;
(4) —($C_{0-6}$ alkyl)-$Z^2$—($C_{0-6}$ alkyl)-, wherein each alkyl is optionally substituted with 1–7 substituents independently selected from:
(a) halo,
(b) —OH,
(c) —O—$C_{1-3}$ alkyl, and
(d) trifluoromethyl;
and where $Z^2$ is selected from —C(=O)—, —C(=O)O—, —OC(=O)—, —C(=O)NR$^g$—, —NR$^g$C(=O)—, —OC(=O)NR$^g$—, —NR$^g$C(=O)O—, and —NR$^h$C(=O)NR$^g$—;

$R^6$ is phenyl, naphthyl, indanyl, tetrahydronaphthyl, biphenyl, or heterocycle; wherein any one of which is optionally substituted with 1–7 substituents independently selected from:
(a) halo,
(b) cyano,
(c) —OH,
(d) $C_{1-6}$ alkyl, which is unsubstituted or substituted with 1–5 of $R^7$,
(e) —O—$C_{1-6}$ alkyl, which is unsubstituted or substituted with 1–5 of $R^7$,
(f) —O—phenyl, which is unsubstituted or substituted with 1–5 of $R^8$,
(g) —O—heterocycle, which is unsubstituted or substituted with 1–5 of $R^8$,
(h) —NO$_2$,
(i) phenyl,
(l) —CO$_2$R$^s$,
(k) tetrazolyl,
(1) —NR$^s$R$^t$,
(m) —NR$^s$COR$^t$,
(n) —NR$^s$CO$_2$R$^t$,
(o) —CO—NR$^s$R$^t$,
(p) —OCO—NR$^s$R$^t$,
(q) —NR$^s$CO—NR$^s$R$^t$,
(r) —S(O)$_p$—R$^s$,
(s) —S(O) 2—NR$^s$R$^t$,
(t) —NR$^s$S(O)$_2$—R$^t$,
(u) —NR$^s$S(O)$_2$—NR$^s$R$^t$,
(v) $C_{2-6}$ alkenyl,
(w) furanyl, which is unsubstituted or substituted with benzyl which is unsubstituted or substituted with 1–7 of $R^8$,
(x) —$C_{3-6}$ cycloalkyl, and
(Y) —O—$C_{3-6}$ cycloalkyl;

each $R^7$ is independently halo, cyano, —OH, —O—$C_{1-6}$ alkyl, —$C_{3-6}$ cycloalkyl, —CO$_2$H, —CO$_2$—($C_{1-6}$ alkyl), —CF$_3$, —SO$_2$R$^s$, —NR$^s$R$^t$, phenyl, naphthyl, biphenyl, or heterocycle; wherein phenyl, naphthyl, biphenyl, or heterocycle is optionally substituted with 1–7 of $R^8$;

each $R^8$ is independently halo, cyano, —OH, $C_{1-6}$ alkyl, $C_{1-6}$ haloalkyl, —O—$C_{1-6}$ alkyl, —O—$C_{1-6}$ haloalkyl, —CO$_2$H, —CO$_2$($C_{1-6}$ alkyl), —NR$^s$R$^t$, —($C_{1-6}$ alkyl)—NR$^s$R$^t$, —SO$_2$R$^s$, —N(R$^s$)SO$_2$R$^t$, —N(R$^s$)COR$^t$, —($C_{1-6}$ alkyl)-OH, —O—$C_{3-6}$ cycloalkyl, benzyloxy, phenoxy, or —NO$_2$;

each of $R^a$ and $R^b$ is independently $C_{1-6}$ alkyl which is optionally substituted with one or more substituents independently selected from $C_{3-6}$ cycloalkyl, halo, CF$_3$, —O—$C_{1-6}$ alkyl, and —O—$C_{3-6}$ cycloalkyl;

each $R^c$ is independently hydrogen or $C_{1-4}$ alkyl;
each $R^d$ is independently hydrogen or $C_{1-4}$ alkyl;
$R^e$ is hydrogen or $C_{1-4}$ alkyl;
$R^f$ is hydrogen, $C_{1-6}$ alkyl, $C_{2-6}$ alkenyl, benzyl, phenyl, (CO)$C_{1-6}$ alkyl, —SO$_2$—$C_{1-6}$ alkyl, —SO$_2$-phenyl, —SO$_2$-heterocycle, or $C_{1-6}$ alkyl—$C_{3-6}$ cycloalkyl; wherein any of which except hydrogen is optionally substituted with 1–3 substituents independently selected from halo, $C_{1-3}$ alkyl, —O—$C_{1-3}$ alkyl and trifluoromethyl;

$R^g$ is hydrogen, $C_{1-6}$ alkyl, $C_{2-6}$ alkenyl, $C_{2-6}$ alkynyl, benzyl, phenyl, or $C_{1-6}$ alkyl-$C_{3-6}$ cycloalkyl; wherein any of which except hydrogen is optionally substituted with 1–3 substituents independently selected from halo, $C_{1-3}$ alkyl, —O—$C_{1-3}$ alkyl and trifluoromethyl;

Rh is hydrogen or $C_{1-6}$ alkyl;
each $R^s$ is independently hydrogen, $C_{1-6}$ alkyl, $C_{5-6}$ cycloalkyl, benzyl or phenyl; wherein any of which except hydrogen is optionally substituted with 1–3 substituents independently selected from halo, $C_{1-3}$ alkyl, —O—$C_{1-3}$ alkyl and trifluoromethyl;

each R' is independently hydrogen, $C_{1-6}$ alkyl, $C_{5-6}$ cycloalkyl, benzyl or phenyl; wherein any of which except hydrogen is optionally substituted with 1–3 substituents independently selected from halo, $C_{1-3}$ alkyl, —O—$C_{1-3}$ alkyl and trifluoromethyl;

R" is hydrogen, $C_{1-4}$ alkyl, —$NO_2$ or —CN; and
each p is independently an integer equal to 0, 1, or 2; and with the proviso that when Q is

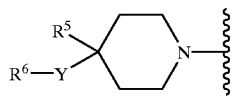

and Y is a direct single bond, then $R^6$ is phenyl, naphthyl, indanyl, tetrahydronaphthyl, biphenyl, or a heterocycle selected from pyrazolyl and tetrahydropyridopyrazolyl; wherein any one of which is optionally substituted as defined above;
or a pharmaceutically acceptable salt thereof.

A first embodiment of the present invention is a compound of Formula I as just defined above, except that:
(A) the definition of RI does not include $C_{5-8}$ cycloalkenyl,
(B) in the definition of $R^1$, the list of possible substituents does not include (z) and (aa), and substituent (y) is defined as heterocyclyl, which is optionally substituted with one or more substituents independently selected from $C_{1-4}$ alkyl, —O—$C_{1-4}$ alkyl, halo, and —$CO_2R^c$; and
(C) X is a direct single bond, —C(=O)—, —C(=O)O—, —C(=O)N($R^e$)—, or —$SO_2$—.

A second embodiment of the present invention is a compound of Formula I, wherein $R^1$ is $C_{1-8}$ alkyl, —O—$C_{1-8}$ alkyl, $C_{2-8}$ alkenyl, $C_{2-8}$ alkynyl, $C_{3-8}$ cycloalkyl, $C_{5-8}$ cycloalkenyl, —O—$C_{3-8}$ cycloalkyl, —$NR^aR^b$, phenyl, naphthyl, or a heterocycle selected from:
(i) a 4- to 6-membered saturated heterocycle containing from 1 to 3 heteroatoms selected from nitrogen, oxygen and sulfur,
(ii) a 5- to 6-membered heteroaromatic ring containing from 1 to 3 heteroatoms selected from nitrogen, oxygen, and sulfur; and
(iii) an 8- to 10-membered bicyclic heterocycle containing from 1 to 4 heteroatoms selected from nitrogen, oxygen and sulfur, either ring of which is saturated or unsaturated;
wherein any one of $R^1$ is optionally substituted with one or more substituents independently selected from:
(a) halo,
(b) cyano,
(c) —OH,
(d) $C_{1-4}$ alkyl,
(e) —O—$C_{1-4}$ alkyl,
(f) $C_{1-4}$ haloalkyl,
(g) —O—$C_{1-4}$ haloalkyl,
(h) —$NO_2$,
(i) phenyl,
(j) —$CO_2R^c$,
(k) —$NR^cR^d$,
(l) —NR—$COR^d$,
(m) —NR—$CO_2R^d$,
(n) —CO—$NR^cR^d$,
(o) —OCO—$NR^cR^d$,
(p) —$NR^cCO$—$NR^cR^d$,
(q) —$S(O)_p$—$R^c$, wherein p is an integer selected from 0, 1 and 2,
(r) —$S(O)_2$—$NR^cR^d$,
(s) —$NR^cS(O)_2$—$R^d$,
(t) —$NR^cS(O)_2$—$NR^cR^d$,
(u) oxo, and
(v) —C(=O)$R^c$;
and all other variables are as originally defined;
and with the proviso that when Q is

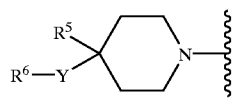

and Y is a direct single bond, then $R^6$ is phenyl, naphthyl, indanyl, tetrahydronaphthyl, biphenyl, or a heterocycle selected from pyrazolyl and tetrahydropyridopyrazolyl; wherein any one of which is optionally substituted in the manner originally defined above;
or a pharmaceutically acceptable salt thereof.

An aspect of the second embodiment is a compound of Formula I exactly as defined in the first embodiment, except that the definition of $R^1$ does not include $C_{5-8}$ cycloalkenyl, the list of possible substituents on $R^1$ does not include (v)

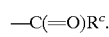

In another aspect of the second embodiment, $R^1$ is:
(i) $C_{1-4}$ alkyl which is optionally substituted with a substituent selected from:
(a) cyano,
(b) —O—$C_{1-4}$ alkyl,
(c) —$C_{3-6}$ cycloalkyl,
(d) —$C_{5-6}$ cycloalkenyl,
(e) —$CO_2H$,
(f) —$S(O)_2$—$NR^cR^d$,
(g) —S—$C_{1-4}$ alkyl, and
(h) a 5- or 6-membered saturated or unsaturated heterocycle containing from 1 to 3 heteroatoms selected from N, O and S, wherein the heterocycle is optionally substituted with 1 or 2 substituents independently selected from —$C_{1-6}$ alkyl and oxo;
(ii) cycloalkyl selected from cyclopropyl, cyclobutyl, cyclopentyl, and cyclohexyl, which is optionally substituted with from 1 to 3 substituents independently selected from:
(a) halo,
(b) —OH,
(c) cyano,
(d) $C_{1-6}$ alkyl, and
(e) —$CO_2H$;
(iii) phenyl which is optionally substituted with from 1 to 3 substituents independently selected from:
(a) halo,
(b) cyano,
(c) $C_{1-6}$ alkyl,
(d) —O—$C_{1-6}$ alkyl,
(e) $C_{1-6}$ haloalkyl,
(f) —O—$C_{1-4}$ haloalkyl, and
(g) —$CO_2H$;
(iv) a 4- to 6-membered saturated heterocycle selected from the group consisting of azetidinyl, oxacyclobutyl, pyrrolidinyl, tetrahydrofuranyl, 1,3-dioxacyclopentyl, morpholinyl, thiomorpholinyl, thiazolidinyl, oxazolidinyl, isooxazolidinyl, imidazolidinyl, piperazinyl, tetrahydrofuranyl, 1,4-dioxanyl, 1,3-dioxanyl, oxacyclohexyl, piperidinyl, and oxacyclopentyl; wherein the heterocycle is optionally substituted with from 1–3 substituents independently selected from:
(a) halo,
(b) cyano,
(c) $C_{1-6}$ alkyl,
(d) —O—$C_{1-6}$ alkyl,
(e) $C_{1-6}$ haloalkyl,
(f) —O—$C_{1-4}$ haloalkyl,
(g) $C_{3-6}$ cycloalkyl,
(h) —O—$C_{3-6}$ cycloalkyl,
(i) $C_{2-6}$ alkenyl,
(j) phenyl,
(k) oxo, and
(l) —C(=O)$R^c$;

(v) a 5- to 6-membered heteroaromatic selected from the group consisting of thienyl, pyridyl, imidazolyl, pyrrolyl, pyrazolyl, thiazolyl, isothiazolyl, pyrazinyl, pyrimidinyl, triazolyl, tetrazolyl, furanyl, oxazolyl, and isoxazolyl; wherein the heteroaromatic is optionally substituted with from 1–3 substituents independently selected from:
(a) halo,
(b) cyano,
(c) $C_{1-6}$ alkyl,
(d) —O—$C_{1-6}$ alkyl,
(e) $C_{1-6}$ haloalkyl,
(f) —O—$C_{1-4}$ haloalkyl,
(g) $C_{3-6}$ cycloalkyl,
(h) —O—$C_{3-6}$ cycloalkyl,
(i) $C_{2-6}$ alkenyl,
(j) phenyl, and
(k) oxo;

(vi) an 8- to 10-membered bicyclic heterocycle selected from the group consisting of benzimidazolyl, pyridoimidazolyl, indolyl, isoindolyl, phthalazinyl, purinyl, quinoxalinyl, quinazolinyl, cinnolinyl, quinolinyl, isoquinolinyl, indazolyl, dihydroindolyl, dihydroisoindolyl, tetrahydroquinolyl, tetrahydroisoquinolyl, and pyridopyrazolyl; wherein the bicyclic heterocycle is optionally substituted with from 1–3 substituents independently selected from:
(a) halo,
(b) cyano,
(c) $C_{1-6}$ alkyl,
(d) —O—$C_{1-6}$ alkyl,
(e) $C_{1-6}$ haloalkyl,
(f) —O—$C_{1-4}$ haloalkyl,
(g) $C_{3-6}$ cycloalkyl,
(h) —O—$C_{3-6}$ cycloalkyl,
(i) $C_{2-6}$ alkenyl,
(j) phenyl, and
(k) oxo.

In still another aspect of the second embodiment, $R^1$ is:
(i) a 4- to 6-membered saturated heterocycle selected from the group consisting of azetidinyl, oxacyclobutyl, pyrrolidinyl, tetrahydrofuranyl, 1,3-dioxacyclopentyl, morpholinyl, thiomorpholinyl, thiazolidinyl, oxazolidinyl, isooxazolidinyl, imidazolidinyl, piperazinyl, tetrahydrofuranyl, 1,4-dioxanyl, 1,3-dioxanyl, oxacyclohexyl, and piperidinyl; wherein the heterocycle is optionally substituted with from 1–3 substituents independently selected from:
(a) halo,
(b) cyano,
(c) $C_{1-6}$ alkyl,
(d) —O—$C_{1-6}$ alkyl,
(e) $C_{1-6}$ haloalkyl,
(f) —O—$C_{1-4}$ haloalkyl,
(g) $C_{3-6}$ cycloalkyl,
(h) —O—$C_{3-6}$ cycloalkyl,
(i) $C_{2-6}$ alkenyl,
(j) phenyl, and
(k) oxo;

(ii) a 5- to 6-membered heteroaromatic selected from the group consisting of thienyl, pyridyl, imidazolyl, pyrrolyl, pyrazolyl, thiazolyl, isothiazolyl, pyrazinyl, pyrimindinyl, triazolyl, and tetrazolyl; wherein the heteroaromatic is optionally substituted with from 1–3 substituents independently selected from:
(a) halo,
(b) cyano,
(c) $C_{1-6}$ alkyl,
(d) —O—$C_{1-6}$ alkyl,
(e) $C_{1-6}$ haloalkyl,
(f) —O—$C_{1-4}$ haloalkyl,
(g) $C_{3-6}$ cycloalkyl,
(h) —O—$C_{3-6}$ cycloalkyl,
(i) $C_{2-6}$ alkenyl,
(j) phenyl, and
(k) oxo;

(iii) an 8- to 10-membered bicyclic heterocycle selected from the group consisting of benzimidazolyl, pyridoimidazolyl, indolyl, isoindolyl, phthalazinyl, purinyl, quinoxalinyl, quinazolinyl, cinnolinyl, quinolinyl, isoquinolinyl, indazolyl, dihydroindolyl, dihydroisoindolyl, tetrahydroquinolyl, tetrahydroisoquinolyl, and pyridopyrazolyl; wherein the bicyclic heterocycle is optionally substituted with from 1–3 substituents independently selected from:
(a) halo,
(b) cyano,
(c) $C_{1-6}$ alkyl,
(d) —O—$C_{1-6}$ alkyl,
(e) $C_{1-6}$ haloalkyl,
(f) —O—$C_{1-4}$ haloalkyl,
(g) $C_{3-6}$ cycloalkyl,
(h) —O—$C_{3-6}$ cycloalkyl,
(i) $C_{2-6}$ alkenyl,
(j) phenyl, and
(k) oxo.

A third embodiment of the present invention is a compound of Formula I, wherein $R^2$ is hydrogen or $C_{1-6}$ alkyl which is optionally substituted with one or more substituents independently selected from fluoro, —$CF_3$, —O—$C_{1-4}$ alkyl, $C_{3-6}$ cycloalkyl, and —O—$C_{3-6}$ cycloalkyl;

and all other variables are as originally defined;

and with the proviso that when Q is

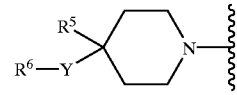

and Y is a direct single bond, then $R^6$ is phenyl, naphthyl, indanyl, tetrahydronaphthyl, biphenyl, or a heterocycle selected from pyrazolyl and tetrahydropyridopyrazolyl; wherein any one of which is optionally substituted in the manner originally defined above;

or a pharmaceutically acceptable salt thereof.

A fourth embodiment of the present invention is a compound of Formula I, wherein $R^3$ is hydrogen;

and all other variables are as originally defined;

and with the proviso that when Q is

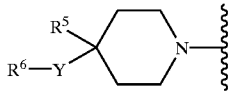

Y is a direct single bond, then $R^6$ is phenyl, naphthyl, indanyl, tetrahydronaphthyl, biphenyl, or a heterocycle selected from pyrazolyl and tetrahydropyridopyrazolyl; wherein any one of which is optionally substituted in the manner originally defined above;

or a pharmaceutically acceptable salt thereof.

A fifth embodiment of the present invention is a compound of Formula I, wherein $R^4$ is phenyl or heterocycle, wherein the phenyl or heterocycle is optionally substituted with from 1 to 4 substituents independently selected from (a) halo,
(b) —CN,
(c) —OH,
(d) $C_{1-4}$ alkyl,
(e) —O—$C_{1-4}$ alkyl,
(f) $CF_3$,
(g) —$NO_2$,
(h) phenyl,
(i) —$CO_2R^c$,
(j) —$NR^cR^d$,
(k) —$NR^c$—$COR^d$,
(l) —$NR^c$—$CO_2R^d$,
(m) —CO—$NR^cR^d$,
(n) —OCO—$NR^cR^d$,
(o) —$NR^c$CO—$NR^cR^d$,
(p) —$S(O)_p$—$R^c$,
(q) —$S(O)_2$—$NR^cR^d$,
(r) —$NR^cS(O)_2$—$R^d$,
(s) —$NR^cS(O)_2$—$NR^cR^d$,
(t) $C_{3-6}$ cycloalkyl, and
(u) —O—$C_{3-6}$ cycloalkyl;

and all other variables are as originally defined;

and with the proviso that when Q is

sand Y is a direct single bond, then $R^6$ is phenyl, naphthyl, indanyl, tetrahydronaphthyl, biphenyl, or a heterocycle selected from pyrazolyl and tetrahydropyridopyrazolyl; wherein any one of which is optionally substituted in the manner originally defined above;

or a pharmaceutically acceptable salt thereof.

A sixth embodiment of the present invention is a compound of Formula I, wherein $R^5$ is hydrogen or fluoro;

and all other variables are as originally defined;

and with the proviso that when Q is

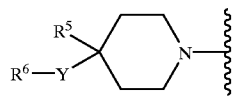

and Y is a direct single bond, then $R^6$ is phenyl, naphthyl, indanyl, tetrahydronaphthyl, biphenyl, or a heterocycle selected from pyrazolyl and tetrahydropyridopyrazolyl; wherein any one of which is optionally substituted in the manner originally defined above;

or a pharmaceutically acceptable salt thereof.

In an aspect of the sixth embodiment, $R^5$ is hydrogen.

A seventh embodiment of the present invention is a compound of Formula I, wherein Y is (1) a direct single bond;
(2) —$C_{1-6}$ alkyl-, which is optionally substituted with 1–7 substituents independently selected from:
  (a) halo,
  (b) —OH,
  (c) —O—$C_{1-3}$ alkyl, and
  (d) trifluoromethyl;
(3) —($C_{0-2}$ alkyl)-$Z^1$—($C_{0-2}$ alkyl)-, wherein the alkyl is unsubstituted;
  $Z^1$ is selected from —$SO_2$—, —SO—, —$N(R^f)$—, —$SO_2N(R^f)$—, —S—, and —O—;
  and $R^f$ is $C_{1-4}$ alkyl, $C_{2-5}$ alkenyl, or $C_{1-3}$ alkyl-$C_{3-6}$ cycloalkyl; or
(4) —($C_{0-2}$ alkyl)-$Z^2$—($C_{0-2}$ alkyl)-, wherein the alkyl is optionally substituted with 1–4 substituents independently selected from:
  (a) halo,
  (b) —OH,
  (c) —O—$C_{1-3}$ alkyl, and
  (d) trifluoromethyl;
  and wherein
  $Z^2$ is selected from —C(=O)$NR^g$—, —$NR^gC(=O)$—, —OC(=O)$NR^g$—, —$NR^gC(=O)O$—, and —$NR^hC(=O)NR^g$—;
  $R^g$ is hydrogen, $C_{1-6}$ alkyl, $C_{2-6}$ alkenyl, $C_{2-6}$ alkynyl, benzyl, phenyl, or $C_{1-6}$ alkyl-$C_{3-6}$ cycloalkyl; wherein any of which except hydrogen is optionally substituted with from 1 to 3 substituents independently selected from halo, $C_{1-3}$ alkyl, —O—$C_{1-3}$ alkyl and trifluoromethyl; and
  $R^h$ is —H or $C_{1-6}$ alkyl;

and all other variables are as originally defined;

and with the proviso that when Q is

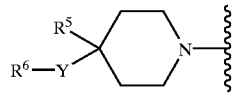

and Y is a direct single bond, then $R^6$ is phenyl, naphthyl, indanyl, tetrahydronaphthyl, biphenyl, or a heterocycle selected from pyrazolyl and tetrahydropyridopyrazolyl; wherein any one of which is optionally substituted in the manner originally defined above;

or a pharmaceutically acceptable salt thereof.

In one aspect of the seventh embodiment, Y is (1) a direct single bond;
(2) —$C_{2-4}$ alkyl-, which is optionally substituted with 1–6 substituents independently selected from:

(a) halo,
(b) —O—$C_{1-3}$ alkyl, and
(c) trifluoromethyl;
(3) selected from
—($C_{0-2}$ alkyl)-$SO_2$—($CO_2$ alkyl)-,
—($C_{0-2}$ alkyl)-$SO_2$N($R^f$)—($CO_2$ alkyl),
—($C_{0-2}$ alkyl)-SO—($CO_2$ alkyl)-,
—($C_{0-2}$ alkyl)-S—($CO_2$ alkyl)-,
—($C_{0-2}$ alkyl)-O—($CO_2$ alkyl)-, and
—($C_{0-2}$ alkyl)-N($R^f$)—($CO_2$ alkyl)-; and
where $R^f$ is $C_{2-4}$ alkyl, $C_{2-3}$ alkenyl or $C_{1-2}$ alkyl-$C_3$ cycloalkyl;
(4) —($C_{0-2}$ alkyl)-$Z^2$—($CO_2$ alkyl)-, wherein the alkyl is not substituted;
and where
$Z^2$ is selected from —C(=O)$NR^g$—, —$NR^g$C(=O)—, —OC(=O)$NR^g$—, —$NR^g$C(=O)O—, and —$NR^h$C(=O)$NR^g$—;
$R^g$ is hydrogen, $C_{1-3}$ alkyl, $C_{2-3}$ alkenyl, or $C_{2-3}$ alkynyl; and
$R^h$ is —H or $C_{1-4}$ alkyl.
In another aspect of the seventh embodiment, Y is
(1) a direct single bond;
(2) $C_{2-4}$ alkyl, which is optionally substituted with from 1 to 6 fluoros;
(3) selected from:
(a) —$SO_2CH_2CH_2$—,
(b) —SO—$CH_2CH_2$—,
(c) —$SCH_2CH_2$—,
(d) —$CH_2$—O—$CH_2$—,
(e) —N($CH_2CH_3$)—,
(f) —N($CH_2CH_2CH_3$)—, and
(g) —N($CH_2$-cyclopropyl)-; or
(4) selected from:
(a) —$CH_2$OC(=O)—N($C_{1-4}$ alkyl)-,
(b) —$CH_2$—OC(=O)N(allyl)-,
(c) —$CH_2$NHC(=O)N($C_{1-4}$ alkyl)-,
(d) —$CH_2$NHC(=O)N(allyl), and
(e) —$CH_2CH_2$NHC(=O)N($CH_2CH_3$)—.

In still another aspect of the seventh embodiment, Y is a direct single bond, in which case there is a proviso that when Q is

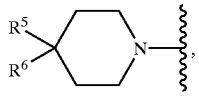

then $R^6$ is phenyl, naphthyl, indanyl, tetrahydronaphthyl, biphenyl, or a heterocycle selected from pyrazolyl and tetrahydropyridopyrazolyl; wherein any one of which is optionally substituted in the manner originally defined.

An eighth embodiment of the present invention is a compound of Formula I, wherein $R^6$ is phenyl, benzoimidazolyl, imidazolyl, pyridoimidazolyl, isoxazolyl, oxazolyl, pyrazolyl, pyridyl, thiazolyl, imidazothiophenyl, indazolyl, tetrahydropyridoimidazolyl, tetrahydroindazolyl, dihydrothiopyranopyrazolyl, dihydrodioxothiopyranopyrazolyl, dihydropyranopyrazolyl, tetrahydropyridopyrazolyl, or triazolyl (e.g., 1,2,4-triazolyl); wherein any of which is optionally substituted with from 1 to 7 substituents independently selected from:
(a) halo,
(b) cyano,
(c) —OH,
(d) $C_{1-6}$ alkyl, which is unsubstituted or substituted with 1–5 of $R^7$
(e) —O—$C_{1-6}$ alkyl, which is unsubstituted or substituted with 1–5 of $R^7$,
(f) —$NO_2$,
(g) phenyl,
(h) —$CO_2R^s$,
(i) tetrazolyl,
(j) —$NR^sR^t$,
(k) —$NR^sCOR^t$,
(l) —$NR^s$—$CO_2R^t$,
(m) —CO—$NR^sR^t$,
(n) —OCO—$NR^sR^t$,
(o) —$NR^sCO$—$NR^sR^t$,
(p) —$S(O)_p$—RS,
(q) —$S(O)_2$—$NR^sR^t$,
(r) —$NR^sS(O)_2$—$R^t$,
(s) —$NR^sS(O)_2$—$NR^sR^t$,
(t) —$C_{3-5}$ cycloalkyl, and
(t) —O—$C_{3-5}$ cycloalkyl;
each $R^7$ is independently halo, cyano, —OH, —O—$C_{1-6}$ alkyl, —$C_{3-5}$ cycloalkyl, —$CO_2H$, —$CO_2(C_{1-6}$ alkyl), —$CF_3$,—$SO_2R^s$, —$NR^sR^t$, phenyl, naphthyl, biphenyl, or heterocycle; wherein phenyl, naphthyl, biphenyl, or heterocycle is optionally substituted with 1–7 of $R^8$;
each $R^8$ is independently halo, cyano, —OH, $C_{1-4}$ alkyl, —O—$C_{1-4}$ alkyl, —O—$C_{3-5}$ cycloalkyl, —$CO_2H$, —$CO_2(C_{1-6}$ alkyl), —$CF_3$, —$OCF_3$, —$SO_2R^a$, —$N(R^a)SO_2R^b$, or —$NR^sR^t$;
each $R^s$ is independently hydrogen, $C_{1-6}$ alkyl, $C_{5-6}$ cycloalkyl, benzyl or phenyl, wherein any of which except hydrogen is optionally substituted with 1–3 substituents independently selected from halo, $C_{1-3}$ alkyl, —O—$C_{1-3}$ alkyl, $C_{1-3}$ fluoroalkyl, and —O—$C_{1-3}$ fluoroalkyl; and
each $R^t$ is independently hydrogen, $C_{1-6}$ alkyl, $C_{5-6}$ cycloalkyl, benzyl or phenyl, wherein any of which except hydrogen is optionally substituted with 1–3 substituents independently selected from halo, $C_{1-3}$ alkyl, —O—$C_{1-3}$ alkyl, $C_{1-3}$ fluoroalkyl, and —O—$C_{1-3}$ fluoroalkyl;

and all other variables are as originally defined;
and with the proviso that when Q is

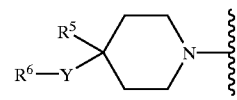

and Y is a direct single bond, then $R^6$ is phenyl or a heterocycle selected from pyrazolyl and tetrahydropyridopyrazolyl; wherein the phenyl or heterocycle is optionally substituted as just defined above;
or a pharmaceutically acceptable salt thereof.

An aspect of the eighth embodiment is a compound of Formula I exactly as defined in the eighth embodiment, except that the definition of $R^6$ does not include triazolyl.

A ninth embodiment of the present invention is a compound of Formula I, wherein $R^6$ is benzimidazolyl, imidazolyl, pyridoimidazolyl, isoxazolyl, oxazolyl, pyrazolyl, pyridyl, thiazolyl, imidazothiophenyl, indazolyl, tetrahydropyridoimidazolyl, tetrahydroindazolyl, dihydrothiopyranopyrazolyl, dihydrodioxothiopyrano-pyrazolyl, dihydropyranopyrazolyl, tetrahydropyrido-pyrazolyl, or triazolyl; wherein any of which is optionally substituted with from 1 to 5 substituents independently selected from:

(a) halo,
(b) cyano,
(c) —$NO_2$,
(d) —$CF_3$,
(e) —$CHF_2$,
(f) —$CH_2F$,
(g) —$CH_2OH$,
(h) —$CH_2OCH_3$,
(i) —$(CH_2)_{1-2}SO_2$—($C_{1-2}$ alkyl)
(j) phenyl,
(k) $C_{1-6}$ alkyl, which is optionally substituted with phenyl, which is optionally substituted with from 1 to 4 substituents independently selected from halo, cyano, —OH, —O—$C_{1-6}$ alkyl, —O—$C_{3-5}$ cycloalkyl, —$CO_2H$, —$CO_2(C_{1-6}$ alkyl), —$CF_3$,—$OCF_3$, and —$SO_2$—($C_{1-3}$ alkyl);
(l) —O—$C_{1-6}$ alkyl,
(m) —$C_{3-5}$ cycloalkyl,
(n) —$CH_2$—($C_{3-5}$ cycloalkyl), and
(o) —O—$C_{3-5}$ cycloalkyl;
and all other variables are as originally defined;
and with the proviso that when Q is

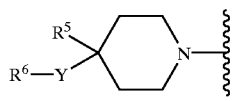

and Y is a direct single bond, then $R^6$ is pyrazolyl or tetrahydropyridopyrazolyl, either of which is optionally substituted as just defined above;

or a pharmaceutically acceptable salt thereof.

An aspect of the ninth embodiment is a compound of Formula I exactly as defined in the ninth embodiment, except that the definition of $R^6$ does not include triazolyl.

A tenth embodiment of the present invention is a compound of Formula I, wherein Q is

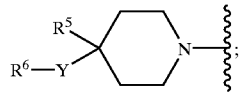

and all other variables are as originally defined;
and with the proviso that when Y is a direct single bond, then $R^6$ is phenyl, naphthyl, indanyl, tetrahydro-naphthyl, biphenyl, or a heterocycle selected from pyrazolyl and tetrahydropyridopyrazolyl; wherein any one of which is optionally substituted in the manner originally defined;

or a pharmaceutically acceptable salt thereof.

An eleventh embodiment of the present invention is a compound of Formula I, wherein Q is

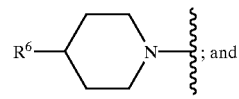

$R^6$ is phenyl, naphthyl, indanyl, tetrahydronaphthyl, biphenyl, or a heterocycle selected from pyrazolyl and tetrahydropyridopyrazolyl; wherein any one of which is optionally substituted in the manner originally defined above;

and all other variables are as originally defined;
or a pharmaceutically acceptable salt thereof.

It is to be understood that additional embodiments of the present invention include, but are not limited to, compounds of Formula I wherein each of two or three or more of $R^1$, $R^2$, $R^3$, $R^4$, $R^5$, $R^6$, X, Y and Q is independently defined in accordance with one of the foregoing embodiments or aspects thereof as set forth above. Any and all possible combinations of these variables in Formula I are within the scope of the present invention, subject to the proviso set forth above relating Q, Y and $R^6$.

A first class of the present invention is compounds of Formula (II):

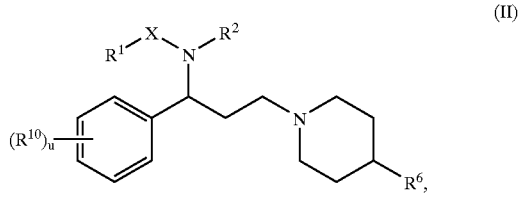

wherein
X is —C(=O)— or —$SO_2$—;
$R^1$ is $C_{1-4}$alkyl or is:

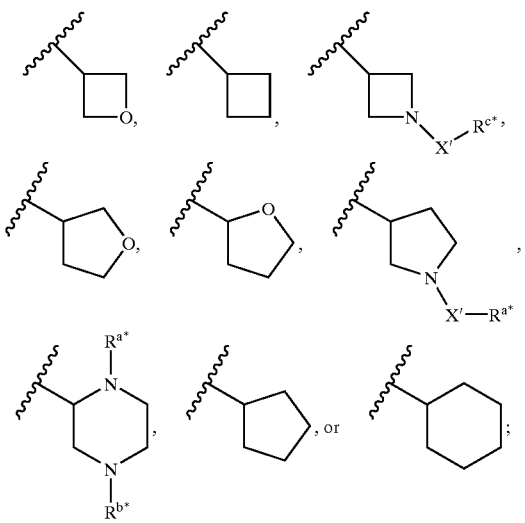

wherein
X' independently has the same definition as X;
each of $R^{a*}$ and $R^{b*}$ is independently $C_{1-6}$ alkyl which is optionally substituted with one or more substituents independently selected from $C_{3-6}$ cycloalkyl, halo, $CF_3$, —O—$C_{1-6}$ alkyl, and —O—$C_{3-6}$ cycloalkyl;
$R^{c*}$ is hydrogen or $C_{1-4}$ alkyl;

$R^2$ is hydrogen or $C_{1-8}$ alkyl;

$R^3$ is hydrogen;

$R^6$ is

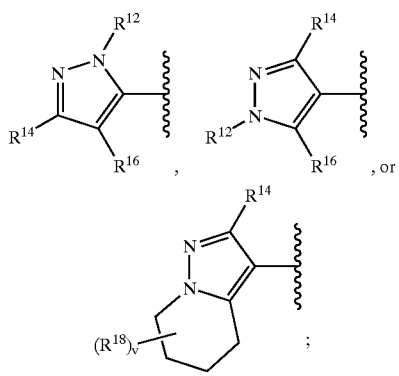

each $R^{10}$ is independently $C_{1-4}$ alkyl, —O—$C_{1-4}$ alkyl, —$CF_3$, —$OCF_3$, —OH, —CN, or halo;

$R^{12}$ is —H, $C_{1-4}$ alkyl, or —$CH_2$-phenyl wherein the phenyl is optionally substituted with 1 or 2 substituents independently selected from chloro, fluoro, —CN, —$C_{1-3}$ alkyl, —O—$C_{1-3}$ alkyl, —O—cyclopropyl, —O—cyclobutyl, —$CF_3$, —$OCF_3$, —$SO_2$—($C_{1-3}$ alkyl), and —N(H)$SO_2$—($C_{1-3}$ alkyl);

each of $R^{14}$ and $R^{16}$ is independently —H, $C_{1-4}$ alkyl, —O—$C_{1-4}$ alkyl, $CF_3$, —OH, —CN, halo, or —$CH_2$-phenyl wherein the phenyl is optionally substituted with 1 or 2 substituents independently selected from chloro, fluoro, —CN, —$C_{1-3}$ alkyl, —O—$C_{1-3}$ alkyl, —O—cyclopropyl, —O—cyclobutyl, —$CF_3$, —$OCF_3$, —$SO_2$—($C_{1-3}$ alkyl), and —N(H)$SO_2$—($C_{1-3}$ alkyl);

each $R^{18}$ is independently $C_{1-4}$ alkyl, —O—$C_{1-4}$ alkyl, —$CF_3$, —$OCF_3$, —OH, —CN, or halo;

u is an integer from zero to 4; and v is an integer from zero to 3;

or a pharmaceutically acceptable salt thereof.

A sub-class of the first class is a compound of Formula (II), wherein $R^1$ is:

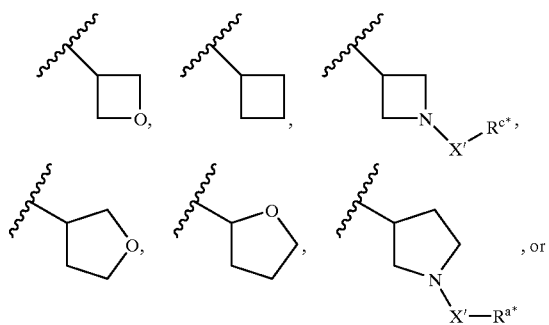

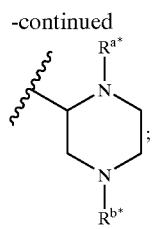

and all other variables are as defined above in the first class;

or a pharmaceutically acceptable salt thereof.

The compounds of the instant invention have at least one asymmetric center carbon atom substituted by N, $R^3$, $R^4$ and $CH_2CH_2$—Q in Formula I. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention.

Another sub-class of the first class are compounds of Formula (III):

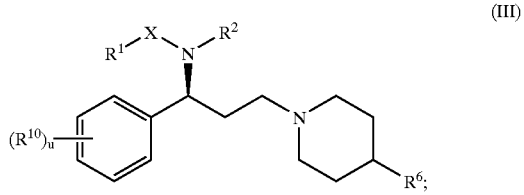

(III)

wherein all of the variables are as defined in the first class above;

or a pharmaceutically acceptable salt thereof.

The independent syntheses of the optical isomers described above or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

Other embodiments of the present invention include the following:

(a) A pharmaceutical composition comprising a compound of Formula (I) and a pharmaceutically acceptable carrier.

(b) The pharmaceutical composition of (a), further comprising at least one antiviral selected from the group consisting of HIV protease inhibitors, non-nucleoside HIV reverse transcriptase inhibitors, and nucleoside HIV reverse transcriptase inhibitors.

(c) A method for modulating (e.g., inhibiting) CCR5 chemokine receptor activity in a subject which comprises administering to the subject an effective amount of the compound of Formula (I).

(d) A method of preventing or treating infection by HIV in a subject in need thereof which comprises administering to the subject a therapeutically effective amount of a compound of Formula (I).

(e) The method of (d), wherein the compound of Formula (I) is administered in combination with a therapeutically effective amount of at least one antiviral selected from the group consisting of HIV protease inhibitors, non-nucleoside HIV reverse transcriptase inhibitors, and nucleoside HIV reverse transcriptase inhibitors.

(f) A method of delaying the onset of AIDS or treating AIDS in a subject in need thereof which comprises administering to the subject a therapeutically effective amount of a compound of Formula (I).

(g) The method of (f), wherein the compound is administered in combination with a therapeutically effective amount of at least one antiviral selected from the group consisting of HIV protease inhibitors, non-nucleoside HIV reverse transcriptase inhibitors, and nucleoside HIV reverse transcriptase inhibitors (h) A method of modulating (e.g., inhibiting) CCR5 chemokine receptor acitivity in a subject in need thereof which comprises administering to the subject a therapeutically effective amount of the composition of (a) or (b).

(i) A method of preventing or treating infection by HIV in a subject in need thereof which comprises administering to the subject a therapeutically effective amount of the composition of (a) or (b).

(j) A method of treating AIDS or delaying the onset of AIDS in a subject in need thereof which comprises administering to the subject a therapeutically effective amount of the composition of (a) or (b).

Still other embodiments of the present invention include the following:

(k) A pharmaceutical composition which comprises the product prepared by combining (e.g., mixing) an effective amount of a compound of Formula (I) and a pharmaceutically acceptable carrier.

(l) A combination useful for treating or preventing infection by HIV, or for preventing, treating or delaying the onset of AIDS, which is a therapeutically effective amount of a compound of Formula (I) and a therapeutically effective amount of an HIV infection/AIDS treatment agent selected from the group consisting of HIV/AIDS antiviral agents, immunomodulators, and anti-infective agents.

(m) The combination of (1), wherein the HIV infection/AIDS treatment agent is an antiviral selected from the group consisting of HV protease inhibitors, non-nucleoside HIV reverse transcriptase inhibitors and nucleoside HIV reverse transcriptase inhibitors.

Additional embodiments of the invention include the pharmaceutical compositions and methods set forth in (a)–(j) above and the compositions and combinations set forth in (k)–(m), wherein the compound employed therein is a compound of one of the embodiments, classes, sub-classes, or aspects of compounds described above. In all of these embodiments, the compound may optionally be used in the form of a pharmaceutically acceptable salt.

As used herein, the term "$C_{1-6}$ alkyl" (or "$C_1$–$C_6$ alkyl") means linear or branched chain alkyl groups having from 1 to 6 carbon atoms and includes all of the hexyl alkyl and pentyl alkyl isomers as well as n-, iso-, sec- and t-butyl, n- and isopropyl, ethyl and methyl. "$C_{1-4}$ alkyl" means n-, iso-, sec- and t-butyl, n- and isopropyl, ethyl and methyl. Similar terms such as "$C_{1-10}$ alkyl" have analogous meanings.

The term "$C_0$" as employed in expressions such as "$C_{0-6}$ alkyl" means a direct covalent bond.

The term "$C_{2-6}$ alkenyl" (or "$C_2$–$C_6$ alkenyl") means linear or branched chain alkenyl groups having from 2 to 6 carbon atoms and includes all of the hexenyl and pentenyl isomers as well as 1-butenyl, 2-butenyl, 3-butenyl, isobutenyl, 1-propenyl, 2-propenyl, and ethenyl (or vinyl). Similar terms such as "$C_{2-10}$ alkenyl" have analogous meanings.

The term "$C_{2-6}$ alkynyl" (or "$C_2$–$C_6$ alkynyl") means linear or branched chain alkynyl groups having from 2 to 6 carbon atoms and includes all of the hexynyl and pentynyl isomers as well as 1-butynyl, 2-butynyl, 3-butynyl, 1-propynyl, 2-propynyl, and ethynyl (or acetylenyl). Similar terms such as "$C_{2-10}$ alkynyl" have analogous meanings.

The term "$C_{3-8}$ cycloalkyl" (or "$C_3$–$C_8$ cycloalkyl") means a cyclic ring of an alkane having three to eight total carbon atoms (i.e., cyclopropyl, cyclobutyl, cyclopentyl, cyclohexyl, cycloheptyl, or cyclooctyl). The term "$C_{3-6}$ cycloalkyl" refers to a cyclic ring selected from cyclopropyl, cyclobutyl, cyclopentyl, and cyclohexyl. Similar terms such as "$C_{5-6}$ cycloalkyl" have analogous meanings.

The term "halogen" (or "halo") refers to fluorine, chlorine, bromine and iodine (alternatively, fluoro, chloro, bromo, and iodo).

The term "$C_{1-6}$ haloalkyl" (which may alternatively be referred to as "$C_1$–$C_6$ haloalkyl" or "halogenated $C_1$–$C_6$ alkyl") means a $C_1$ to $C_6$ linear or branched alkyl group as defined above with one or more halogen substituents. The term "$C_{1-4}$ haloalkyl" has an analogous meaning. Similarly, "$C_{1-6}$ fluoroalkyl" means a $C_1$ to $C_6$ linear or branched alkyl group as defined above with one or more fluorine substituents. Representative examples of suitable fluoroalkyls include the series $(CH_2)_{0-4}CF_3$ (i.e., trifluoromethyl, 2,2,2-trifluoroethyl, 3,3,3-trifluoro-n-propyl, etc.), 1-fluoroethyl, 2-fluoroethyl, 2,2-difluoroethyl, 3,3,3-trifluoroisopropyl, 1,1,1,3,3,3-hexafluoroisopropyl, and perfluorohexyl.

The term "—($C_{1-3}$ alkyl)hydroxy" refers to a $C_{1-3}$ alkyl group as defined above which is substituted on one its carbons by a hydroxy group. Exemplary groups include hydroxymethyl, hydroxyethyl, 3-hydroxy-n-propyl, 2-hydroxy-n-propyl, and so forth.

The term "heterocycle" (and variations thereof such as "heterocyclic" or "heterocyclyl") broadly refers to a 4- to 8-membered monocyclic ring, 7- to 14-membered bicyclic ring system, or an 11 to 16-membered tricyclic ring system, any ring of which is saturated or unsaturated, and which consists of carbon atoms and one or more heteroatoms (e.g., from 1 to 4 heteroatoms) selected from N, O and S, and wherein the nitrogen and sulfur heteroatoms may optionally be oxidized, and the nitrogen heteroatom may optionally be quaternized. The heterocyclic ring may be attached at any heteroatom or carbon atom, provided that attachment results in the creation of a stable structure.

The term "heterocycle" as used herein is intended to include the following groups: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, methylenedioxybenzyl, tetrahydrofuranyl, and tetrahydrothienyl, and N-oxides thereof.

The term "heterocycle" as used herein is also intended to include, but is not limited to, the following groups: methylenedioxyphenyl, imidazopyridyl, imidazopyrimidinyl, imidazopyridazinyl, imidazopyrazinyl, imidazotriazinyl, imidazothipheyl, pyrazolopyridyl, pyrazolopyrimidinyl, pyrazolopyridazinyl, pyrazolopyrazinyl, pyrazolotriazinyl, pyrazolothiophenyl, triazolopyridyl, triazolopyrimidinyl, triazolopyridazinyl, triazolopyrazinyl, triazolothiophenyl, tetrahydroimidazopyridinyl, tetrahydropyrazolopyridinyl, tetrahydrotriazopyridinyl, tetrahydrotriazolopyridazinyl, and tetrahydroindazolyl.

The term "heterocycle" as used herein is also intended to include, but is not limited to, the following groups: tetrahydroimidazopyrimidyl, tetrahydroimidazopyrazinyl, tetrahydroimidazopyridazinyl, tetrahydrotriazolopyrimidyl, tetrahydrotriazolopyrazinyl, tetrahydropyrazolopyrimidyl, tetrahydropyrazolopyrazinyl, imidazothiazolyl, and imidazothiadiazolyl.

The term "heterocycle" as used herein is also intended to include, but is not limited to, oxopyridinyl (e.g., 2-oxopyridinyl), oxopiperidinyl, and oxopyrazolyl.

The terms "thiophenyl" and "thienyl" have the same meaning herein and are used interchangeably. Similarly, the following pairs of terms have the same meaning: "indazolyl" and "benzopyrazolyl" ; "pyridinyl" and "pyridyl".

Unless expressly set forth to the contrary, an "unsaturated" ring is a partially or fully unsaturated ring.

The term "substituted" in reference to substitution on alkyl, cycloalkyl, phenyl, heterocycle, or some other chemical group is intended to include mono- and poly-substitution by a named substituent to the extent such single and multiple substitution is chemically allowed in any of the named chemical groups.

It is understood that the definition of a substituent at a particular location in a molecule is independent of its definition at other locations in the molecule. Thus, for example, when $Z^1$=—N(R$^f$)C(=CHR")N(R$^f$)—, the value of R$^f$ (defined elsewhere) on one of the nitrogens is independent of the value of R$^f$ at the other nitrogen; i.e., they can be the same or different.

Exemplifying the invention is the use of the compounds disclosed in the Examples.

Exemplary compounds of the present invention include compounds selected from the group consisting of:

N-[1(S)-1-phenyl-3-(4-[3-benzyl-1-ethyl(1H-pyrazol-5-yl)]piperidin-1-yl)propyl]cyclobutanecarboxamide;
N-[1(S)-1-phenyl-3-(4-[3-benzyl-1-ethyl(1H-pyrazol-5-yl)]piperidin-1-yl)propyl]N-acetyl-3-azetadinecarboxamide;
N-[1(S)-1-phenyl-3-(4-[3-benzyl-1-ethyl(1H-pyrazol-5-yl)]piperidin-1-yl)propyl]-3-carboxypropylcarboxamide;
N-[1(S)-1-phenyl-3-(4-[3-benzyl-1-ethyl(1H-pyrazol-5-yl)]piperidin-1-yl)propyl]methylsulfonamide;
N-{(1S)-3-[4-(3-benzyl-1-ethyl-1H-pyrazol-5-yl)piperidin-1-yl]-1-phenylpropyl}ethanesulfonamide;
N-{(1S)-3-[4-(3-benzyl-1-ethyl-1H-pyrazol-5-yl)piperidin-1-yl]-1-phenylpropyl}thiophene-2-sulfonamide;
2(+/−)-(N-[1(S)-1-phenyl-3-(4-[3-benzyl-1-ethyl(1H-pyrazol-5-yl)]piperidin-1-yl)propyl]amino)butanoic acid;
N-{(1S)-3-[4-(3-benzyl-1-ethyl-1H-pyrazol-5-yl)piperidin-1-yl]-1-phenylpropyl}isoleucine;
({(1S)-3-[4-(3-benzyl-1-ethyl-1H-pyrazol-5-yl)piperidin-1-yl]-1-phenylpropyl}amino)(2-furyl)acetic acid;
3-[1-({(1S)-3-[4-(3-benzyl-1-ethyl-1H-pyrazol-5-yl)piperidin-1-yl]-1-phenylpropyl}amino)ethyl]benzoic acid;
N-[1(S)-1-phenyl-3-(4-[2-ethyl-4,5,6,7-tetrahydropyrazolo(1,5-α)pyridin-3-yl]piperidin-1-yl)propyl]cyclobutanecarboxamide;
N-[1(S)-1-phenyl-3-(4-[3-ethyl-1-(4-[ethylsulfonyl]benzyl)-(1H-pyrazol-5-yl)-piperidin-1-yl)propyl]cyclobutanecarboxamide;
N-[1(S)-1-phenyl-3-(4-[1,3-diethyl-5-methyl(H-pyrazol-4-yl]piperidin-1-yl)propyl]cyclobutanecarboxamide;
N-[1(S)-1-(3-fluorophenyl)-3-(4-[2-ethyl-4,5,6,7-tetrahydropyrazolo(1,5-α)pyridin3-yl]piperidin-1-yl)propyl]cyclobutanecarboxamide;
N-[1(S)-1-(3-fluorophenyl)-3-(4-[3-benzyl-1-ethyl(1H-pyrazol-5-yl]piperidin-1-yl)propyl]cyclobutanecarboxamide;
N-[1(S)-1-(3-fluorophenyl)-3-(4-[1,3-diethyl-5-methyl(1H-pyrazol-4-yl]piperidin-1-yl)propyl]cyclobutanecarboxamide;

and pharmaceutically acceptable salts thereof.

The subject compounds are useful in a method of modulating (e.g., inhibiting) CCR5 chemokine receptor activity in a patient in need of such modulation (e.g., inhibition) comprising the administration of an effective amount of the compound.

The present invention is directed to the use of the foregoing compounds as modulators (e.g., inhibitors) of CCR5 chemokine receptor activity.

The utility of the compounds in accordance with the present invention as modulators of CCR5 chemokine receptor activity may be demonstrated by methodology known in the art, such as the assay for chemokine binding as disclosed by Van Riper, et al., *J. Exp. Med.*, 177, 851–856 (1993) which may be readily adapted for measurement of CCR5 binding. Cell lines for expressing the receptor of interest include those naturally expressing the receptor, such as EOL-3 or THP-1, or a cell engineered to express a recombinant receptor, such as CHO, RBL-2H3, HEK-293. The utility of the compounds in accordance with the present invention as inhibitors of the spread of HIV infection in cells may be demonstrated by methodology known in the art, such as the HIV quantitation assay disclosed by Nunberg, et al., *J. Virology*, 65 (9), 4887–4892 (1991).

In particular, the compounds of the following examples had activity in binding to the CCR5 receptor in the aforementioned assays, generally with an $IC_{50}$ of less than about 5 μM. Such a result is indicative of the intrinsic activity of the compounds in use as modulators of CCR5 chemokine receptor activity.

Mammalian chemokine receptors provide a target for interfering with or promoting eosinophil and/or lymphocyte function in a mammal, such as a human. Compounds which inhibit or promote chemokine receptor function, are particularly useful for modulating eosinophil and/or lymphocyte function for therapeutic purposes. Accordingly, the present invention is directed to compounds which are useful in the prevention and/or treatment of a wide variety of inflammatory and immunoregulatory disorders and diseases, allergic diseases, atopic conditions including allergic rhinitis, dermatitis, conjunctivitis, and asthma, as well as autoimmune pathologies such as rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation. As a result, one or more inflammatory processes, such as leukocyte emigration, chemotaxis, exocytosis (e.g., of enzymes, histamine) or inflammatory mediator release, is inhibited. For example, eosinophilic infiltration to inflammatory sites (e.g., in asthma) can be inhibited according to the present method.

Similarly, an instant compound which promotes one or more functions of a mammalian chemokine receptor (e.g., a human chemokine) is administered to stimulate (induce or enhance) an inflammatory response, such as leukocyte emigration, chemotaxis, exocytosis (e.g., of enzymes, histamine) or inflammatory mediator release, resulting in the beneficial stimulation of inflammatory processes. For example, eosinophils can be recruited to combat parasitic infections.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

Diseases and conditions associated with inflammation and infection can be treated using the method of the present invention. In a preferred embodiment, the disease or condition is one in which the actions of eosinophils and/or lymphocytes are to be inhibited or promoted, in order to modulate the inflammatory response.

Diseases or conditions of humans or other species which can be treated with inhibitors of chemokine receptor function, include, but are not limited to: inflammatory or allergic diseases and conditions, including respiratory allergic diseases such as asthma, particularly bronchial asthma, allergic rhinitis, hypersensitivity lung diseases, hypersensitivity pneumonitis, eosinophilic pneumonias (e.g., Loeffler's syndrome, chronic eosinophilic pneumonia), delayed-type hypersentitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such an dermatitis, eczema, atopic dermatitis, allergic contact dermatitis, urticaria; vasculitis (e.g., necrotizing, cutaneous, and hypersensitivity vasculitis); eosinphilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, dermatomyositis.

Diseases or conditions of humans or other species which can be treated with promoters of chemokine receptor function, include, but are not limited to: immunosuppression, such as that in individuals with immunodeficiency syndromes such as AIDS, individuals undergoing radiation therapy, chemotherapy, therapy for autoimmune disease or other drug therapy (e.g., corticosteroid therapy), which causes immunosuppression; immunosuppression due congenital deficiency in receptor function or other causes; and infectious diseases, such as parasitic diseases, including, but not limited to helminth infections, such as nematodes (round worms); (Trichuriasis, Enterobiasis, Ascariasis, Hookworm, Strongyloidiasis, Trichinosis, filariasis); trematodes (flukes) (Schistosomiasis, Clonorchiasis), cestodes (tape worms) (Echinococcosis, *Taeniasis saginata,* Cysticercosis); visceral worms, visceral larva migrans (e.g., Toxocara), eosinophilic gastroenteritis (e.g., Anisaki spp., Phocanema ssp.), cutaneous larva migrans (*Ancylostona braziliense, Ancylostoma caninum*).

The compounds of the present invention are accordingly useful in the prevention and treatment of a wide variety of inflammatory and immunoregulatory disorders and diseases, allergic conditions, atopic conditions, as well as autoimmune pathologies.

In another aspect, the instant invention may be used to evaluate putative specific agonists or antagonists of CCR5 chemokine receptors. Accordingly, the present invention is directed to the use of these compounds in the preparation and execution of screening assays for compounds which modulate the activity of CCR5 chemokine receptors. For example, the compounds of this invention are useful for isolating receptor mutants, which are excellent screening tools for more potent compounds. Furthermore, the compounds of this invention are useful in establishing or determining the binding site of other compounds to chemokine receptors, e.g., by competitive inhibition. The compounds of the instant invention are also useful for the evaluation of putative specific modulators of the CCR5 chemokine receptors. As appreciated in the art, thorough evaluation of specific agonists and antagonists of the above chemokine receptors has been hampered by the lack of availability of non-peptidyl (metabolically resistant) compounds with high binding affinity for these receptors. Thus the compounds of this invention are commercial products to be sold for these purposes.

The present invention is further directed to a method for the manufacture of a medicament for modulating CCR5 chemokine receptor activity in humans and animals comprising combining a compound of the present invention with a pharmaceutical carrier or diluent.

The present invention is further directed to the use of these compounds in the prevention or treatment of infection by a retrovirus, in particular, the human immunodeficiency virus (HIV) and the treatment of, and delaying of the onset of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by, e.g., blood transfusion, organ transplant, exchange of body fluids, bites, accidental needle stick, or exposure to patient blood during surgery.

In an aspect of the present invention, a subject compound may be used in a method of inhibiting the binding of a chemokine to a CCR5 chemokine receptor of a target cell, which comprises contacting the target cell with an amount of the compound which is effective at inhibiting the binding of the chemokine to the CCR5 chemokine receptor.

The subject treated in the methods above is a mammal, preferably a human being, male or female, in whom modulation of CCR5 chemokine receptor activity is desired. "Modulation" as used herein is intended to encompass antagonism, agonism, partial antagonism, inverse agonism and/or partial agonism. In an aspect of the present invention, modulation refers to antagonism of CCR5 chemokine receptor activity. The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention to the individual in need of treatment.

The term "subject," (alternatively referred to herein as "patient") as used herein refers to an animal, preferably a mammal, most preferably a human, who has been the object of treatment, observation or experiment.

Combined therapy to modulate CCR5 chemokine receptor activity and thereby prevent and treat inflammatory and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities.

For example, in the treatment or prevention of inflammation, the present compounds may be used in conjunction with an antiinflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, asprin, codiene, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antiitussive such as codeine, hydrocodone, caramiphen, carbetapentane, or dextramethorphan; a diuretic; and a sedating or non-sedating antihistamine. Likewise, compounds of the present invention may be used in combination with other drugs that are used in the treatment/prevention/suppression or amelioration of the diseases or conditions for which compounds of the pressent invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention. Examples of other active ingredients that may be combined with a compound of the present invention, either administered separately or in the same pharmaceutical compositions, include, but are not limited to: (a) VLA-4 antagonists such as those described in U.S. Pat. No. 5,510,332, WO95/15973, WO96/01644, WO96/06108, WO96/20216, WO96/22966, WO96/31206, WO96/40781, WO97/03094, WO97/02289, WO98/42656, WO98/53814, WO98/53817, WO98/53818, WO98/54207, and WO98/58902; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (HI-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as β2-agonists (terbutaline, metaproterenol, fenoterol, isoetharine, albuterol, bitolterol, and pirbuterol), theophylline, cromolyn sodium, atropine, ipratropium bromide, leukotriene antagonists (zafirlukast, montelukast, pranlukast, iralukast, pobilukast, SKB-106,203), leukotriene biosynthesis inhibitors (zileuton, BAY-1005); (f) non-steroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (i) other antagonists of the chemokine receptors, especially CXCR-4, CCR1, CCR2, CCR3 and CCR5; (j) cholesterol lowering agents such as HMG-CoA reductase inhibitors (lovastatin, simvastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (k) anti-diabetic agents such as insulin, sulfonylureas, biguanides (metformin), α-glucosidase inhibitors (acarbose) and glitazones (troglitazone and pioglitazone); (l) preparations of interferon beta (interferon beta-1α, interferon beta-1β); (m) other compounds such as 5-aminosalicylic acid and prodrugs thereof, antimetabolites such as azathioprine and 6-mercaptopurine, and cytotoxic cancer chemotherapeutic agents. The weight ratio of the compound of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

The present invention is further directed to combinations of the present compounds with one or more agents useful in the prevention or treatment of AIDS. For example, the compounds of this invention may be effectively administered, whether at periods of pre-exposure and/or post-exposure, in combination with effective amounts of the antiviral agents, immunomodulators, anti-infectives, or vaccines suitable for treating HIV infection and AIDS, and known to those of ordinary skill in the art, including those listed in the following Table.

| Drug Name | Manufacturer | Indication |
|---|---|---|
| ANTIVIRALS | | |
| Amprenavir 141 W94 GW 141 | Glaxo Wellcome | HIV infection, AIDS, ARC (protease inhibitor) |
| Abacavir GW 1592 1592U89 | Glaxo Welcome | HIV infection, AIDS, ARC (reverse transcriptase inhibitor) |
| Acemannan | Carrington Labs (Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil AL-721 | Gilead Sciences Ethigen (Los Angeles, CA) | HIV infection ARC, PGL, HIV positive, AIDS |
| Alpha Interferon | Glaxo Wellcome | Kaposi's sarcoma, HIV, in combination w/Retrovir |
| Ansamycin LM 427 | Adria Laboratories (Dublin, OH) Erbamont (Stamford, CT) | ARC |
| Antibody which neutralizes pH labile alpha aberrant Interferon | Advanced Biotherapy Concepts (Rockville, MD) | AIDS, ARC |
| AR177 | Aronex Pharm | HIV infection, AIDS, ARC |
| beta-fluoro-ddA | Nat'l Cancer Institute | AIDS-associated diseases |
| BMS-232623 (CGP-73547) | Bristol-Myers Squibb/ Novartis | HIV infection, AIDS, ARC (protease inhibitor) |
| BMS-234475 (CGP-61755) | Bristol-Myers Squibb/ Novartis | HIV infection, AIDS, ARC (protease inhibitor) |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus immune globin | MedImmune | CMV retinitis |
| Cytovene Ganciclovir | Syntex | sight threatening CMV peripheral CMV retinitis |

-continued

| Drug Name | Manufacturer | Indication |
|---|---|---|
| Delaviridine | Pharmacia-Upjohn | HIV infection, AIDS, ARC (protease inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| mozenavir (DMP-450) | AVID (Camden, NJ) | HIV infection, AIDS, ARC (protease inhibitor) |
| EL10 | Elan Corp, PLC (Gainesville, GA) | HIV infection |
| Efavirenz (DMP 266) (−)6-Chloro-4(S)- cyclopropylethynyl- 4(S)-trifluoro-methyl- 1,4-dihydro-2H-3,1- benzoxazin-2-one, | DuPont (SUSTIVA ®), Merck (STOCRIN ®) | HIV infection, AIDS, ARC (non-nucleoside RT inhibitor) |
| Famciclovir | Smith Kline | herpes zoster, herpes simplex |
| FTC | Emory University | HIV infection, AIDS, ARC (reverse transcriptase inhibitor) |
| GS 840 | Gilead | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| Compound A | Merck | HIV infection, AIDS, ARC, asymptomatic HIV positive |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (protease inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston TX) | HIV infection, AIDS, ARC |
| Ritonavir (ABT-538) | Abbott | HIV infection, AIDS, ARC (protease inhibitor) |
| Saquinavir | Hoffmann-LaRoche | HIV infection, AIDS, ARC (protease inhibitor) |
| Stavudine; d4T | Bristol-Myers Squibb | HIV infection, AIDS, |

-continued

| Drug Name | Manufacturer | Indication |
|---|---|---|
| Didehydrodeoxy-thymidine | | ARC |
| Valaciclovir | Glaxo Wellcome | genital HSV & CMV infections |
| Virazole Ribavirin | Viratek/ICN (Costa Mesa, CA) | asymptomatic HIV positive, LAS, ARC |
| VX-478 | Vertex | HIV infection, AIDS, ARC |
| Zalcitabine | Hoffmann-La Roche | HIV infection, AIDS, ARC, with AZT |
| Zidovudine; AZT | Glaxo Wellcome | HIV infection, AIDS, ARC, Kaposi's sarcoma in combination with other therapies (reverse transcriptase inhibitor) |
| ABT-378; Lopinavir | Abbott | HIV infection, AIDS, ARC (protease inhibitor) |
| ABT-378/r; contains lopinavir and ritonavir; Kaletra | Abbott | HIV infection, AIDS, ARC (protease inhibitor) |
| JE2147/AG1776 | Agouron | HIV infection, AIDS, ARC (protease inhibitor) |
| T-20 | Trimeris | HIV infection, AIDS, ARC (fusion inhibitor) |
| T-1249 | Trimeris | HIV infection, AIDS, ARC (fusion inhibitor) |
| atazanavir (BMS 232632) | Bristol Myers-Squibb | HIV infection, AIDS, ARC (protease inhibitor) |
| PRO 542 | Progenics | HIV infection, AIDS, ARC (attachment inhibitor) |
| PRO 140 | Progenics | HIV infection, AIDS, ARC (CCR5 co-receptor inhibitor) |
| TAK-779 | Takeda | HIV infection, AIDS, ARC (injectable CCR5 receptor antagonist) |
| DPC 681 & DPC 684 | DuPont | HIV infection, AIDS, ARC (protease inhibitors) |
| DPC 961 & DPC 083 | DuPont | HIV infection AIDS, ARC (nonnucleoside reverse transcriptase inhibitors) |
| Trizivir (contains abacavir, lamivudine, and zidovudine) | GlaxoSmithKline | HIV infection, AIDS, ARC (reverse transcriptase inhibitors) |
| tipranavir (PNU-140690) | Boehringer Ingelheim (purchased from Pharmacia & Upjohn) | HIV infection, AIDS, ARC (protease inhibitor) |
| tenofovir disoproxil fumarate | Gilead | HIV infection, AIDS, ARC (reverse transcriptase inhibitor) |
| TMC-120 & TMC-125 | Tibotec | HIV infections, AIDS, ARC (non-nucleoside reverse transcriptase inhibitors) |
| TMC-126 | Tibotec | HIV infection, AIDS, ARC (protease inhibitor) |
| IMMUNO-MODULATORS | | |
| AS-101 | Wyeth-Ayerst | AIDS |
| Bropirimine | Pharmacia Upjohn | advanced AIDS |
| Acemannan | Carrington Labs, Inc. (Irving, TX) | AIDS, ARC |
| CL246,738 | American Cyanamid Lederle Labs | AIDS, Kaposi's sarcoma |
| EL10 | Elan Corp, PLC (Gainesville, GA) | HIV infection |
| FP-21399 | Fuki ImmunoPharm | blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoeschst-Roussel Immunex | AIDS |
| Granulocyte Macrophage Colony Stimulating Factor | Schering-Plough | AIDS, combination w/AZT |
| HIV Core Particle Immunostimulant | Rorer | seropositive HIV |
| IL-2 Interleukin-2 | Cetus | AIDS, in combination w/AZT |
| IL-2 Interleukin-2 | Hoffman-La Roche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma, AIDS, ARC, in combination w/AZT |
| SK&F106528 Soluble T4 | Smith Kline | HIV infection |
| Thymopentin | Immunobiology Research Institute | HIV infection |
| Tumor Necrosis Factor; TNF | Genentech | ARC, in combination w/gamma Interferon |
| etanercept | Immunex Corp (Enbrel ®) | rheumatoid arthritis |
| infliximab | Centocor (Remicade ®) | rheumatoid arthritis and Crohn's disease |
| ANTI-INFECTIVES | | |
| Clindamycin with Primaquine | Pharmacia Upjohn | PCP |
| Fluconazole | Pfizer | cryptococcal meningitis, candidiasis |
| Pastille Nystatin Pastille | Squibb Corp. | prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | antibacterial |
| Trimethoprim/sulfa | | antibacterial |
| Piritrexim | Burroughs Wellcome | PCP treatment |
| Pentamidine isethionate for inhalation | Fisons Corporation | PCP prophylaxis |

-continued

| Drug Name | Manufacturer | Indication |
| --- | --- | --- |
| Spiramycin | Rhone-Poulenc | cryptosporidia diarrhea |
| Intraconazole-R51211 | Janssen Pharm. | histoplasmosis; cryptococcal meningitis |
| Trimetrexate | Warner-Lambert | PCP |
| OTHER | | |
| Daunorubicin | NeXstar, Sequus | Karposi's sarcoma |
| Recombinant Human Erythropoietin | Ortho Pharm. Corp. | severe anemia assoc. with AZT therapy |
| Recombinant Human Growth Hormone | Serono | AIDS-related wasting, cachexia |
| Leukotriene B4 Receptor Antagonist | — | HIV infection |
| Megestrol Acetate | Bristol-Myers Squibb | treatment of anorexia assoc. w/AIDS |
| Soluble CD4 Protein and Derivatives | — | HIV infection |
| Testosterone | Alza, Smith Kline | AIDS-related wasting |
| Total Enteral Nutrition | Norwich Eaton Pharmaceuticals | diarrhea and malabsorption, related to AIDS |

It will be understood that the scope of combinations of the compounds of this invention with HIV/AIDS antivirals, immunomodulators, anti-infectives or vaccines is not limited to the list in the above Table, but includes in principle any combination with any pharmaceutical composition useful for the treatment of HIV infection or AIDS. When employed in combination with the compounds of the invention, the HIV/AIDS antivirals and other agents are typically employed in their conventional dosage ranges and regimens as reported in the art, including the dosages described in the *Physicians' Desk Reference*, 54$^{th}$ edition, Medical Economics Company, 2000. The dosage ranges for a compound of the invention in these combinations are the same as those set forth above just before the above Table.

Preferred combinations are simultaneous or alternating treatments with a compound of the present invention and an inhibitor of HIV protease and/or a non-nucleoside inhibitor of HIV reverse transcriptase. An optional fourth component in the combination is a nucleoside inhibitor of HIV reverse transcriptase, such as AZT, 3TC, ddC or ddI. Preferred agents for combination therapy include: Zidovudine, Lamivudine, Stavudine, Efavirenz, Ritonavir, Nelfinavir, Abacavir, Indinavir, 141-W94 (4-amino-N-((2 syn,3S)-2-hydroxy-4-phenyl-3-((S)-tetrahydrofuran-3-yloxycarbonylamino)-butyl)-N-isobutyl-benzenesulfonamide), N-(2(R)-hydroxy-1(S)-indanyl)-2(R)-phenylmethyl-4-(S)-hydroxy-5-(1-(4-(2-benzo[b]furanylmethyl)-2(S)-N'(t-butylcarbox-amido)-piperazinyl))-pentaneamide, and Delavirdine. A preferred inhibitor of HIV protease is indinavir, which is the sulfate salt of N-(2(R)-hydroxy-1(S)-indanyl)-2(R)-phenylmethyl-4-(S)-hydroxy-5-(1-(4-(3-pyridyl-methyl)-2(S)-N'-(t-butylcarbo-xamido)-piperazinyl))-pentane-amide ethanolate, and is synthesized according to U.S. Pat. No. 5,413,999. Indinavir is generally administered at a dosage of 800 mg three times a day. Other preferred inhibitors of HIV protease include nelfinavir and ritonavir. Preferred non-nucleoside inhibitors of HIV reverse transcriptase include (−) 6-chloro-4(S)-cyclopropylethynyl-4(S)-trifluoromethyl-1,4-dihydro-2H-3,1-benzoxazin-2-one, which may be prepared by methods disclosed in EP 0,582,455. The preparation of ddC, ddI and AZT are also described in EPO 0,484,071. These combinations may have unexpected effects on limiting the spread and degree of infection of HIV. Preferred combinations with the compounds of the present invention include the following: (1) Zidovudine and Lamivudine; (2) Stavudine and Lamivudine; (3) Efavirenz; (4) Ritoavir; (5) Nelfinavir; (6) Abacavir; (7) Indinavir; (8) 141-W94; and (9) Delavirdine. Preferred combinations with the compounds of the present invention further include the following (1) indinavir, with efavirenz or (−) 6-chloro-4(S)-cyclopropylethynyl-4(S)-trifluoromethyl-1,4-dihydro-2H-3,1-benzoxazin-2-one, and, optionally, AZT and/or 3TC and/or ddI and/or ddC; (2) indinavir, and any of AZT and/or ddI and/or ddC.

Compound A in the foregoing Table is N-(2(R)-hydroxy-1(S)-indanyl)-2(R)-phenylmethyl-4(S)-hydroxy-5-(1-(4-(2-benzo[b]furanylmethyl)-2(S)-N'-(t-butylcarboxamido)-piperazinyl))pentaneamide, preferably administered as the sulfate salt. Compound A can be prepared as described in U.S. Pat. No. 5,646,148.

In such combinations the compound of the present invention and other active agents may be administered separately or in conjunction. In addition, the administration of one element may be prior to, concurrent to, or subsequent to the administration of other agent(s).

The compounds of the present invention may be administered in the form of pharmaceutically acceptable salts. The term "pharmaceutically acceptable salt" is intended to include all acceptable salts such as acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, panoate, valerate, and the like which can be used as a dosage form for modifying the solubility or hydrolysis characteristics or can be used in sustained release or pro-drug formulations. Depending on the particular functionality of the compound of the present invention, pharmaceutically acceptable salts of the compounds of this invention include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylene-diamine, chloroprocaine, diethanolamine, procaine, N-benzylphenethyl-amine, diethylamine, piperazine, tris(hydroxymethyl)aminomethane, and tetramethylammonium hydroxide. These salts may be prepared by standard procedures, e.g. by reacting a free acid with a suitable organic or inorganic base. Where a basic group is present, such as amino, an acidic salt, i.e. hydrochloride, hydrobromide, acetate, pamoate, and the like, can be used as the dosage form.

Also, in the case of an acid (—COOH) or alcohol group being present, pharmaceutically acceptable esters can be employed, e.g. acetate, maleate, pivaloyloxymethyl, and the like, and those esters known in the art for modifying solubility or hydrolysis characteristics for use as sustained release or prodrug formulations.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally- occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouthwashes and gargles.)

The pharmaceutical composition and method of the present invention may further comprise other therapeutically active compounds as noted herein which are usually applied in the treatment of the above mentioned pathological conditions.

In the treatment or prevention of conditions which require chemokine receptor modulation an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Abbreviations used in the instant specification, particularly the Schemes and Examples, include the following:

Ac=acetyl
9-BBN=9-borabicyclo[3.3.1]nonane
Bn=benzyl
BOC or Boc=t-butyloxycarbonyl
Bu=butyl
t-Bu=tert-butyl
CBZ=carbobenzoxy (alternatively, benzyloxycarbonyl)
CDI=carbonyl diimidazole
DAST=(diethylamino)sulfur trifluoride
DCC=dicyclohexyl carbodiimide
DCM=dichloromethane
DIBAL=diisobutylaluminum hydride
DIEA or DIPEA=diisopropylethylamine
DIAD=diisopropylazodicarboxylate
DMF=N,N-dimethylformamide
DMSO=dimethylsulfoxide
EDAC=1-(3-dimethylamino)propyl-3-ethylcarbodiimide
Et=ethyl
ether=diethyl ether
h=hour(s)
HMDS=hexamethyldisilazyl
HOBT or HOBt=1-hydroxy benzotriazole hydrate
KHMDS=potassium hexamethyldisilazide
LDA=lithium diisopropylamide
Me=methyl
m=minute(s)
Ph=phenyl
Pr=propyl
i-Pr=isopropyl
PMB=p-methoxybenzyl
sat'd=saturated aqueous
rt=room temperature
TBSO=t-butyldimethylsiloxy
TEA=triethylamine
Tf=triflic or triflate
TFA=trifluoroacetic acid
THF=tetrahydrofuran
TPAP=tetrapropylammonium perruthenate The compounds of the present invention can be readily prepared according to the following reaction schemes and examples, or modifications thereof. Starting materials can be made from procedures known in the art or as illustrated. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Unless otherwise indicated, the variables are as defined above.

SCHEME 1

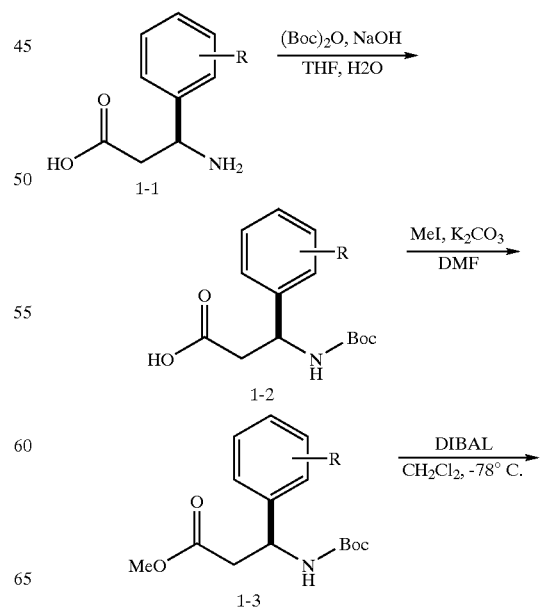

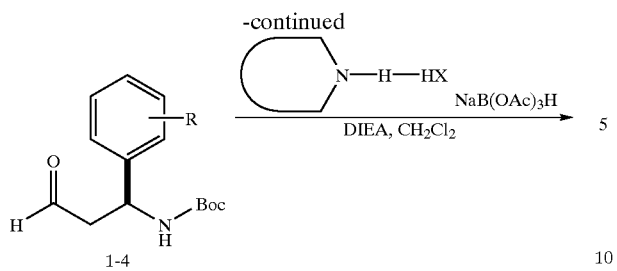

SCHEME 2

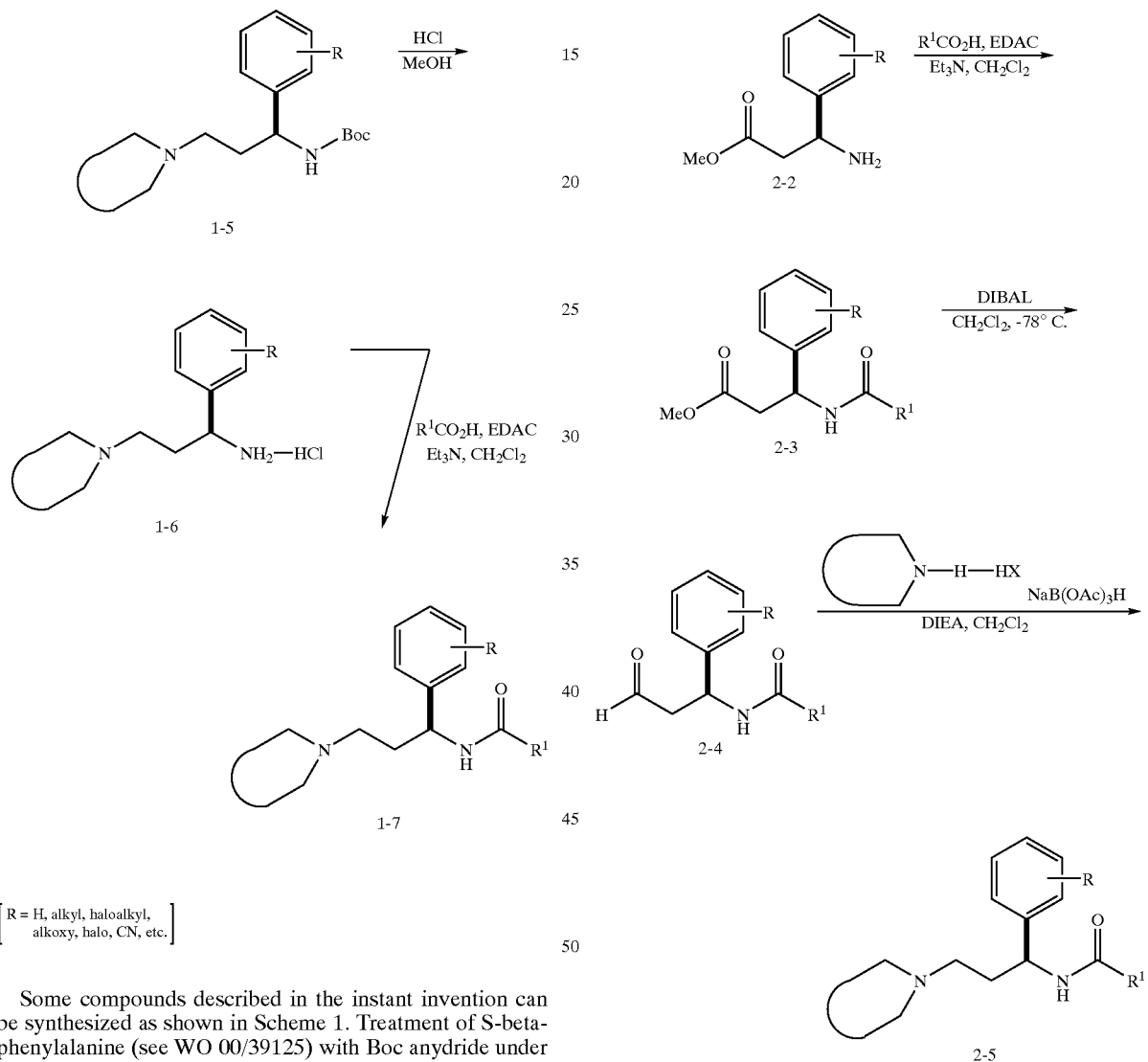

[R = H, alkyl, haloalkyl, alkoxy, halo, CN, etc.]

Some compounds described in the instant invention can be synthesized as shown in Scheme 1. Treatment of S-beta-phenylalanine (see WO 00/39125) with Boc anydride under basic conditions in TBF/water provides the protected derivative 1-2. Esterification with methyl iodide and potassium carbonate in DMF affords ester 1-3. Reduction of 1-3 with DIBAL at low temperature in methylene chloride affords aldehyde 1-4, which can be reductively aminated with a suitable secondary amine with sodium cyanoborohydride or triacetoxyborohydride in methylene chloride, to yield tertiary amine 1-5. Removal of the Boc group under acidic conditions, for example with hydrochloric acid in methanol, affords primary amine 1-6. Acylation with a suitable carboxylic acid utilizing EDAC (1-(3-dimethylamino)propyl-3-ethylcarbodiimide) and a tertiary amine base in dichloromethane then provides the desired compound 1-7.

Another route to compounds described in the instant invention is shown in Scheme 2. Treatment of 1-3 with HCl in methanol provides ester 2-2. Coupling of the primary amine of 2-2 with a suitable carboxylic acid in the presence of EDAC and triethylamine in methylene chloride or other suitable solvents provides ester 2-3. Reduction of 2-3 with DIBAL at low temperature affords aldehyde 2-4, which upon reductive amination under standard conditions with a suitable secondary amine yields the desired final compound 2-5.

SCHEME 3

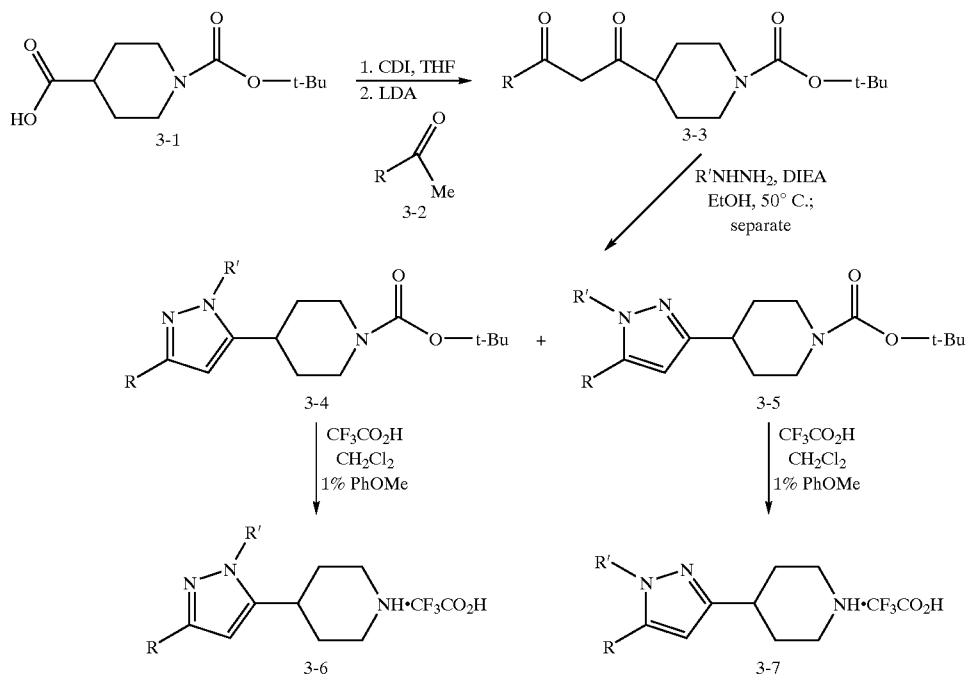

One preparation of piperidine subunits containing functionalized pyrazoles at C4 of the piperidine is given in Scheme 3. Treatment of piperidine 3-1 with carbonyldiimidazole to form the acyl imidazole, followed by enolate formation by addition of addition of lithium diisopropylamide (LDA), and then a dialkyl or alkyl-aryl ketone 3-2 gives the diketone 3-3. Treatment with a monoalkyhydrazine in an alcohol solvent at temperatures between 0 to 100 degrees C. (preferably about 50 degrees C.) optionally in the presence of a hindered base such as DIEA then provides a mixture of the isomeric pyrazoles 3-4 and 3-5. After separation of these compounds by chromatography or crystallization, the individual products are deblocked under acidic conditions (for example trifluoroacetic acid and anisole with or without methylene chloride as a cosolvent) to provide the piperidine salts 3-6 and 3-7, which are then used as the cyclic secondary amine component as shown above in Schemes 1 and 2.

SCHEME 4

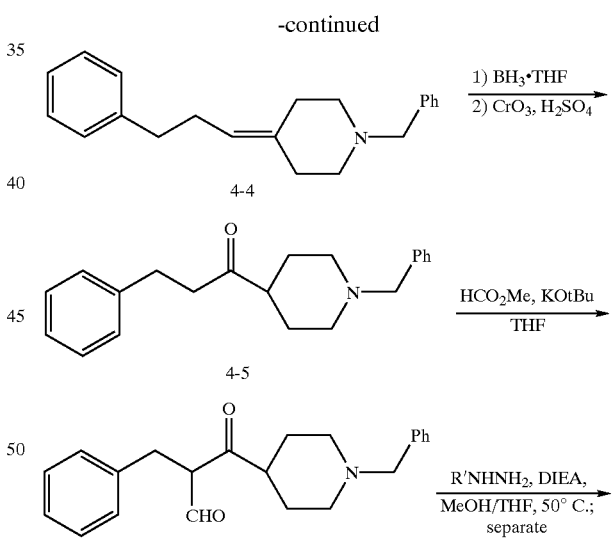

-continued

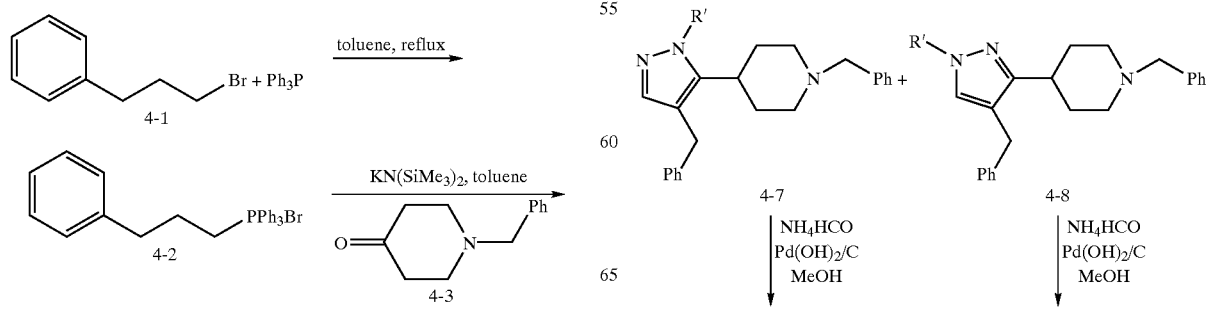

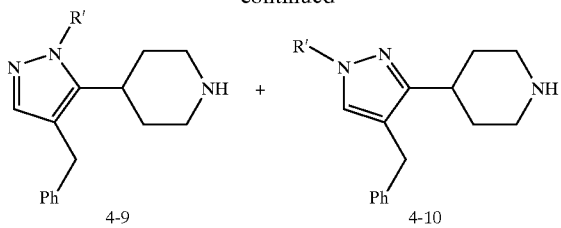

Another preparation of piperidine subunits containing functionalized pyrazoles at C4 of the piperidine is given in Scheme 4. Treatment of commercially available bromide 4-1 with triphenylphosphine in refluxing toluene provides phosphonium salt 4-2, which after treatment with a strong anhydrous base such as potassium hexamethyldisilazide in toluene and the piperidine ketone 4-3 provides the olefin 4-4. Hydroboration followed by an oxidative workup with chromic acid then affords ketone 4-5. Selective formylation of 4-5 with methyl formate in the presence of potassium t-butoxide affords ketoaldehyde 4-6. Heating of 4-6 with a monoalkylhydrazine in methanol optionally in the presence of a hindered (or insoluble) base such as DIEA then provides a mixture of the 1,5-disubstituted pyrazoles 4-7 and 4-8. After separation by chromatography, crystallization or fractional distillation, the purified isomers are deprotected under transfer hydrogenation conditions to provide the piperidines 4-9 and 4-10, which are then used as the cyclic secondary amine component as shown above in Schemes 1 and 2.

An alternate preparation of piperidine subunits containing functionalized pyrazoles at C4 of the piperidine is given in Scheme 5. Treatment of commercially available isonipecotic acid under reducing conditions with borane-THF complex provides primary alcohol 5-2. Oxidation under standard conditions, for example using Swern's conditions, yields aldehyde 5-3. Treatment of 5-3 with carbon tetrabromide in the presence of triphenylphosphine affords dibromo-olefin 5-4, which upon treatment with n-butyllithium followed by tributyl tin chloride provides stannyl acetylene 5-5. Coupling of 5-5 with an acid chloride ArCH$_2$COCl in the presence of a suitable palladium catalyst, such as dichlorobis (triphenylphosphine)palladium, in refluxing dichloromethane provided unsaturated ketone 5-6. Treatment of acetylenic ketone 5-6 with a mono-alkylhydrazine in a suitable solvent, such as ethanol, affords pyrazole 5-7. Deprotection of this compound under acidic conditions, for example with HCl in methanol or with trifluoroacetic acid in dichloromethane in the presence of anisole, provides the desired pyrazole derivative 5-8, which is then used as the cyclic secondary amine component as shown above in Schemes 1 and 2.

SCHEME 6

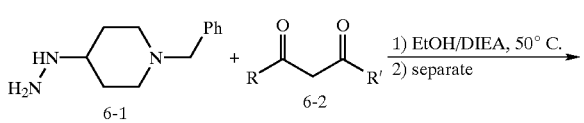

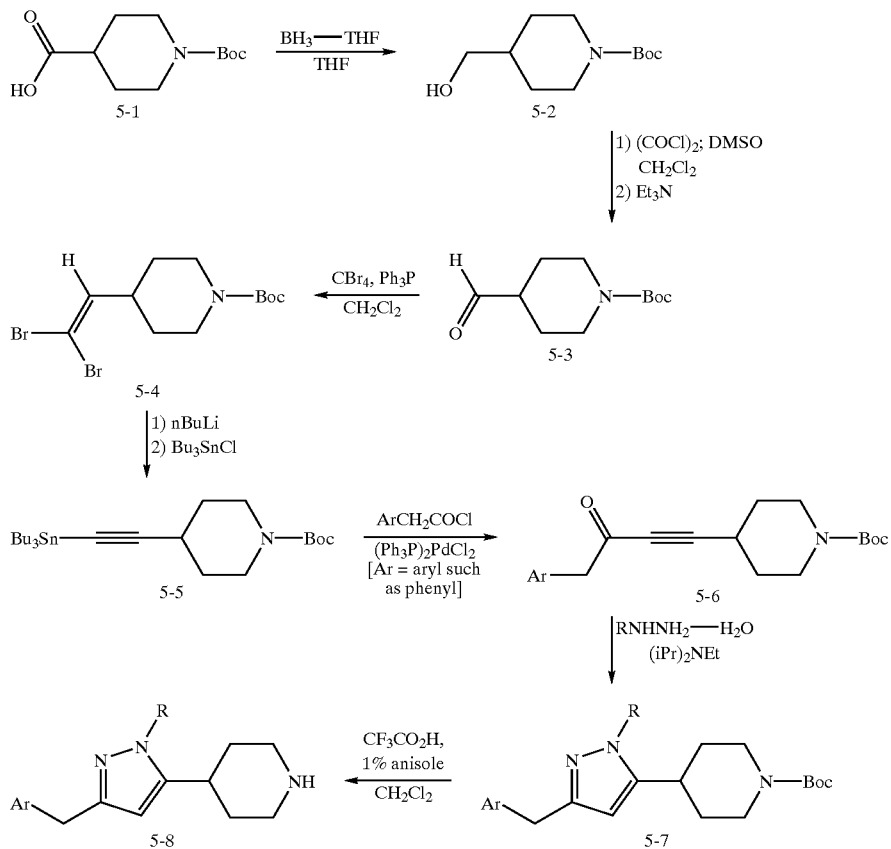

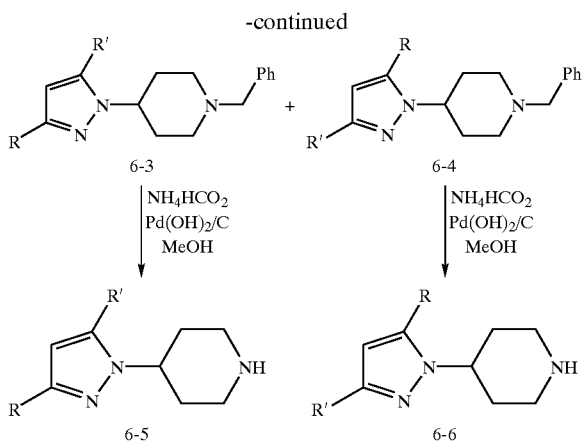

A preparation of piperidine subunits containing 3,5-difunctionalized pyrazoles linked through N1 to C4 of the piperidine is given in Scheme 6. Treatment of commercially available hydrazine 6-1 with diketone 6-2 in ethanol at 0 to 90 degrees C. (prefereably 50 degrees C.) in the presence of DIEA provides a mixture of pyrazoles 6-3 and 6-4, which are separated under standard conditions, for example HPLC. Removal of the benzyl groups by transfer hydrogenation provides the secondary piperidines 6-5 and 6-6, which are then used as the cyclic secondary amine component as shown above in 1 and 2.

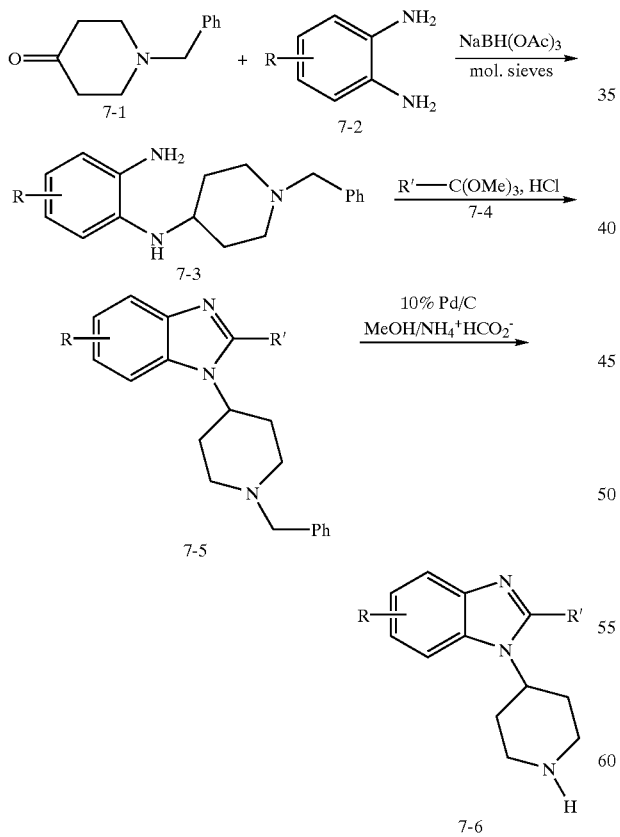

A preparation of 4-(benzimidazol-1-yl)piperidine subunits is given in Scheme 7. Combining piperidone 7-1 and diamine 7-2 in the presence of sodium triacetoxy borohydride under dehydrating conditions provides reductive amination product 7-3. Addition of a suitably substituted ortho ester 7-4 in the presence of a acid catalyst, for example concentrated hydrochloric acid, provides benzimidazole intermediate 7-5. Deprotection under reductive conditions, for example with palladium on carbon under transfer hydrogenation conditions, then provides secondary amine 7-6, which is then used as the cyclic secondary amine component as shown above in Schemes 1 and 2.

SCHEME 8

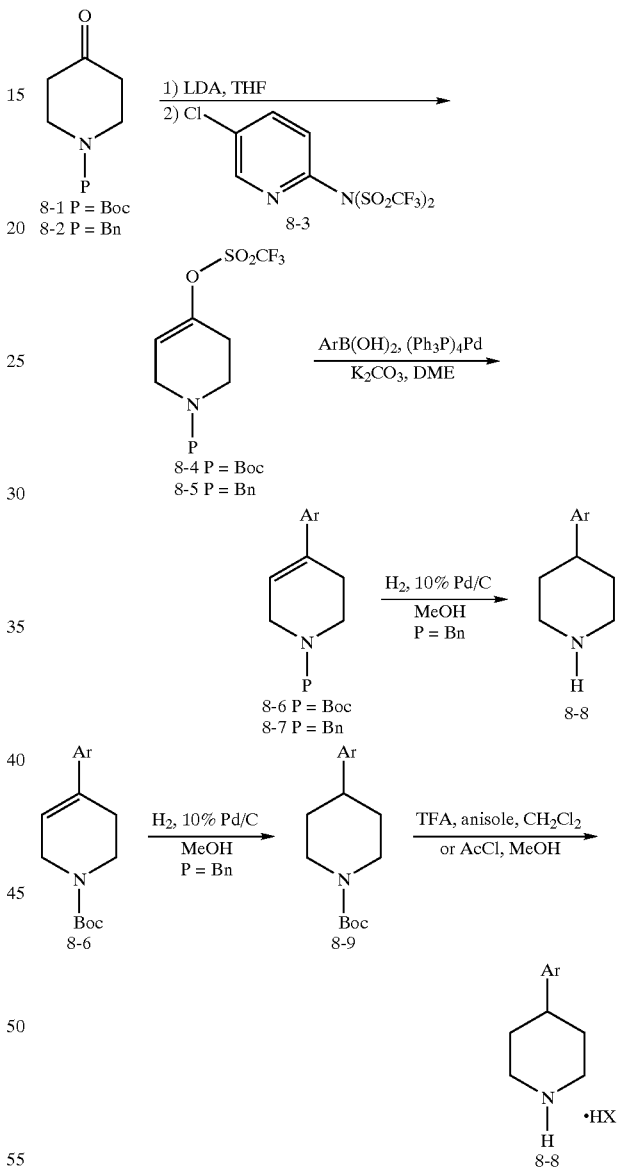

One method of generating 4-aryl piperidines as intermediates is given in Scheme 8. Reaction of commercially available 8-1 or 8-2 with a strong base, such as LDA, LiHDMS, NaHMDS, KHMDS, or NaH followed by treating with a suitable triflating agent, such as 5-chloropyrid-2-yl triflimide (8-3), N-phenyl triflimide or triflic anhydride, provides enol triflates 8-4 or 8-5. Heating with commercially available aryl boronic acids in the presence of a suitable palladium(0) catalyst such as tetrakis triphenylphosphine palladium, a base (such as potasssium carbonate or sodium carbonate), in a solvent such as DME, THF, dioxane or toluene/ethanol, effects coupling to provide the unsaturated products 8-6 or 8-7. In the case of 8-7, treatment with a heterogeneous palladium catalyst in methanol or ethanol in an atmosphere of hydrogen provides the desired intermediate 8-8. Alternatively, the Boc protected derivative 8-6 is hydrogenated under standard conditions to provided the saturated piperidine 8-9, which is then deprotected under acidic conditions (such as trifluoroacetic acid and anisole in methylene chloride), to provide 8-8 as a salt, which is then used as the cyclic secondary amine component as shown above in Schemes 1 and 2.

SCHEME 9

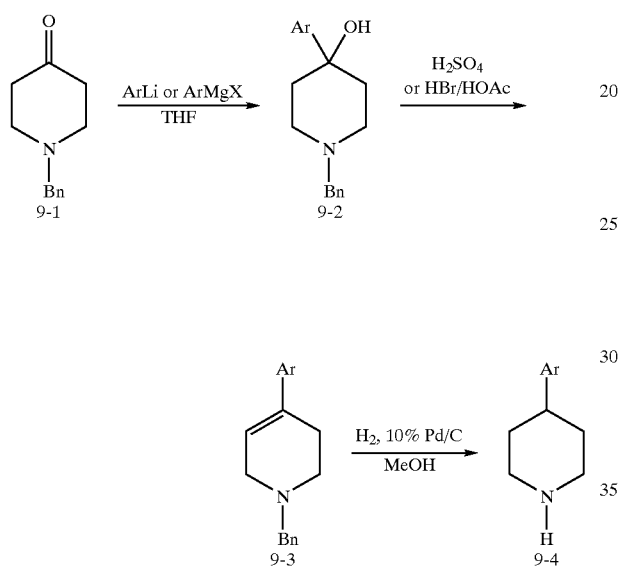

An alternative method of generating 4-aryl piperidines as intermediates is given in Scheme 9. Reaction of commercially available 9-1 with an aryl magnesium halide or with an aryllithium (in the presence or absence of anhydrous cerium trichloride) provides tertiary alcohol 9-2, which upon treatment under acidic conditions (such as sulfuric acid, HBr in acetic acid, HCl in acetic acid) or under dehydrating conditions (such as with thionyl chloride in pyridine or with phosphorus oxychloride) provides olefin 9-3. Hydrogenation under standard conditions using either hydrogen gas or a hydrogen donor (such as ammonium formate or cyclohexene) effects reduction of the double bond and cleavage of the N-benzyl group to provide the desired intermediate 9-4. Under some circumstances it may be preferable to reduce the double bond under non-hydrogenolytic conditions, for example with triethylsilane and trifluoroacetic acid or under dissolving metal conditions (for example, sodium or lithium metal in ammonia or a lower alkyl amine). If the N-benzyl group is not removed under these conditions, it may be cleaved by treatment with either vinyl chloroformate and then hydrogen chloride or by treatment with 2-chloroethyl chloroformate followed by heating in methanol. The product 9-4 is then used as the cyclic secondary amine component as shown above in Schemes 1 and 2.

SCHEME 10

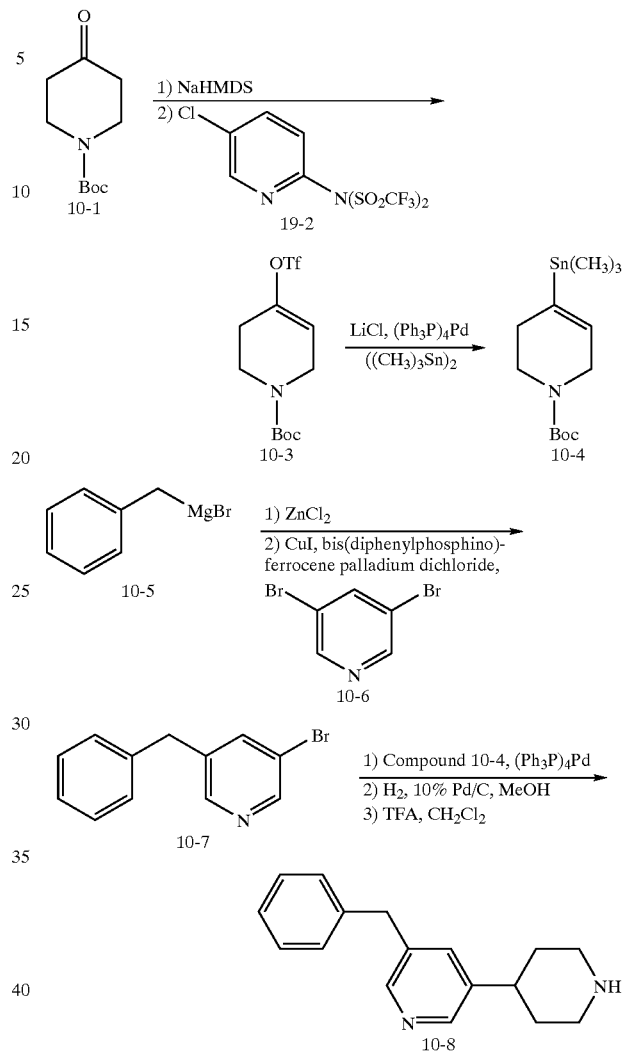

Piperidine intermediates bearing a pyridine substituent can be synthesized as shown in Scheme 10. Enolization of ketone 10-1 with a strong, non-nucleophilic base such as sodium hexamethyldisilazide, followed by treatment with a suitable triflating agent, such as 2-(N,N-bis(trifluoromethanesulfonyl)amino)-5-chloropyridine (10-2), provides vinyl triflate 10-3. Exchange of the triflate for a trimethylstannyl group is carried out under standard conditions to provide 10-4. Separately, treatment of benzyl magnesium chloride with zinc chloride, followed by treatment of the resulting material with 3,5-dibromopyridine, copper iodide and a suitable palladium catalyst, provides coupled product 10-7. Coupling of 10-4 with 10-7 in the presence of a soluble palladium catalyst, followed by hydrogenation of the double bond, and then cleavage of the Boc group under acidic conditions, then gives intermediate 10-8.

SCHEME 11

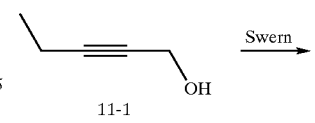

-continued

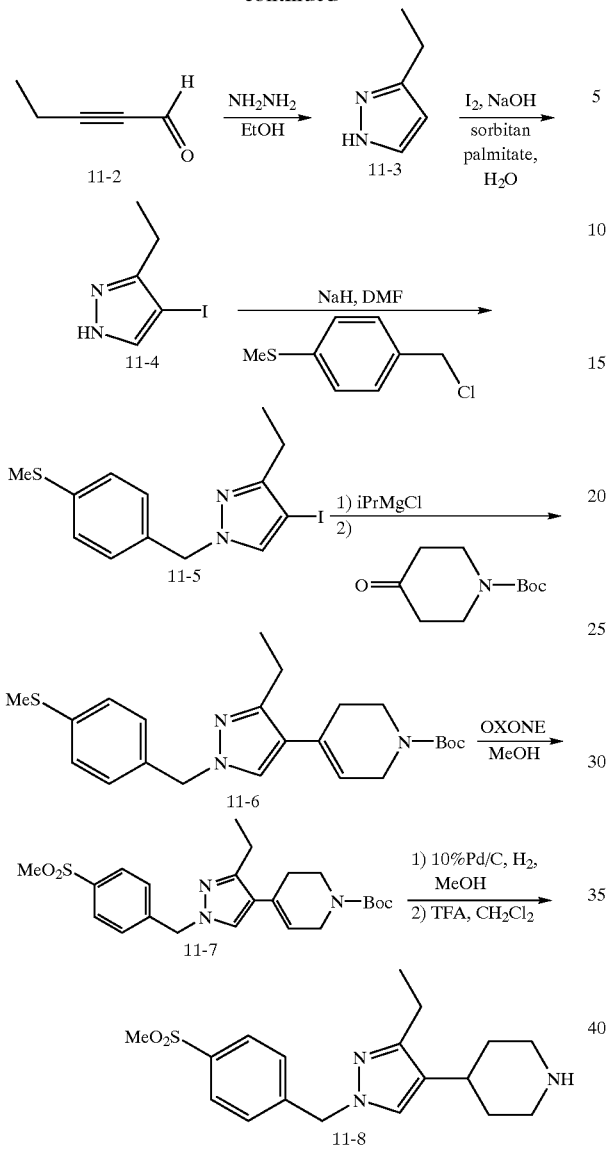

Piperidine intermediates bearing a functionalized pyrazole side chain can be prepared as shown in Scheme 11. Oxidation of 2-pentyn-1-ol under Swern conditions followed by treatment with hydrazine provides pyrazole 11-3. Iodination under phase transfer conditions affords iodopyrazole 11-4. Alkylation with 4-thiomethylbenzyl chloride yields pyrazole 11-5. Halogen-metal exchange with isopropyl magnesium chloride followed by addition of N-Boc-4-pyridone affords pyrazole 11-6, which on oxidation with Oxone® (potassium peroxymonosulfate) provides sulfone 11-7. Hydrogenation and then treatment with trifluoroacetic acid in methylene chloride then affords intermediate piperidine 11-8.

SCHEME 12

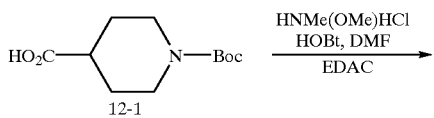

-continued

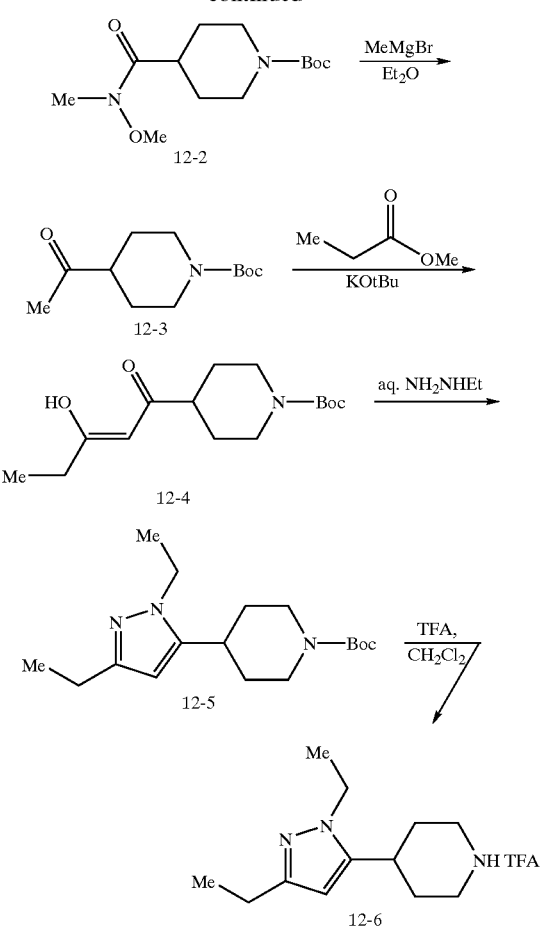

Piperidine intermediates with alkylpyrazole substituents can be prepared as shown in Scheme 12. Treatment of N-Boc4-carboxypiperidine with EDAC, HOBt and N,O-dimethylhydroxylamine hydrochloride affords amide 12-2, which upon exposure to methyl magnesium bromide provides ketone 12-3. Condensation of 12-3 with methyl propionate in the presence of potassium tert-butoxide provides diketone 12-4, which affords pyrazole 12-5 after treatment with aqueous ethylhydrazine. Deprotection under acidic conditions, for example with trifluoroacetic acid in methylene chloride., then provides intermediate 12-6.

SCHEME 13

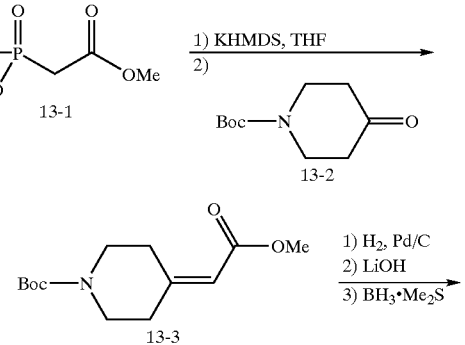

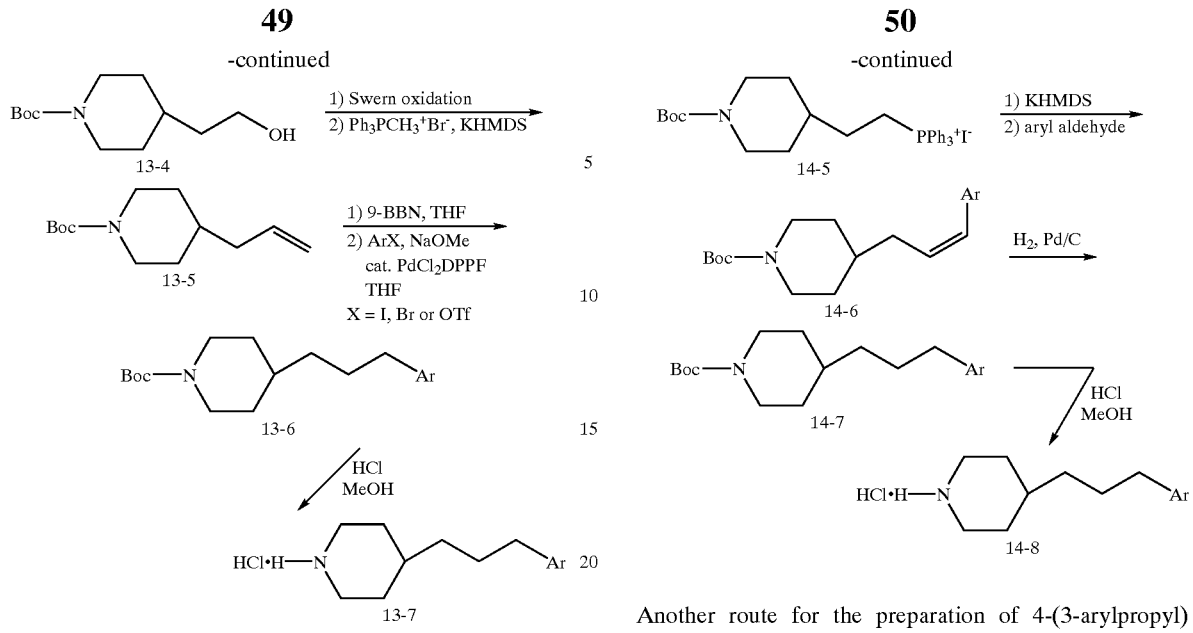

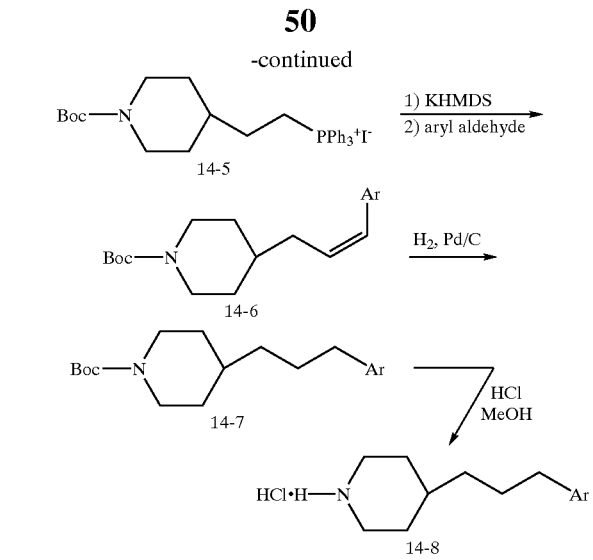

A route for the preparation of 4-(3-arylpropyl)piperidines is given in Scheme 22. Treatment of phosphonoacetate 13-1 with KHMDS followed by addition of commercially available N-Boc-4-piperidone 13-2 provides unsaturated ester 13-3. Hydrogenation of 13-3 followed by hydrolysis to the acid and then reduction with borane.methyl sulfide then affords primary alcohol 13-4. Mild oxidation of 13-4 under Swern conditions provides the corresponding aldehyde, which upon treatment with the Wittig reagent prepared from methyltriphenylphosphonium iodide and KHMDS yields olefin 13-5. Hydroboration with a dialkylborane, such as 9-borabicyclo[3.3.1]nonane (9-BBN), followed by treatment with an aryl halide (the halides preferably being bromide or iodide) or aryl triflate in the presence of a suitable soluble palladium catalyst, for example Pd(dppf)Cl$_2$, in warn to refluxing THF, provides the 3-arylpropyl derivative 14-6. Removal of the Boc group under acidic conditions, for example with HCl in methanol or with trifluoroacetic acid in methylene chloride, then affords the 1-unsubstituted piperidine 13-7, which can then be employed as the secondary amine component in the syntheses described above in Schemes 1 and 2.

Another route for the preparation of 4-(3-arylpropyl) piperidines is given in Scheme 14. Treatment of phosphonoacetate 14-1 with KHMDS followed by addition of commercially available N-Boc -4-piperidone 14-2 provides unsaturated ester 14-3. Hydrogenation of 14-3 followed by hydrolysis to the acid and then reduction with borane.methyl sulfide then affords primary alcohol 14-4. Formation of the alkyl iodide with triphenylphosphine and iodine in the presence of imidazole followed by treatment with triphenylphosphine provides phosphonium salt 14-5. Deprotonation with a suitable base, for example, KHNMDS, LiHMDS, NaHMDS, NaH, LDA, or KH affords the Wittig agent in situ, which upon treatment with a suitable aromatic aldehyde yields the unsaturated derivative 14-6. Hydrogenation under standard conditions provides 14-7, and removal of the Boc group with HCl in methanol or with other acidic conditions then provides the 1-unsubstituted piperidine 14-8, which can then be employed as the secondary amine component in the syntheses described above in Schemes 1 and 2.

SCHEME 14

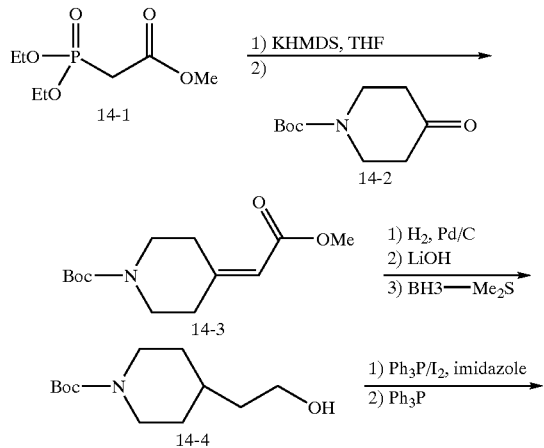

SCHEME 15

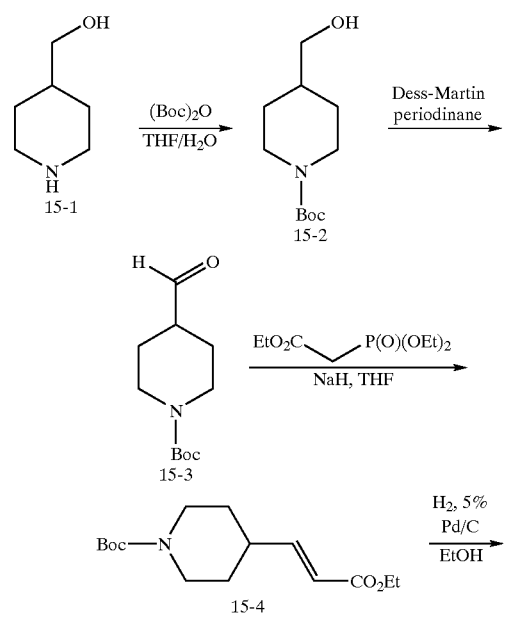

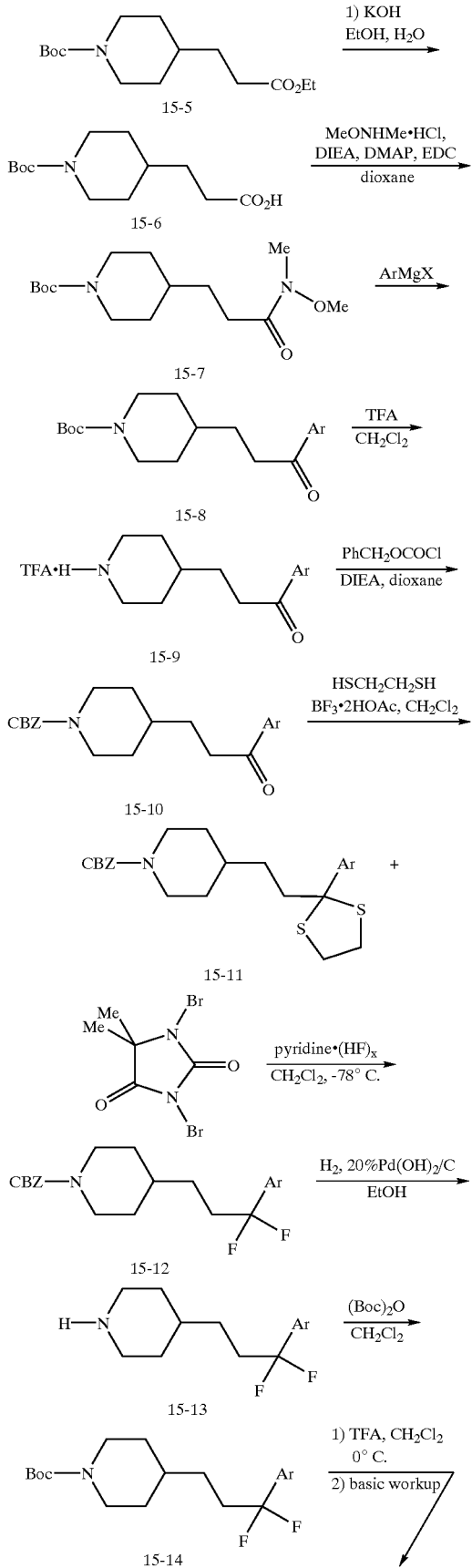
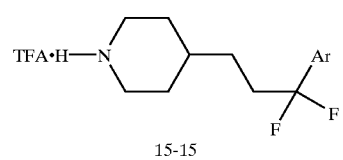

Preparation of piperidines with a 4-(3-aryl-3,3,-difluoropropyl) side chain is given in Scheme 15. Treatment of commercially available 15-1 with Boc anydride provides protected piperidine 15-2. Oxidation, for example with the Dess-Martin reagent, by a Swern oxidation, or other known methods provides aldehyde 15-3. Condensation under Horner-Wadsworth-Emmons conditions affords unsaturated ester 15-4, which is hydrogenated to ester 15-5 and then hydrolyzed to acid 15-6. Formation of the N-methyl-N-methoxy amide 15-7 is carried out employing standard activating agents such as EDC. Weinreb amide 15-7 is then allowed to react with an arylmetal reagent, such as an aryl magnesium halide or an aryllithium, to provide ketone 15-8. Cleavage of the protecting Boc group under acidic conditions yields 15-9, which is reprotected with a carbobenzyloxy group under standard conditions, to afford 15-10. Formation of dithiolane 15-11 with ethanedithiol and boron trifluoride is followed by treatment with 1,3-dibromo-3,3-dimethylhydantoin and pyridine-hydrogen fluoride complex at or around −78 degrees C., to provide gem-difluoro derivative 15-12. Removal of the CBZ group under reductive conditions provides piperidine 15-13, which may be employed directly as the secondary amine in chemistry described above. Alternatively, if additional purification is desired, 15-13 may be protected with a Boc group to afford 15-14. After suitable purification, the Boc group is removed under acidic conditions at or near 0 degrees C. A controlled, basic workup then provides 15-15, suitable for use as described above.

SCHEME 16

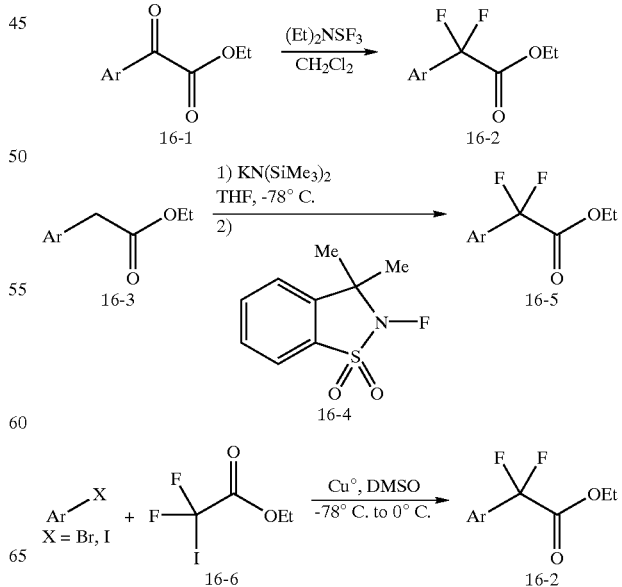

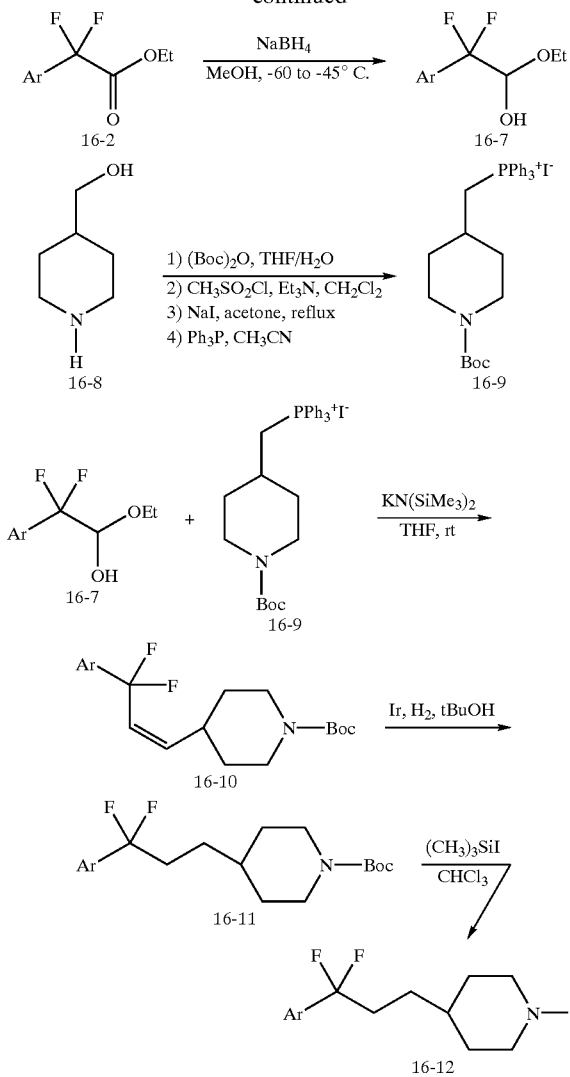

atmosphere of hydrogen, to give 16-11. Alternatively, reduction using palladium on carbon, platinum or Raney nickel in the presence of hydrogen can be used, as can diimide, which can be generated from azodicarboxylic acid in situ. The nitrogen protecting group is removed by treatment with trimethylsilyl iodide under anhydrous conditions, to afford piperidine 16-12, which is suitable for use as described above. Alternatively, the Boc group can be removed under acidic, anhydrous conditions, for example with TFA in methylene chloride or with HCl in methanol.

SCHEME 17

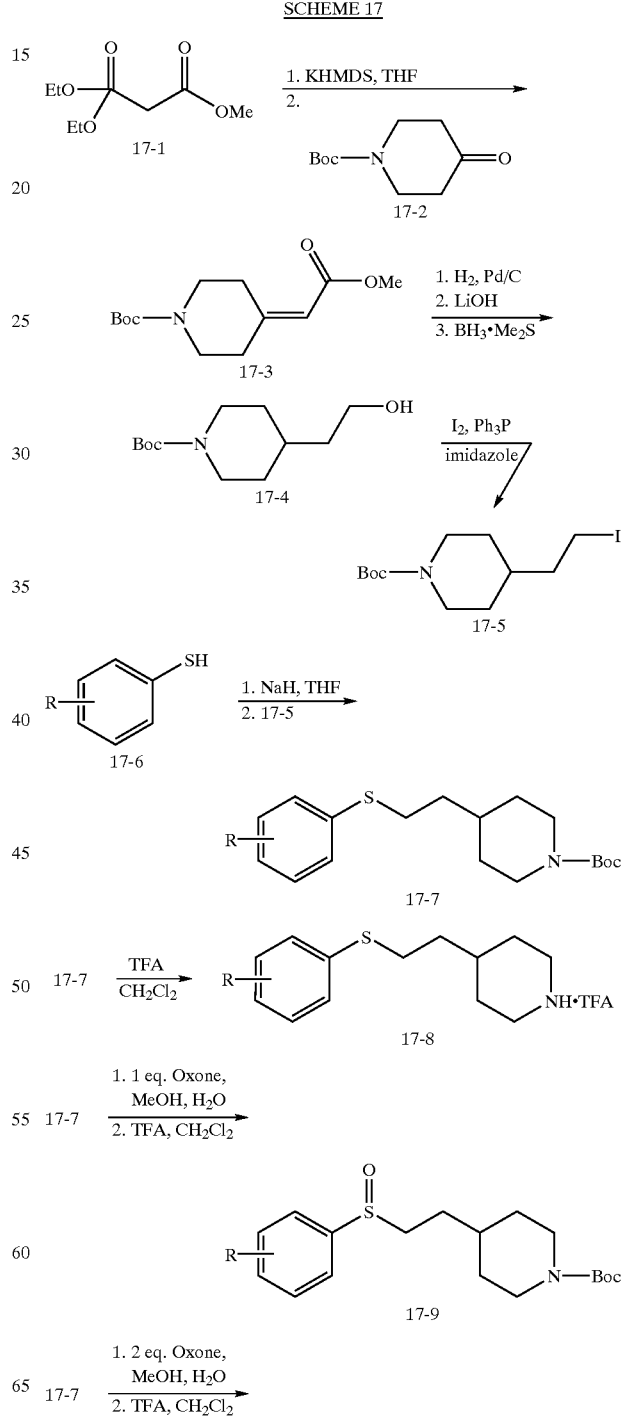

An alternate preparation of piperidines with a 4-(3-aryl-3,3,-difluoropropyl) side chain is given in Scheme 16. Preparation of the intermediate 16-2 can be accomplished in three ways. First, ketoester 16-1 can be fluorinated with diethylaminosulfur trifluoride (DAST) under standard conditions to provide α,α-difluoroester 16-2. Second, arylacetic ester 16-3 can be fluorinated by treatment with a strong base, such as potassium hexamethyldisilazide, followed by addition of a suitable fluorinating agent, such as the N-fluoro reagent 16-4, to give 16-2. Alternatively, an aryl iodide or aryl bromide 16-5 can be treated with ethyl α,α-difluoro-α-iodoacetate (16-6) in the presence of copper metal to provide 16-2. Treatment of ester 16-2 with sodium borohydride at low temperature then provides key intermediate 16-7. Preparation of intermediate 16-9 is carried out by first protecting commercially available 4-(hydroxymethyl) piperidine as the N-Boc derivative, then forming the methanesulfonyl ester under standard conditions, displacing the mesylate group with an iodide, and finally treating the iodide with triphenylphosphine. Coupling of 16-7 with phosphonium salt 16-9 in the presence of a strong base, such as potassium hexamethyldisilazide, sodium hydride, lithium diisopropylamide, or similar reagents, affords olefin 17-10. Reduction of the double bond of 16-10 is effected by treatment with iridium metal in t-butanol or hexane under an

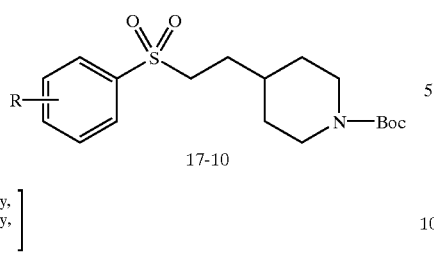

17-10

[R = H, alkyl, halo, alkoxy, haloalkyl, haloalkoxy, and the like]

Procedures for synthesizing the present compounds containing 4-(2-(arylthio)ethyl)piperidine functionality are shown in Scheme 17. Treatment of phosphonoacetate 17-1 with KHMDS followed by addition of commercially available N-Boc-4-piperidone 17-2 provides unsaturated ester 17-3. Hydrogenation of 17-3 followed by hydrolysis to the acid and then reduction with borane-methyl sulfide then affords primary alcohol 17-4. Treatment with iodine and triphenylphosphine under standard conditions yields iodide 17-5. Reaction of the anion of a suitable aryl sulfide 17-6 with iodide 17-5 affords 4-(2-(arylthio)ethyl)-piperidine derivative 17-7. Sulfide can be deprotected directly under acidic conditions to give piperidine 17-8. Alternatively, the sulfur may be oxidized with one or two equivalents of a mild oxidizing agent such as Oxone® or mCPBA (m-chloroperoxybenzoic acid) to provide the corresponding sulfoxide or sulfone, respectively. In each case, the Boc group can be removed to provide sulfoxide 17-9 and sulfone 17-10. Each of these N-unsubstituted piperidines are then utilized as the cyclic secondary amine component as shown above in Schemes 1 and 2.

One synthesis of a secondary amine intermediate is given in Scheme 18. Bromination of 2-butanone, followed by condensation with 2-aminopyridine, affords imazopyridine 18-3. Bromination and then palladium-catalysed coupling with the pyridyl stannane 18-5 provides pyridine derivative 18-6, which upon hydrogenation under acidic conditions yield intermediate 18-7.

SCHEME 18

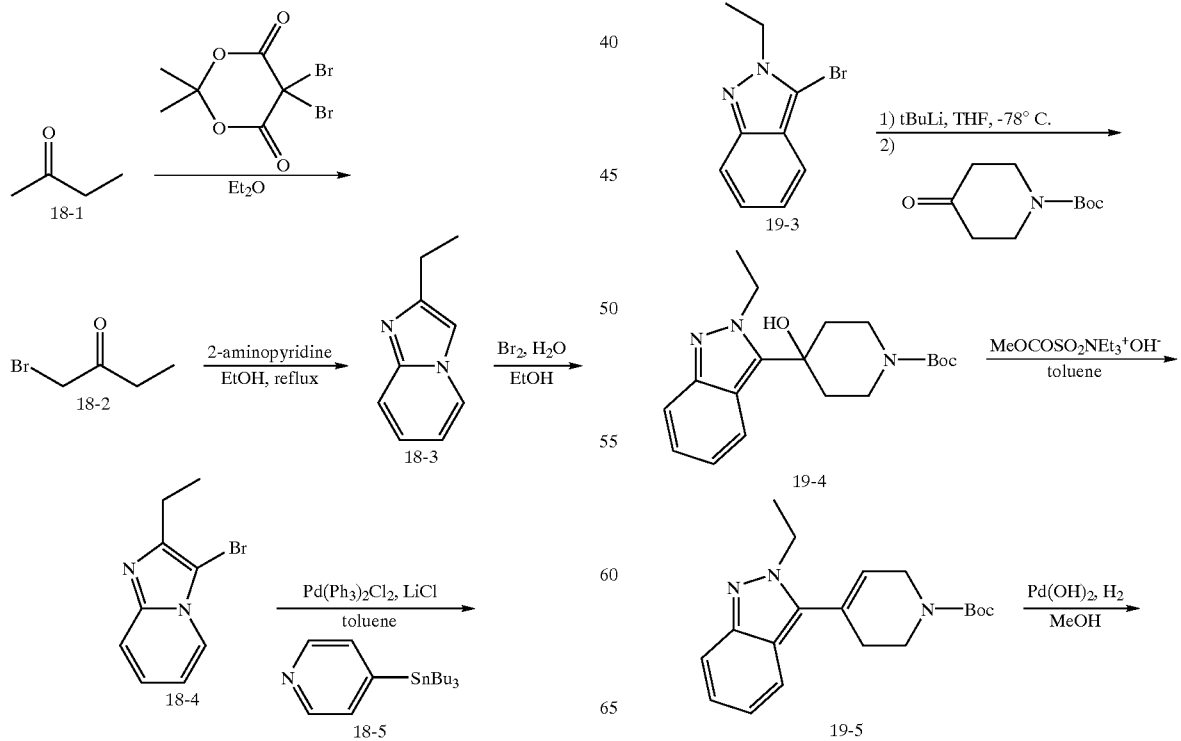

SCHEME 19

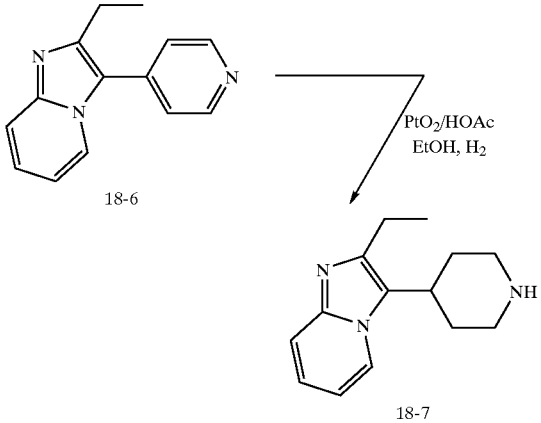

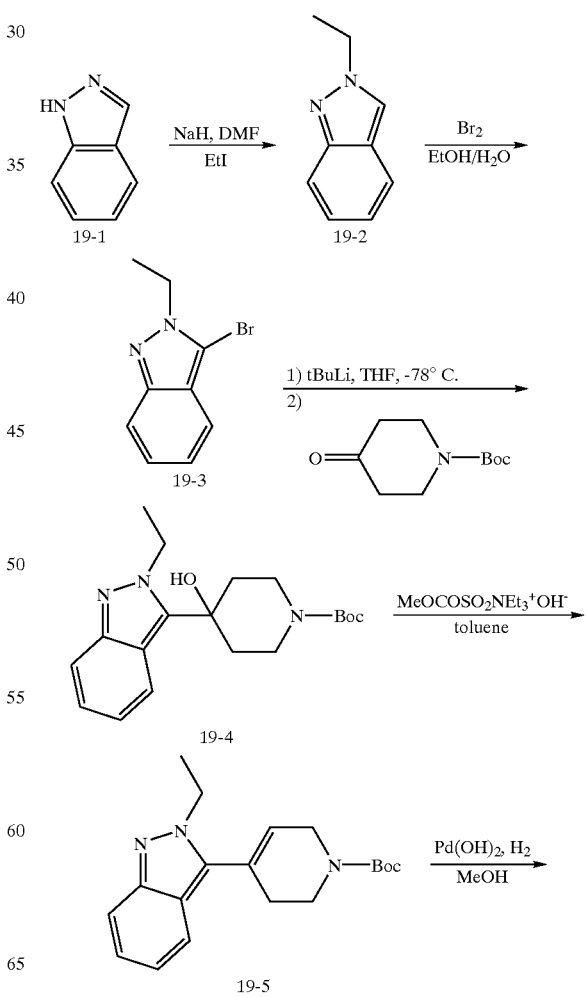

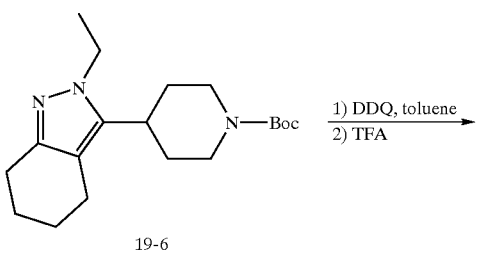

19-6

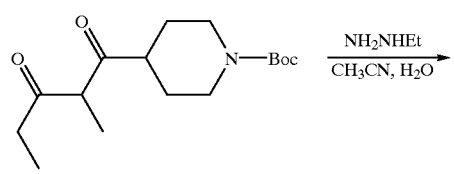

20-6

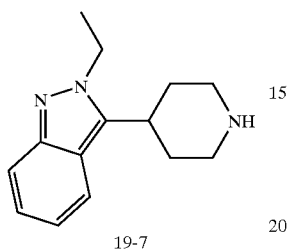

19-7

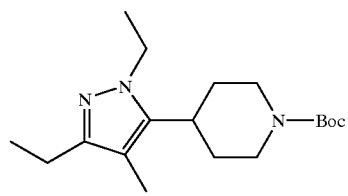

20-7

HCl/MeOH

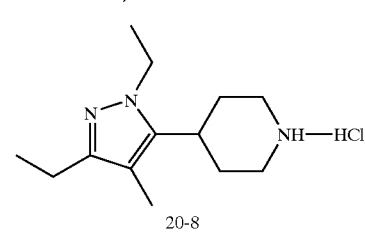

20-8

A synthesis of a secondary amine intermediate bearing an indazole substituent is given is Scheme 19. Alkylation of indazole with sodium hydride and then ethyl iodide affords the 2 alkylindazole derivative 19-2. Bromination under standard conditions provides bromide 19-3. Halogen-metal exchange, followed by trapping with the indicated pyridone derivative affords adduct 19-4, which can be dehydrated to yield 19-5. Hydrogenation produces 19-6, which can itself be employed as a secondary amine intermediate. Alternatively, it can be oxidized with DDQ and then treated with TFA to provide intermediate 19-7 as its TFA salt.

One synthesis of a secondary amine bearing a monocyclic pyrazole substituent is given in Scheme 20. Conversion of the Weinreb amide of Boc-protected isonipecotic acid to the aldehyde can be accomplished by treatment with DIBAL at low temperature in methylene chloride, to give aldehyde 20-3. Separately, formation of the lithium enolate of 2-butanone, followed by addition of 20-3, affords aldol 20-5. Oxidation to the diketone followed by treatment with ethylhydrazine in acetonitrile/water affords the pyrazole 20-7. Deprotection under acidic conditions then provides intermediate 20-8. Other substituents on the pyrazole nitrogen can be synthesized by utilizing other mono-substituted hydrazines in the condensation step with 20-6.

SCHEME 20

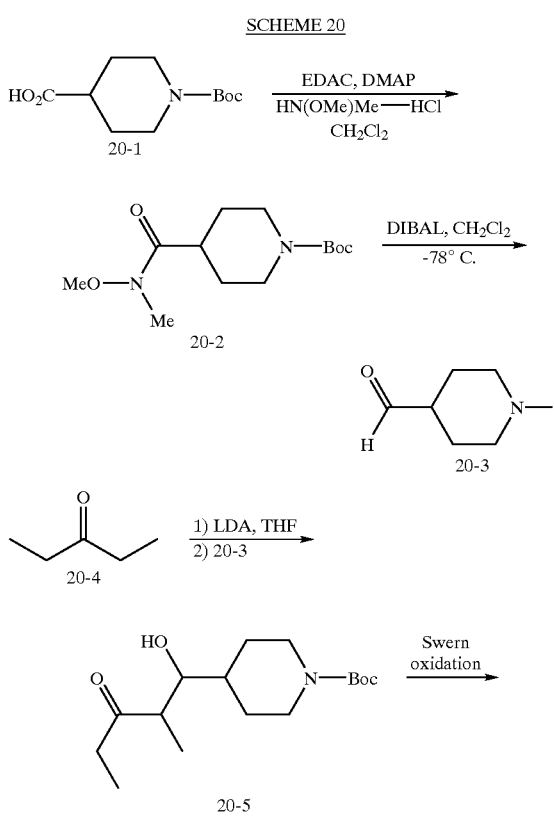

SCHEME 21

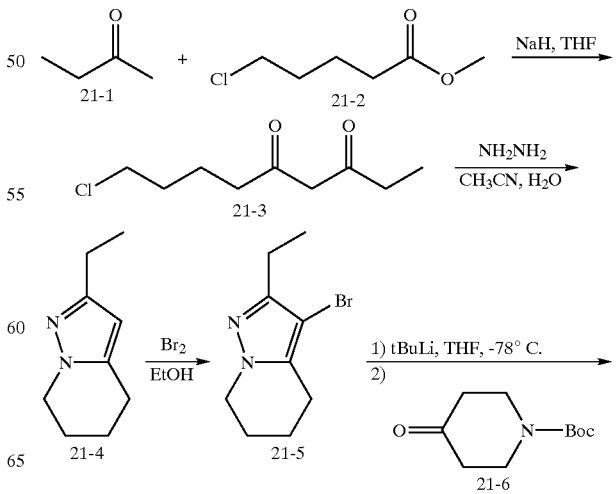

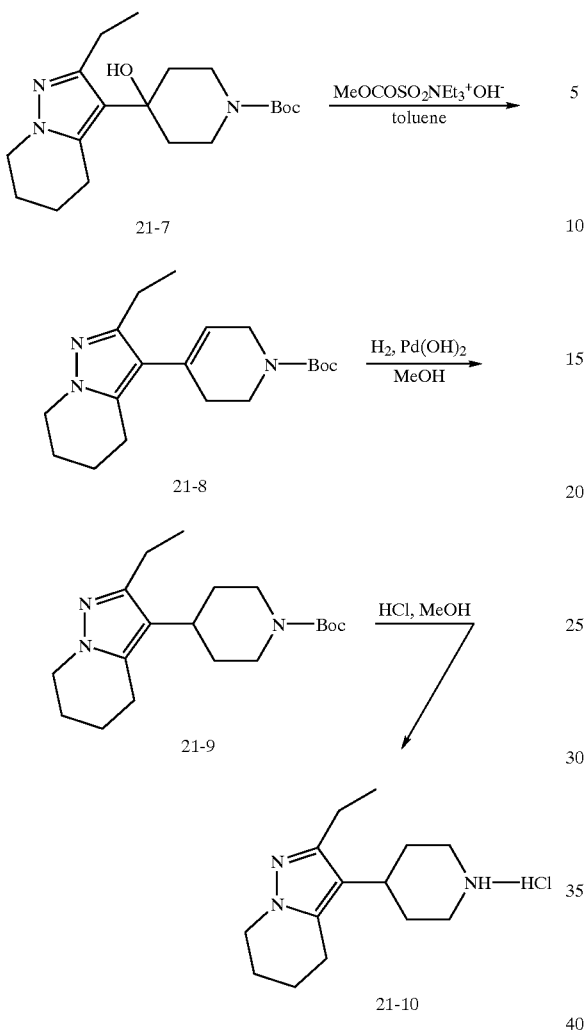

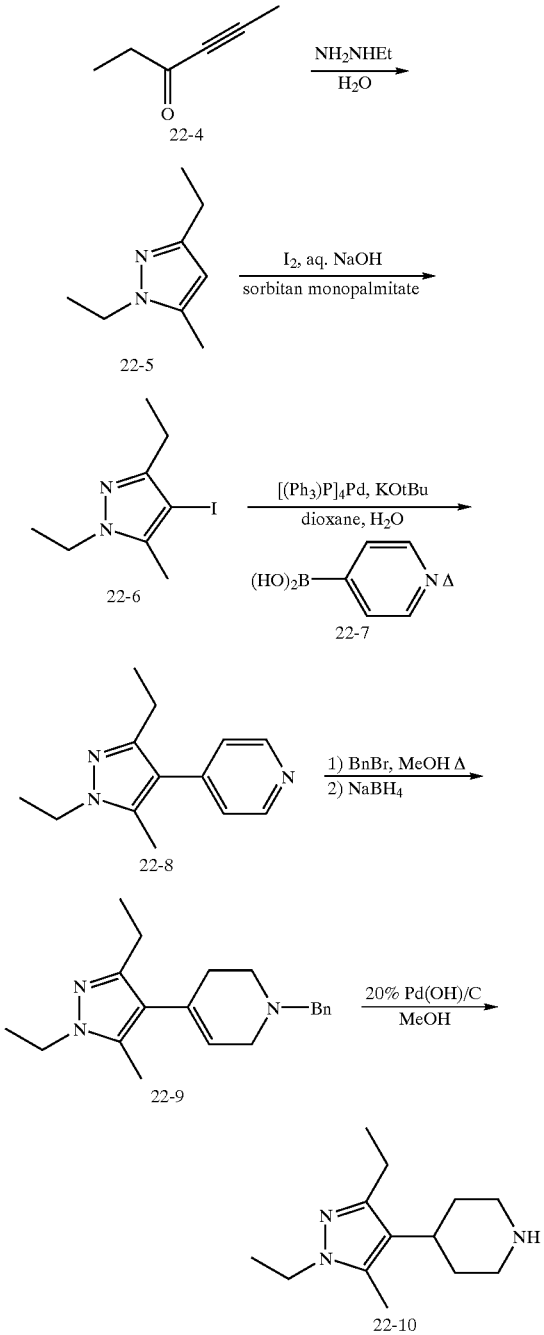

One synthesis of a secondary amine bearing a bicyclic pyrazole-based substituent is given in Scheme 21. Condensation of 2-butanone and methyl 5-chlorovalerate in the presence of sodium hydride in THF affords diketone 21-3. Treatment of this compound with hydrazine in acetonitrile/water provides pyrazolopiperidine 21-4, which upon exposure to bromine in ethanol yields bromide 21-5. Halogen-metal exchange of 21-5, followed by addition of ketone 21-6, affords 21-7. Dehydration in toluene and then hydrogenation under standard conditions provides piperidine 21-9, which can then be deprotected under acidic conditions, for example HCl in methanol, to afford desired secondary amine 21-10.

SCHEME 22

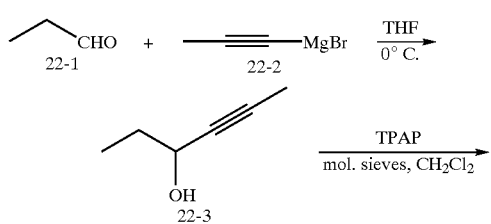

Another synthesis of a secondary amine bearing a monocyclic pyrazole substituent is given in Scheme 22. Addition of anion 22-2 to propionaldehyde affords alcohol 22-3, which can be oxidized to ketone 22-4. Treatment with ethylhydrazine yields pyrazole 22-5, which can be iodinated under phase-transfer conditions to provide iodide 22-6. Coupling of this aldehyde with 4-pyridineboronic acid in the presence of a suitable palladium catalyst affords 22-8. Alkylation of 22-8 with benzyl bromide, followed by reduction with sodium borohydride, yields tetrahydropyridine 22-9. Catalytic hydrogenation then provides secondary intermediate 22-10. The pyrazole nitrogen substituent can be varied by utilizing alternative mono-substituted hydrazine derivatives in the condensation with 22-4.

SCHEME 23

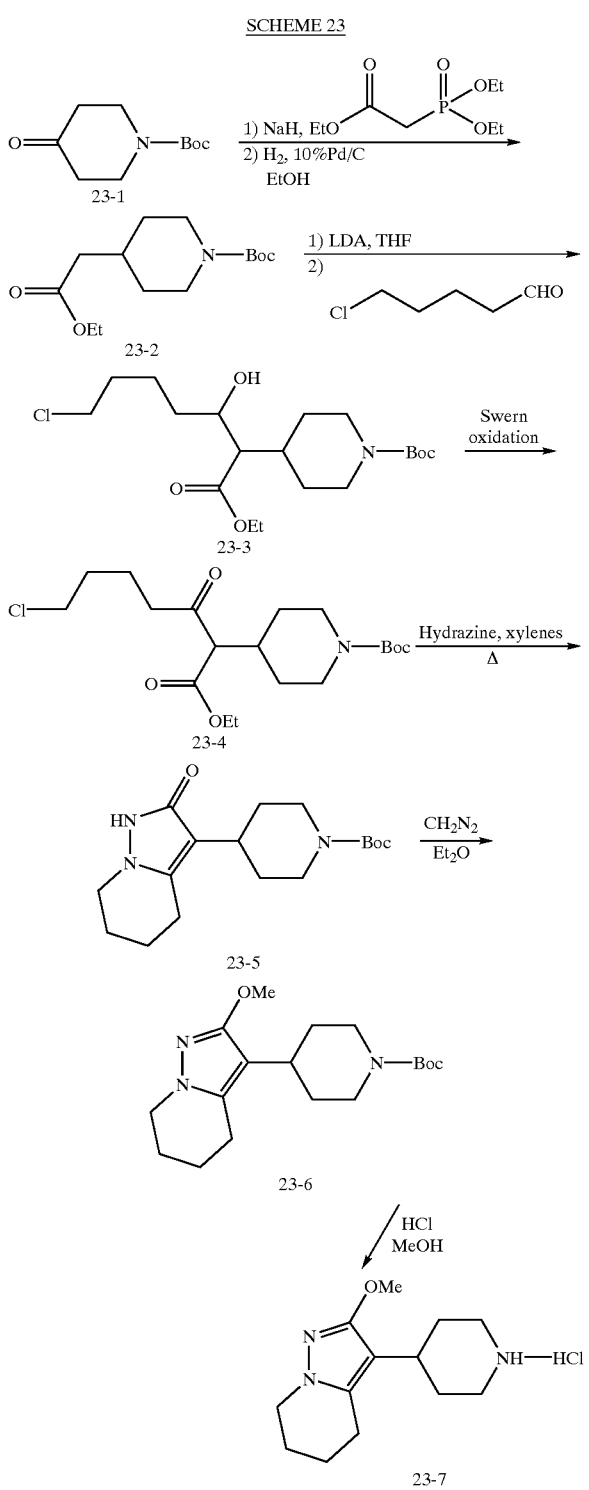

SCHEME 24

23-5 to diazomethane in ether provides methoxy derivative 23-6, which upon deprotection under acidic conditions then affords the desired secondary amine 23-7.

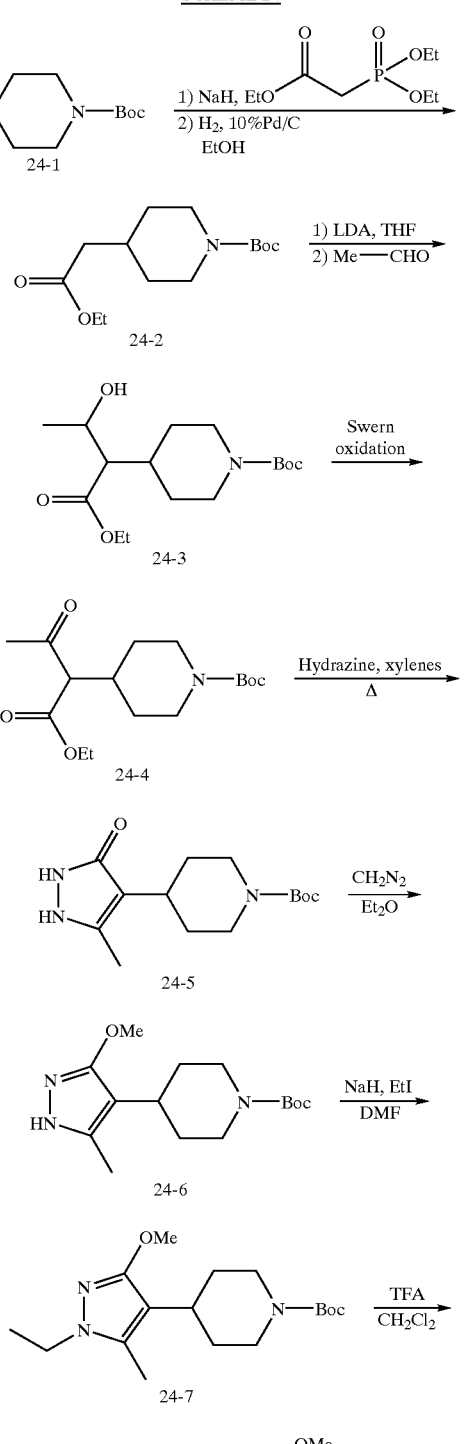

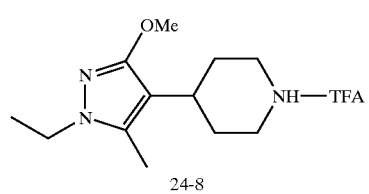

Another synthesis of a secondary amine bearing a bicyclic pyrazole-based substituent is given in Scheme 23. Condensation of N-Boc piperidone (23-1) with the anion of triethyl phosphonoacetate, followed by catalytic hydrogenation, provides piperidine 23-2. Formation of the enolate of 23-2 with a strong, non-nucleophilic base, such as ILDA, followed by addition of 5-chlorovaleraldehyde, yields alcohol 23-3. Following Swern oxidation to diketone 23-4, refluxing with hydrazine in xylenes affords bicycle 23-5. Exposure of Another synthesis of a secondary amine bearing a monocyclic pyrazole substituent is given in Scheme 24. Condensation of N-Boc piperidone (24-1) with the anion of triethyl phosphonoacetate, followed by catalytic hydrogenation, provides piperidine 24-2. Formation of the enolate of 24-2 with a strong, non-nucleophilic base, such as LDA, followed by addition of acetaldehyde, yields alcohol 24-3. Following Swern oxidation to diketone 24-4, refluxing with hydrazine in xylenes affords pyrazolone 24-5. Exposure of 24-5 to diazomethane in ether provides methoxy derivative 24-6. Alkylation of pyrazole 24-6 by treating with sodium hydride and then ethyl iodide affords fully-substituted pyrazole 24-7. Alternatively, other alkylating agents can be employed in place of ethyl iodide to provide differently substituted pyrazoles. Deprotection with trifluoroacetic acid in methylene chloride then provides secondary amine 24-8.

SCHEME 25

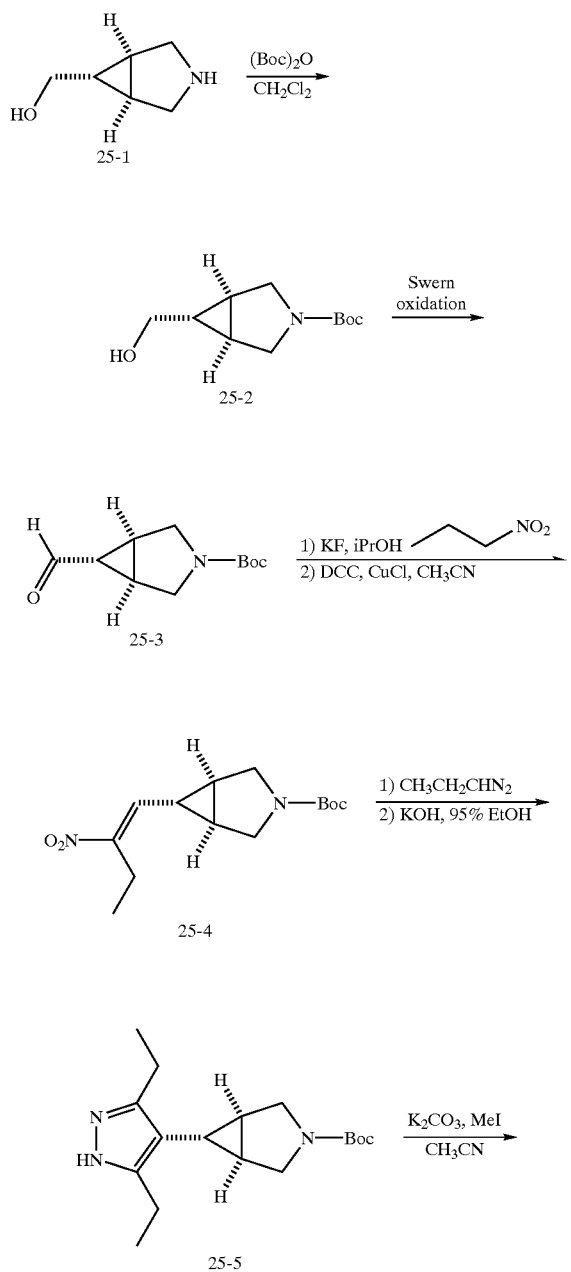

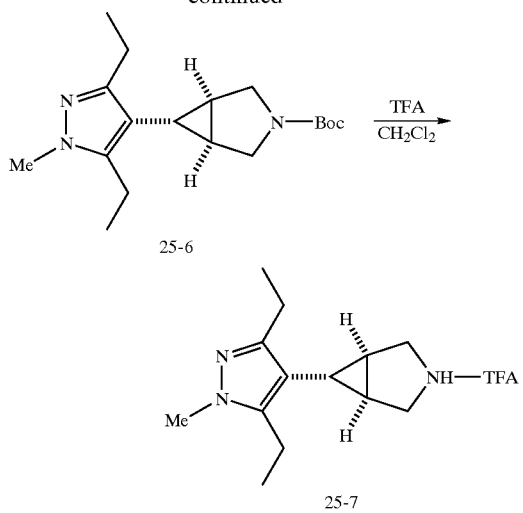

Synthesis of secondary amines with an azabicyclo[3.1.0] hexane ring system is shown in Scheme 25. Treatment of bicycle 25-1 (prepared as described in Brighty, K. E.; Castaldi, M. J. *Synlett* 1996, 1097) with Boc anhydride in methylene chloride affords protected derivative 25-2. Swern oxidation provides aldehyde 25-3, which upon treatment with 1-nitropropane and potassium fluoride in isopropanol, followed by elimination by addition of dicyclohexylcarbodiimide and copper (I) chloride, yields olefin 25-4 as a mixture of geometric isomers. Treatment of this nitro-olefin with diazopropane, followed by treatment with potassium hydroxide in aqueous ethanol, affords the pyrazole 25-5. Alkylation of 25-5 with methyl iodide in the presence of potassium carbonate yields the N-methyl derivative 25-6, which can be deprotected to the desired secondary amine intermediate 25-7 with trifluoroacetic acid in methylene chloride. Other alkylating agents can be used in place of methyl iodide to afford the corresponding N-substituted derivatives. Likewise, other nitromethylalkanes can be employed in place of 1-nitropropane, and alternative diazoalkanes in place of diazopropane can be utilized, to afford the corresponding final products analogous to 25-7.

The following examples serve only to illustrate the invention and its practice. The examples are not to be construed as limitations on the scope or spirit of the invention.

EXAMPLE 1

N-[1(S)-1-phenyl-3-(4-[3-benzyl-1-ethyl(1H-pyrazol-5-yl)]piperidin-1-yl)propyl]cyclobutanecarboxamide, bis-TFA salt

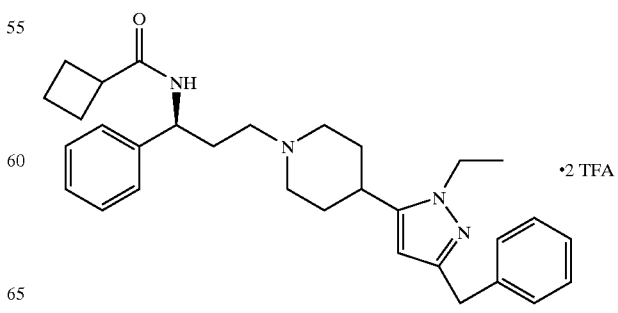

Step A: Methyl (3S)-3-[(tert-butoxycarbonyl)amino]-3-phenylpropionate

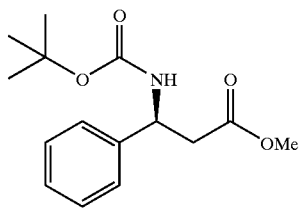

A solution of 15 mL of DMF charged with (3S)-3-[(tert-butoxycarbonyl)amino]-3-phenylpropionic acid (8 mmol, 2.0 g), methyl iodide (15 mmol, 1.9 mL) and $K_2CO_3$ (15 mmol, 2.1 g), was stirred at ambient temperature for 16 h. The reaction mixture was poured into 50 mL of saturated $NaHCO_3$, and the resulting solution was extracted with ether (3×50 mL). The combined organic phase was washed with 50 mL of $H_2O$, dried with $MgSO_4$, and the solvent removed under reduced pressure to yield the title compound as a slightly yellow solid. $^1$H NMR (500 MHz, $CDCl_3$): δ 7.26–7.38 (m, 5 H), 5.49 (br s, 1H), 5.13 (br s, 1H), 3.65 (s, 3H), 2.80–2.96 (m, 2H), 1.45 (s, 9H). MS (ESI): m/z 302 (M+Na).

Step B: tert-Butyl (1S)-3-oxo-1-phenylpropylcarbamate

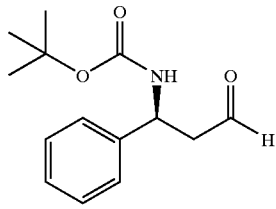

The compound was prepared from the title compound in Example 1, Step A (4 mmol, 1.1 g) as described in WO 00/39125, pp. 57–58. The aldehyde was further purified by flash chromatography on silica gel using a step gradient of hexanes, 4% EtOAc/hexanes, 8% EtOAc/hexanes, 12% EtOAc/hexanes and 16% EtOAc/hexanes. The aldehyde eluted in 16% EtOAc/hexanes. Removal of solvent under reduced pressure afforded the title compound as a white solid. $^1$H NMR (500 MHz, $CDCl_3$): δ 9.78 (s, 1H), 7.36–7.41 (m, 2H), 7.28–7.35 (m, 3 H), 5.23 (br s, 1H), 5.12 (br s, 1H), 2.84–3.04 (m, 2H), 1.45 (s, 9H). MS (ESI): m/z 290 (dihydrate+Na).

Step C: 1-(1-[tert-Butoxycarbonyl]piperidin-4-yl)-4-phenyl-butane-1,3-dione

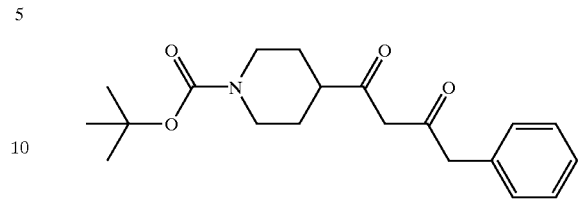

Method A n-Butyllithium (100 mL, 0.16 mole) was added to a stirred solution of diisopropylamine (16.16 g, 22.4 mL, 0.16 mole, distilled) in THF (450 mL) at 0° C. over 45 min under nitrogen. Stirring was continued for 10 min at 0° C. after the addition was complete. After cooling to –78° C., phenylacetone (21.45 g, 21.13 mL, 0.16 mole) in THF (100 mL) was added dropwise over 15 min with stirring. This solution was stirred at –78° C. for 1 h. Meanwhile, a solution of N-Boc isonipecotic acid (18.32 g, 0.080 mole) and carbonyl diimidazole (12.98 g, 0.080 mole) in THF (150 mL) was prepared. After stirring for 15 min, this solution was cannulated into the enolate solution dropwise over 15 min. The reaction was stirred at <–70° C. for 1 h and then allowed to warm to rt over 3 h. The reaction was quenched with 1M citric acid (250 mL) and stirred for 16 h. The organic layer was separated and washed with 250 mL each of saturated sodium bicarbonate solution, water and brine. After drying over sodium sulfate, the organic layer was concentrated to give an oil. The residue was purified by FC on silica gel (10% ethyl acetate in 60–80° C. petroleum ether) to give separation of the two isomers. The first higher $R_f$ fractions afforded pure title compound as the minor product as an oil.

$^1$H NMR (500 MHz, $CDCl_3$): δ 7.34–7.37 (m, 2 H), 7.25–7.31 (m, 3 H), 5.46 (s, 1 H), 4.11–4.17 (m, 2 H), 3.63 (s, 2H), 2.70–2.76 (m, 2 H), 2.29 (tt, J=11.7 and 3.7 Hz, 1 H), 1.75–1.80 (m, 2 H), 1.47–1.61 (m, 2 H), 1.47 (s, 9 H). MS (ESI): m/z 346 (M+1).

The lower $R_f$ fractions contained phenylacetone and major product 1-(1-(t-butoxycarbonyl)piperidin-4-yl)-2-phenylbutane-1,3-dione from which the latter crystallized on standing to give 7 g white solid (m.p. 105–106° C.).

$^1$H NMR (360 MHz, $CDCl_3$): δ 15.23 (s, 1 H), 7.3–7.45 (m, 3 H), 7.15–7.2 (m, 2 H), 4–4.1 (m, 2 H), 2.35–2.50 (m, 2 H), 2.2–2.3 (m, 1 H), 1.87 (s, 3 H), 1.5–1.75 (m, 4 H), 1.43 (s, 9 H).

MS (ESI): m/z 346 (M+1).

Method B

Step 1: 1-(t-Butoxycarbonyl)piperidine-4-N-methyl-N-methoxycarboxamide

N-Boc isonipecotic acid (13.566 g, 59.2 mmol), N,O-dimethyl hydroxylamine hydrochloride (8.657 g, 88.7 mmol), and 1-hydroxybenzotriazole hydrate (15.99 g, 118.3 mmol) were dissolved in DMF (225 mL) in a 500 mL round-bottom flask and diisopropylethylamine (15.29 g, 20.6 mL, 118.3 mmol) was then added with stirring at rt. 1-Ethyl-3-(3-dimethylamino-propyl)carbodiimide (17.01 g, 88.74 mmol) was added in several portions over 10 min with stirring. After 22 h, the reaction mixture was poured into a water and ice mixture (600 mL) and was extracted with ethyl acetate (5×125 mL). The combined organic layers were washed with 1N HCl (2×200 mL), 5% sodium bicarbonate (2×200 mL), water and brine, dried over sodium sulfate and concentrated to give the title compound as a yellowish oil.

$^1$H NMR (500 MHz, CDCl$_3$): δ 4.11–4.20 (m, 2 H), 3.72 (br s, 3 H), 3.20 (br s, 3 H), 2.75–2.86 (m, 3 H), 1.63–1.76 (m, 4 H), 1.47 (s, 9 H).

Step 2: 4-Acetyl-1-(t-butoxycarbonyl)piperidine

After dissolving the above Weinreb amide in anhydrous ether (400 mL) under nitrogen and cooling the solution in an ice bath, 1.4M methyl magnesium bromide (55 mL) in 3:1 toluene and THF was added with stirring and cooling over 30 min. After stirring at 0° C. for 1 h, the reaction was poured into a mixture of ice water (400 mL) and acetic acid (0.8 mL, 150 mmol). The layers were separated and the aqueous layer was extracted twice with ether. The combined organic layers were washed with 0.1N HCl (200 mL), 3% sodium bicarbonate (200 mL), water (200 mL) and brine (200 mL), dried over sodium sulfate, and concentrated to give the crude product. FC (20–80% ethyl acetate in hexanes) gave the title compound as a yellowish oil. R$_f$: 0.27 (25% ethyl acetate in hexanes). Some starting Weinreb amide was also recovered. R$_f$: 0.10 (25% ethyl acetate in hexanes).

$^1$H NMR (500 MHz, CDCl$_3$): δ 4.07–4.14 (m, 2 H), 2.75–2.83 (m, 2 H), 2.46 (tt, J=11.3 and 3.8 Hz, 1 H), 2.17 (s, 3 H), 1.82–1.87 (m, 2 H), 1.48–1.57 (m, 2 H), 1.46 (s, 9 H).

Step 3: 1-(1-(t-Butoxycarbonyl)piperidin-4-yl)-4-phenyl-butane-1,3-dione

To a suspension of 60% sodium hydride (1.07 g) in THF (15 mL) at 0° C. was added a solution of 4-acetyl-1-(t-butoxycarbonyl)-piperidine from Step B2 (3.03 g, 13.3 mmol) and methyl phenylacetate (6.01 g, 39.9 mmol) in THF (6 mL) over 20 min. The reaction was stirred for another 4 h as it was allowed to warm to rt. The mixture was diluted with ether (30 mL) and poured into 1N HCl. The layers were separated and the aqueous layer was extracted three times with ether. The combined organic layers were washed with brine (150 mL), dried over sodium sulfate and concentrated. The crude product was purified by FC (20% ethyl acetate in hexanes) to give the title compound. R$_f$: 0.30 (20% ethyl acetate in hexane). Its NMR was the same as that obtained from the product of Method A above.

Step D: 4-(3-Benzyl-1-ethyl-(1H-pyrazol-5-yl))-1-(tert-butoxycarbonyl)piperidine

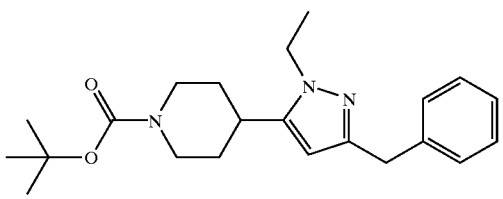

Method A 1-(1-(t-Butoxycarbonyl)piperidin-4-yl)-4-phenyl-butane-1,3-dione (from Step A, either Method A or Method B), (0.851 g, 2.46 mmol) in methanol (25 mL) was added over 10 min to a suspension of ethylhydrazine oxalate (0.444 g, 2.96 mmol) in methanol (5 mL) in a 60° C. oil bath. After 15 h, the reaction was concentrated in vacuo and the residue was purified by repeated FC using a gradient of 50–100% ethyl acetate in hexanes to give first 4-(5-benzyl-1-ethyl-(1H-pyrazol-3-yl))-1-(t-butoxycarbonyl)piperidine as the higher R$_f$ product isomer and then the title compound as the lower R$_f$. $^1$H NMR (500 MHz): δ 7.26~7.31 (m, 4H), 7.19~7.23 (m, 1H), 5.72 (s, 1H), 4.16~4.24 (m, 2H), 4.08 (q, J=7.3 Hz, 2H), 3.94 (s, 2H), 2.76~2.82 (m, 2H), 2.66 (tt, J=3.6 & 11.9 Hz, 1H), 1.80~1.85 (m, 2H), 1.49~1.58 (m, 2H), 1.48 (s, 9H), 1.45 (t, J=7.3 Hz, 3H); ESI-MS 370.2 (M+H), HPLC A: 3.70 min. The other isomer's ESI-MS 370.2 (M+H), HPLC A: 3.77 min.

Method B

Step 1: 1-(t-Butoxycarbonyl)-4-hydroxymethyl-piperidine

A solution of 25.03 g (109.2 mmole) N-Boc isonipecotic acid was dissolved in 200 mL TBF and treated with 200 mL 1 M borane-tetrahydrofuran complex in THF, and the mixture was stirred overnight. The mixture was concentrated under vacuum, diluted with 750 mL ethyl acetate, and washed with 150 mL 1 N HCl (6×) and then saturated brine. The organic layer was dried over sodium sulfate and concentrated to give crude product as a white solid. $^1$H NMR (500 MHz) δ4.15 (br d, J=13.7 Hz, 2H), 3.52 (d, J=6.2 Hz, 2H), 2.69~2.75 (m, 2H), 1.71~1.75 (m, 2H), 1.62~1.70 (m, 1H), 1.47 (s, 9H), 1.12~1.21 (m, 2H). This was used as is in the next step.

Step 2: 1-(t-Butoxycarbonyl)-4-formyl-piperidine

A mixture of 17.62 g (135.6 mmole) oxalyl chloride and 250 mL DCM in a dry ice acetone bath was treated with a solution of 21.19 g (271.2 mmole) DMSO in 150 mL DCM over 20 minutes. After stirring for 20 minutes, a solution of 24.327 g 1-(t-butoxycarbonyl)-4-hydroxymethyl-piperidine (from Step 1 above) in 150 mL DCM was added over one hour. After an additional 15 minutes, 57.17 g (565 mmole) triethylamine in 150 mL DCM was added over half an hour. The reaction mixture was allowed to warm up over night in the cooling bath. The reaction mixture was concentrated under vacuum to remove about 400 mL DCM, and the residue was partitioned between 1 L ether and 300 mL water. To this was added 200 mL 1 N NaOH, the layers were separated, and the organic layer was washed with 150 mL 1 N NaOH (2×), water (3×), and saturated brine, dried over sodium sulfate, and concentrated to give crude product. FC (10~60% ethyl acetate in hexanes) gave the title compound as slightly yellowish oil. R$_F$: 0.29 (3:1 v/v hexanes/EtOAc); $^1$H NMR (500 MHz) δ 9.68 (d, J=0.7 Hz, 1H), 3.96~4.02 (m, 2H), 2.92~2.97 (m, 2H), 2.40~2.45 (m, 1H), 1.88~1.94 (m, 2H), 1.53~1.64 (m, 2H), 1.47 (s, 9H).

Step 3: 1-(t-Butoxycarbonyl)-4-(2,2-dibromoethen-1-yl)-piperidine

A solution of 48.615 g (146.6 mmole) carbon tetrabromide in 150 mL DCM was added dropwise with stirring to a solution of 76.895 g (293.2 mmole) triphenylphosphine in 150 mL DCM in a 1-L rb flask with ice bath cooling over 1.75 hours. After 40 minutes, a solution of 15.631 g (73.29 mmole) 1-(t-butoxycarbonyl)-4-formyl-piperidine (from Step 2 above) in 100 mL DCM was added to the resulting brown suspension with stirring and cooling over 40 minutes. After one hour, 200 mL ether and 400 mL hexanes was added. The top suspension was filtered through Celite, and the residue was resuspended in 150 mL DCM and treated with 300 mL ether. The mixture was filtered, and the solid was washed with hexanes till total filtrate was 2 L. The filtrate was filtered again through Celite and washed with hexanes. The filtrate was washed with 100 mL 5 % NaHCO₃, 300 mL water (2×), and 150 mL brine. The organic layer was dried over Na₂SO₄ and concentrated under vacuum to give crude product as a yellowish solid. Flash chromatography (FC) on 250 g silica gel (0~15% EtOAc in hexanes) gave title compound as a white solid. R$_F$: 0.57 (15% EtOAc in hexanes); ¹H NMR (500 MHz) δ 6.25 (d, J=8.9 Hz, 1H), 4.04~4.12 (m, 2H), 2.75~2.83 (m, 2H), 2.42~2.50 (m, 1H), 1.69~1.75 (m, 2H), 1.47 (s, 9H), 1.29~1.37 (m, 2H).

Step 4: 1-(t-Butoxycarbonyl)-4-(2-tributylstannylethyn-1-yl)-piperidine

A mixture of 23.199 g (62.85 mmole) 1-(t-butoxycarbonyl)-4-(2,2-dibromoethen-1-yl)-piperidine (prepared as in Step 3 above) and 600 mL anhydrous THF was cooled with dry ice acetone bath under nitrogen. To this mixture was added 88 mL of a 1.6 M BuLi solution in hexanes dropwise with stirring and cooling over 50 minutes. After one hour, the flask was transferred into an ice bath. After another hour, a solution of 28.64 g (87.99 mmole) tributyltin chloride in 100 mL TBF was added with stirring and cooling over 35 minutes. After three hours, the mixture was concentrated under vacuum to remove some THF, and the residue was partitioned between 600 mL ice water and 800 mL ether. The organic layer was washed with 200 mL of water (1×), 2% NaHCO₃ (1×), water (2×), and saturated brine (1×), dried over Na₂SO₄ and concentrated under vacuum to give crude product as a green-yellowish liquid. FC on 275 g silica gel using cold 2.5~15% EtOAc in hexanes as quickly as possible to give the title compound as a colorless liquid. R$_F$: 0.45 (10% EtOAc in hexanes); ¹H NMR (500 MHz) δ 3.63~3.67 (m, 2H), 3.25~3.30 (m, 2H), 2.64~2.69 (m, 1H), 1.74~1.79 (m, 2H), 1.54~1.64 (m, 8H), 1.47 (s, 9H), 1.32~1.39 (m, 6H), 0.96~0.99 (m, 6H), 0.92 (t, J=7.3 Hz, 9H).

Step 5: 4-(1-(t-Butoxycarbonyl)piperidin-4-yl)-1-phenyl-2-butanon-3-yne

To a mixture of 1.727 g (3.466 mmole) 1-(t-butoxycarbonyl)-4-(2-tributyl-stannylethyn-1-yl)-piperidine (prepared in Step 4 above) in 18 mL 1,2-dichloroethane was added 0.536 g (3.466 mmole) phenylacetyl chloride and 50 mg dichlorobis-(triphenylphosphine)palladium (II). The mixture was refluxed under nitrogen for 2 hours, then concentrated under vacuum. Purifying the residue on silica gel (5~35% ethyl acetate in hexanes) gave the title compound as a yellow oil. R$_F$: 0.27 (20% EtOAc in hexanes); ¹H NMR (500 MHz) δ 7.34~7.38 (m, 2H), 7.28~7.32 (m, 1H), 7.24~7.27 (m, 2H), 3.82 (s, 2H), 3.49~3.54 (m, 2H), 3.17~3.23 (m, 2H), 2.68~2.73 (m, 1H), 1.72~1.77 (m, 2H), 1.51~1.57 (m, 2H), 1.47 (s, 9H). Tetrakis (triphenylphosphine)palladium gave a similar result.

Step 6: 4-(3-Benzyl-1-ethyl-(1H-pyrazol-5-yl))-1-(tert-butoxycarbonyl)piperidine Heating 1.204 g (3.677 mmole) 4-(1-(t-butoxycarbonyl)piperidin-4-yl)-1-phenyl-2-butanon-3-yne (prepared in Step 5 above) with 0.662 g (4.413 mmole) ethylhydrazine oxalate and 1.252 g (9.687 mmole) DIEA in 20 mL ethanol overnight gave 8:1 ratio of the title compound and its isomer 4-(5-benzyl-1-ethyl-(1H-pyrazol-3-yl))-1-(tert-butoxycarbonyl)piperidine. Use of ethylhydrazine free base gave even more favorable ratios of the desired title compound. The desired isomer can be isolated by recrystallization using hexanes or by silica gel chromatography using 5~10% MeCN in DCM in addition to the procedure described in Method A above.

Step E: 4-(3-Benzyl-1-ethyl-(1H-pyrazol-5-yl)) piperidine, HCl salt

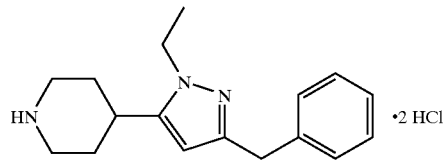

•2 HCl

Into a stirring solution of the title compound in Example 1, Step D (29 mmol, 10.0 g) in 200 mL of methanol was slowly bubbled HCl (g) for 1.5 h at 0° C., after which time HPLC analysis indicated the deprotection was complete. The solvent was removed under reduced pressure affording the title compound as a white solid. MS (ESI): m/z 270 (M+H). HPLC B: 0.89 min.

Step F: tert-Butyl-(1S)-1-phenyl-3-(4-[3-benzyl-1-ethyl(1H-pyrazol-5-yl)]piperidin-1-yl) propylcarbamate

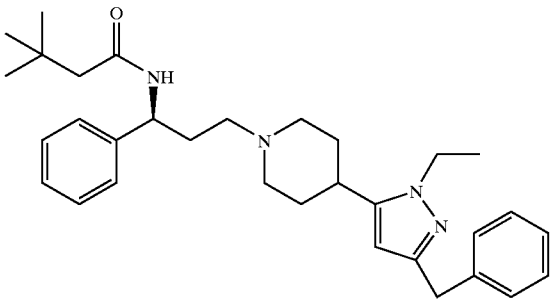

To a solution of the title compound from preparation Example 1, Step B (10 mmol, 2.5 g), 4-[3-benzyl-1-ethyl-pyrazol-5-yl]piperidine, bis HCl salt (Example 1, Step E, 11 mmol, 4.5 g) and N,N-diisopropylethylamine (40 mmol, 7 mL) in 40 mL of DCM was added NaBH(OAc)₃ (30 mmol, 6.4 g). The slurry was sonicated briefly and the reaction mixture was allowed to stand at ambient temperature for 1 h. The reaction mixture was washed with 20 mL of H₂O. The organic phase was dried with MgSO₄ and the solvent was removed under reduced pressure. The residue was purified by silica gel chromatography eluting with 1:20:79 NH₄OH/ EtOAc/hexanes and 1:40:59 NH₄OH/EtOAc/hexanes, affording the title compound as a white foamy solid. MS (ESI): m/z 503 (M+H). EPLC B: 1.78 min.

Step G: (1S)-1-phenyl-3-(4-[3-benzyl-1-ethyl(1H-pyrazol-5-yl)]piperidin-1-yl)propylamine, tris-HCl salt

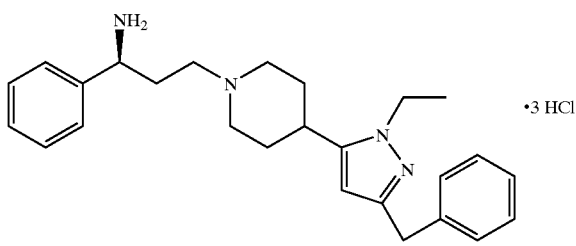

The title compound from Example 1, Step F (2.7 mmol, 2.0 g) was stirred in 50 mL of a premixed solution of 10:1 (v/v) of methanol/acetyl chloride. After 4 h the solvent was removed under reduced pressure, affording the title compound as a white solid. MS (ESI): m/z 403 (M+H). BPLC B: 1.00 min.

Step H: N-[1(S)-1-phenyl-3-(4-[3-benzyl-1-ethyl (1H-pyrazol-5-yl)]piperidin-1-yl)propyl] cyclobutanecarboxamide, bis-TFA salt

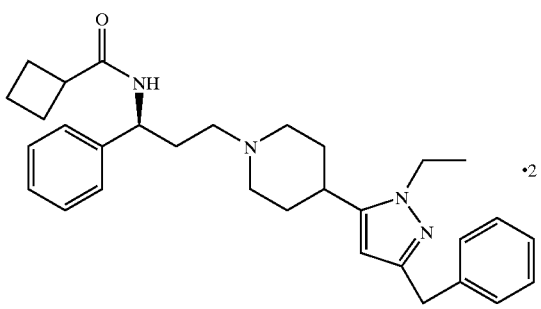

To a solution of the title compound from Example 1, Step G (0.12 mmol, 59 mg), cyclobutanecarboxylic acid (0.35 mmol, 33 μL) and triethylamine (0.58 mmol, 100 μL) in 2 mL of DCM was added 1-(3-dimethylamino)propyl-3-ethylcarbodiimide hydrochloride (0.35 mmol, 66 mg). The reaction mixture was allowed to stand at room temperature for 2 h, after which time the solvent was removed under a stream of nitrogen. The residue was taken up in 1:1 dioxane/H$_2$O and purified by reverse-phase chromatography, affording title product as a white solid. MS (ESI): m/z 485 (M+H). HPLC B: 1.55 min.

EXAMPLE 2

N-[1(S)-1-phenyl-3-(4-[3-benzyl-1-ethyl(1H-pyrazol-5-yl)]piperidin-1-yl)propyl]N-acetyl-3-azetidinecarboxamide, bis-TFA salt

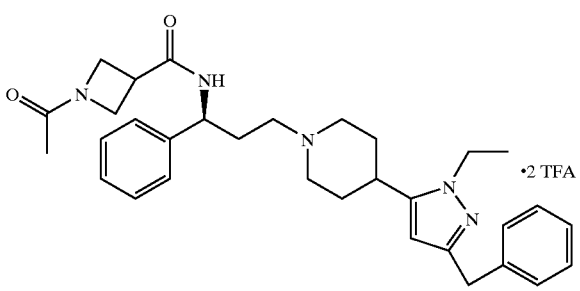

The compound was obtained from the title compound in Example 1, Step G by an analogous procedure as described in Example 1, Step H. MS ESI): m/z 528 (M+H). HPLC B: 1.25 min.

EXAMPLE 3

N-[1(S)-1-phenyl-3-(4-[3-benzyl-1-ethyl(1H-pyrazol-5-yl)]piperidin-1-yl)propyl]-3-carboxypropylcarboxamide, bis-TFA salt

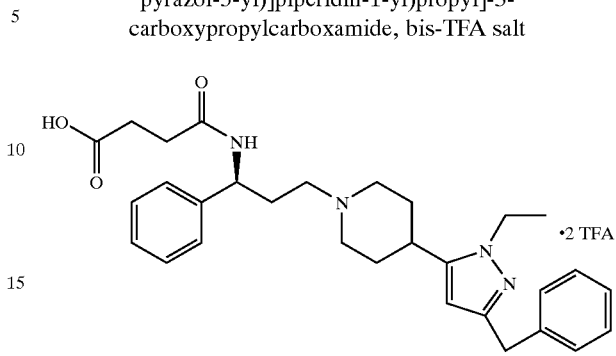

To a solution of the title compound in Example 1, Step G (0.06 mmol, 32 mg) and N,N-diisopropylethylamine (0.4 mmol, 70 μL) in 1 mL of DCM was added succinic anhydride (1 mmol, 100 mg). After 1 h methanol (0.15 mL) was added and the reaction was allowed to stand for 15 h. The solvent was removed under a stream of nitrogen. The residue was taken up in 1:1 dioxane/H$_2$O and purified by reverse-phase chromatography. The product was lyophilized affording the title compound as a white solid. MS ESI): m/z 503 (M+H). HPLC B: 1.32 min.

EXAMPLE 4A

N-[1(S)-1-phenyl-3-(4-[3-benzyl-1-ethyl(1H-pyrazol-5-yl)]piperidin-1-yl)propyl] methylsulfonamide, bis-TFA salt

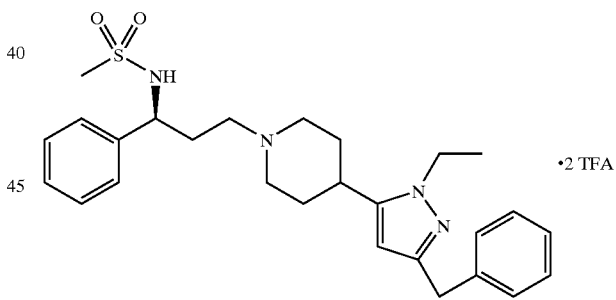

To a solution of the title compound from Example 1, Step G (0.06 mmol, 32 mg) and N,N-diisopropylethylamine (0.4 mmol, 70 μL) in DCM (1 mL) was added methanesulfonyl chloride (0.1 mmol, 8 μL). After 2 h the reaction was quenched by addition of 0.15 mL of methanol. The solvent was removed under a stream of nitrogen. The residue was taken up in 1:1 dioxane/H$_2$O and purified by reverse-phase HPLC. Lyophilization of the product afforded the title compound as a white solid. MS (ESI): m/z 481 (M+H). HPLC B: 1.37 min.

EXAMPLES 4B AND 4C

The following compounds were prepared by a procedure analogous to that set forth in Example 4A.

| Example No. | MS (ESI) | HPLC B |
|---|---|---|
| 4B: N-{(1S)-3-[4-(3-benzyl-1-ethyl-1H-pyrazol-5-yl)piperidin-1-yl]-1-phenylpropyl}ethanesulfonamide, bis trifluoroacetate salt | 495 (M + H) | 1.44 min |

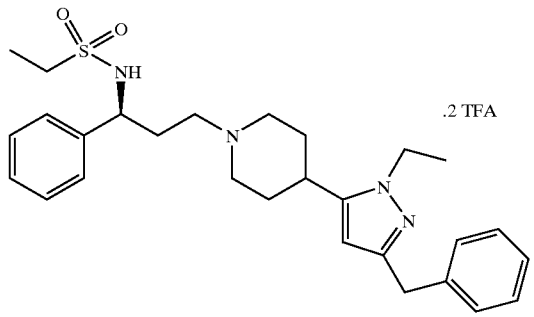

| | | |
|---|---|---|
| 4C: N-{(1S)-3-[4-(3-benzyl-1-ethyl-1H-pyrazol-5-yl)piperidin-1-yl]-1-phenylpropyl}thiophene-2-sulfonamide, bis trifluoroacetate salt | 549 (M + H) | 1.32 min |

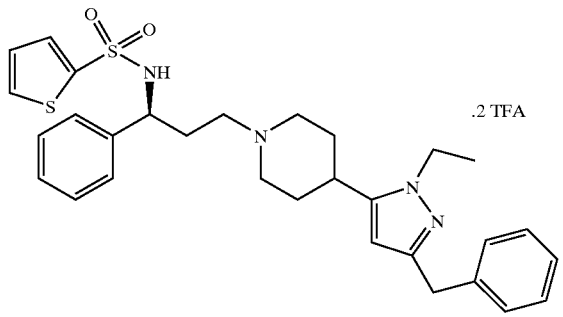

EXAMPLE 5A

2(+/−)-(N-[1(S)-1-phenyl-3-(4-[3-benzyl-1-ethyl(1H-pyrazol-5-yl)]piperidin-1-yl)propyl]amino) butanoic acid, tris-TFA salt

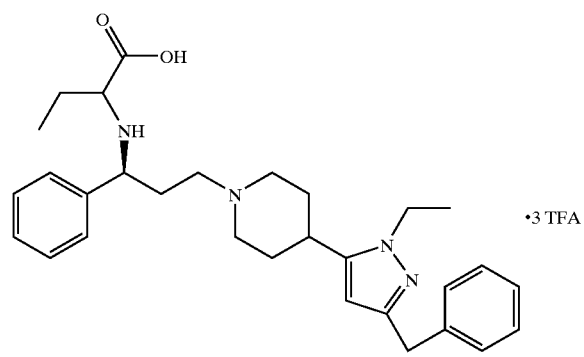

To a solution of the title amine from Example 1, Step G (0.08 mmol, 41 mg), 2-oxobutanoic acid (0.3 mmol, 30 mg) and triethylamine (0.4 mmol, 56 µL) in 2 mL of DCM was added NaBH(OAc)$_3$ (0.3 mmol, 96 mg). The reaction mixture was sonicated briefly and allowed to stand at ambient temperature for 16 h. Methanol (0.5 mL) was added to the reaction, and the mixture was loaded onto a Varian Bond Elut® SCX ion-exchange cartridge (2 g) and washed with 25 mL of methanol. The product was eluted with 25 mL of 2M ammonia in methanol. The solvent was removed under a stream of nitrogen, and the residue was purified by reverse-phase chromatography. Lyophilization afforded the title compound as a white solid. MS (ESI): m/z 489 (M+1). HPLC B: 1.05, 1.11 min.

EXAMPLES 5B–5D

The following compounds were prepared from the title compound in Example 1, Step G3 by an analogous procedure as described in Example 5A.

| Example No. | MS (ESI) | HPLC B |
|---|---|---|
| 5B: N-{(1S)-3-[4-(3-benzyl-1-ethyl-1H-pyrazol-1-5-yl)piperidin-1-yl]-1-phenylpropyl}isoleucine, tris-TFA salt | 517 (M + H) | 1.19, 1.43, 1.47 |
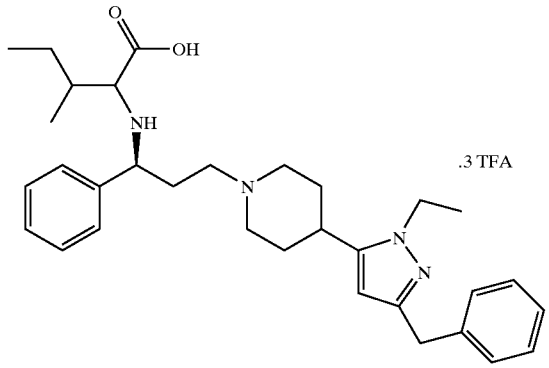
| | | |
|---|---|---|
| 5C: ({(1S)-3-[4-(3-benzyl-1-ethyl-1H-pyrazol-5-yl)piperidin-1-yl]-1-phenylpropyl}amino)(2-furyl)acetic acid, tris-TFA salt | 527 (M + H) | 1.15, 1.33 |
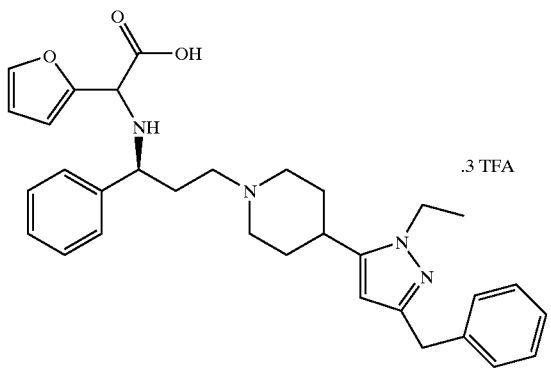
| | | |
|---|---|---|
| 5D: 3-[1-({(1S)-3-[4-(3-benzyl-1-ethyl-1H-pyrazol-5-yl)piperidin-1-yl]-1-phenylpropyl}amino)ethyl]benzoic acid, tris-TFA salt | 551 (M + H) | 1.22 min |
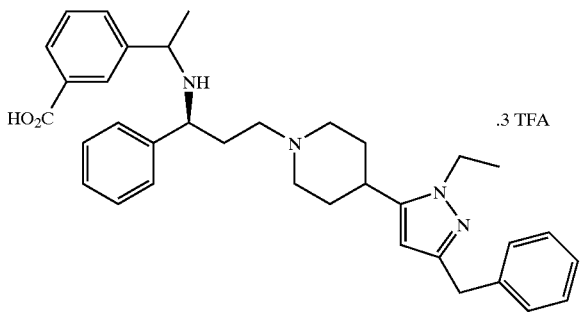

-continued

| Example No. | MS (ESI) | HPLC B |
|---|---|---|
| 5E: 4-[1-({(1S)-3-[4-(3-benzyl-1-ethyl-1H-pyrazol-5-yl)piperidin-1-yl]-1-phenylpropyl}amino)ethyl]benzoic acid tris-TFA salt | 551 (M + H) | 1.24 min |
| 5F: 2-{(1S)-3-[4-(3-benzyl-1-ethyl-1H-pyrazol-5-yl)piperidin-1-yl]-1-phenylpropyl}-3-methylisoindolin-1-one bis-TFA salt | 533 (M + H) | 1.81 min |
| 5G: 1-[1-({(1S)-3-[4-(3-benzyl-1-ethyl-1H-pyrazol-5-yl)piperidin-1-yl]-1-phenylpropyl}amino)methyl]cyclohexane carboxylic acid, tris-TFA salt | 543 (M + H) | 1.35 min |

EXAMPLE 6

N-[1(S)-1-phenyl-3-(4-[2-ethyl-4,5,6,7-tetrahydropyrazolo(1,5-α)pyridin-3-yl]piperidin-1-yl)propyl]cyclobutanecarboxamide, bis-TFA salt

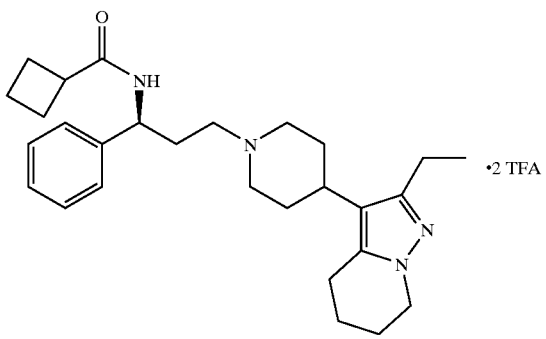

Step A: Methyl (3S)-3-amino-3-phenylpropionate

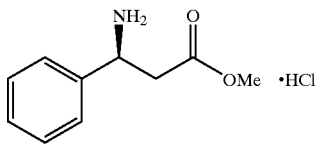

The title compound was obtained as a white solid from the title compound in Example 1, Step A, as described in WO 00/39125, p. 56.

Step B: Methyl (3S)-3-[(cyclobutylcarbonyl)amino]-3-phenylpropanoate

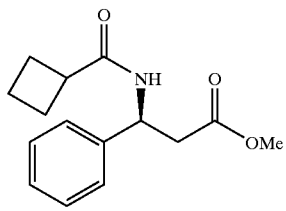

To a solution of the amino ester from Example 6, Step A (4.2 mmol, 896 mg) and cyclobutanecarboxylic acid (5.0 mmol, 476 μL) in 10 mL of DCM containing N,N-diisopropylethylamine (12.5 mmol, 2.17 mL) was added 1-(3-dimethylamino)propyl-3-ethylcarbodiimide hydrochloride (5.0 mmol, 958 mg). After 16 h the reaction mixture was washed with H$_2$O (10 mL), 1 M citric acid (10 mL) and saturated NaHCO$_3$ (10 mL). The organic phase was dried with MgSO$_4$ and the solvent removed under reduced pressure to afford the product as a white solid. MS (ESI): m/z 485 (M+H). HPLC B: 1.58 min.

Step C: N-[(1S)-3-Oxo-1-phenylpropyl]cyclobutanecarboxamide

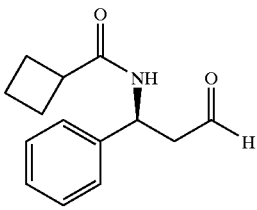

The compound was obtained from the title compound in Example 6, Step B, as described in WO 00/39125, p. 58. The product was further purified on silica gel eluting with 20% EtOAc/hexanes, affording the title compound as a slightly green oil. MS (ESI): m/z 232 (M+1). HPLC B: 1.21 min (br).

Step D: 4-(2-Ethyl-4,5,6,7-tetrahydropyrazolo[1,5-α]pyridin-3-yl) piperidine, HCl salt

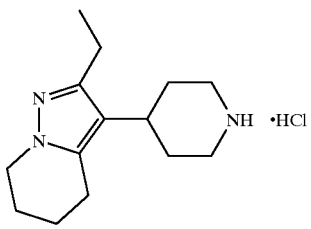

Step 1: 1-Chloro-5,7-nonanedione

To a suspension of NaH (60% dispersion in mineral oil: 8.88 g) in THF (250 mL) was added a mixture of 2-butanone (7.98 g) and methyl 5-chlorovalerate (50.0 g) in THF (100 mL) dropwise via cannula at 0° C. The mixture was stirred at 0° C. for 10 min and at rt for 24 h. After the reaction was quenched with 2 N—HCl (200 mL), the aqueous layer was extracted with EtOAc (3×). Concentration of the combined organic phase gave a brown colored oil, which was purified by fractional vacuum distillation. The title compound was collected in the temperature range between 95° C. and 110° C. at 10 mmHg. $^1$H NMR (500 MHz, CDCl$_3$) δ 1.14 (t, 3H, J=7.4 Hz), 1.65–1.90 (m, 4H), 2.30–2.60 (m, 4H), 3.50–3.60 (m, 2H), 5.51 (s, 1H).

Step 2: 2-Ethyl-4,5,6,7-tetrahydropyrazolo[1,5-α]pyridine

To a solution of 1-chloro-5,7-nonanedione (14.74 g, from Step 1) in a mixture of CH$_3$CN (100 mL) and H$_2$O (33 mL) was added 4.87 mL of hydrazine. After refluxing for 18 h, the reaction mixture was partitioned between EtOAc and aqueous NaHCO$_3$ (saturated). Aqueous layer was extracted with EtOAc (3×). Combined organic phase was washed with brine and dried over anhydrous MgSO$_4$. After concentration, the residue was purified by flash chromatography with 20% EtOAc in hexanes followed by 50% EtOAc in hexanes to give the title compound as a viscous oil. $^1$H NMR (500 MHz, CDCl$_3$) δ 1.24 (t, 3H, J=7.5 Hz), 1.79–1.85 (m, 2H), 1.95–2.05 (m, 2H), 2.62 (q, 2H, J=7.8 Hz), 2.75 (t, 2H, J=6.4Hz), 4.08 (t, 2H, J=6.1 Hz), 5.78 (s, 1H).

Step 3: 3-Bromo-2-ethyl-4,5,6,7-tetrahydropyrazolo[1,5-α]pyridine

To a solution of 2-ethyl-4,5,6,7-tetrahydropyrazolo[1,5-α]pyridine (4.12 g, from Step 2) in EtOH (25 mL) was added Br$_2$ (1.42 mL) dropwise at 0° C. The reaction was stirred at 0° C. for 20 min. The reaction mixture was partitioned between EtOAc and aqueous NaHCO$_3$ (saturated). Aqueous layer was extracted with EtOAc (3×). Combined organic phase was washed with brine and dried over anhydrous MgSO$_4$. After concentration, the residue was purified by flash chromatography with 10% EtOAc in hexanes followed by 20% EtOAc in hexanes to give the title compound as a viscous oil. $^1$H NMR (500 MHz, CDCl$_3$) δ 1.25 (t, 3H, J=7.5 Hz), 1.80–1.90 (m, 2H), 1.95–2.05 (m, 2H), 2.55–2.70 (m, 4H), 4.07 (t, 2H, J=6.0 Hz).

Step 4: 1-(t-Butoxycarbonyl)-4-hydroxy-4-(2-ethyl-4,5,6,7-tetrahydropyrazolo[1,5-α]pyridin-3-yl) piperidine To a solution of 3-bromo-2-ethyl-4,5,6,7-tetrahydropyrazolo[1,5-α]pyridine (4.01 g, 17.6 mmol, from Step 3) in THF (20 mL) was added t-BuLi (1.7 M in pentane, 22.8 mL, 38.7 mmol) dropwise at −78° C. After stirring at −78° C. for 30 min., was added tert-butyl 4-oxo-1-piperidinecarboxylate (3.51 g, 17.6 mmol) in THF (10 mL) dropwise at −78° C. The mixture was stirred at −78° C. for 10 min. and at rt for 4 h. After the reaction was quenched with aqueous NH$_4$Cl, the mixture was partitioned between EtOAc and water. Aqueous layer was extracted with EtOAc (3×). Combined organic phase was washed with brine and dried over anhydrous MgSO$_4$. Concentration was followed by purification by flash chromatography (hexanes: EtOAc= 1:1, then 100% EtOAc) to give the title compound as a foamy solid. $^1$H NMR (500 Mz, CDCl$_3$): δ 1.26 (t, 3H, J=7.4 Hz), 1.49 (s, 9H), 1.75–1.90 (m, 4H), 1.90–2.10 (m, 4H), 2.76 (q, 2H, J=7.6 Hz), 2.89 (t, 2H, J=6.4 Hz), 3.10–3.20 (br, 2H), 3.85–4.05 (br, 2H), 4.09 (t, 2H, J=6.2 Hz). ESI-MS 276 (M-t-Bu-H$_2$O+H); HPLC C: 2.05 min.

Step 5: 1-(t-Butoxycarbonyl)-4-(2-ethyl-4,5,6,7-tetrahydropyrazolo[1,5-α]pyridin-3-yl)-[1,2,3,6] tetrahydropyridine To a solution of 1-(t-butoxycarbonyl)-4-hydroxy-4-(2-ethyl-4,5,6,7-tetrahydropyrazolo[1,5-α]pyridin-3-yl) piperidine (2.47 g, 7.08 mmol, from Step 4) in toluene (20 mL) was added (methoxycarbonylsulfamoyl)-triethylammonium hydroxide inner salt (2.03 g, 8.50 mmol). After stirring at 80° C. for 18 h, the mixture was partitioned between EtOAc and aq. NaHCO$_3$. Aqueous layer was extracted with EtOAc (3×). Combined organic phase was washed with brine and dried over anhydrous MgSO$_4$. Concentration was followed by purification by flash chromatography (hexanes: EtOAc=4:1, then 1:1) to give the title compound as a white solid. $^1$H NMR (500 MHz, CDCl$_3$): δ 1.22 (t, 3H, J=7.5 Hz), 1.50 (s, 9H), 1.80–1.85 (m, 2H), 1.97–2.05 (m, 2H), 2.32 (br s 2H), 2.61 (q, 2H, J=7.5 Hz), 2.69 (t, 2H, J=6.2 Hz), 3.55–3.63 (m, 2H), 4.01 (br s), 4.08 (t, 2H, J=6.2 Hz). 5.50 (br s, 1H)

Step 6: 1-(t-Butoxycarbonyl)-4-(2-ethyl-4,5,6,7-tetrahydropyrazolo[1,5-α]pyridin-3-yl)-piperidine A solution of 1-(t-butoxycarbonyl)-4-(2-ethyl-4,5,6,7-tetrahydropyrazolo[1,5-α]pyridin-3-yl)-[1,2,3,6] tetrahydropyridine (1.17 g, from Step 5) in MeOH (40 mL) was hydrogenated using Pd(OH)$_2$ (300 mg) under atmospheric H$_2$ for 18 h. The mixture was filtered through celite. Concentration was followed by purification by flash chromatography (hexanes: EtOAc =4:1, 1:1, then 100% EtOAc) to give the title compound as a viscous oil. $^1$H NMR (500 MHz, CDCl$_3$): δ1.23 (t, 3H, J=7.5 Hz), 1.49 (s, 9H), 1.55–1.75 (m, 4H), 1.75–1.85 (m, 2H), 1.90–2.02 (m, 2H), 2.50–2.63 (m, 3H), 2.63–2.80 (m, 4H), 4.07 (t, 2H, J=6.1 Hz), 4.10–4.30 (br, 2H).

Step 7: 4-(2-Ethyl-4,5,6,7-tetrahydropyrazolo[1,5-α] pyridin-3-yl)-piperidine, HCl salt To a solution of 1-(t-butoxycarbonyl)-4-(2-ethyl-4,5,6,7 tetrahydropyrazolo[1,5-α]pyridin-3-yl)-piperidine (1.41 g, from Step 6) in MeOH (15 mL) was added a saturated HCl solution in MeOH (15 mL) at 0° C. After stirring at rt or 3 h, the reaction mixture was concentrated to give the title compound as a foamy solid, which was used for the next step without further purification.

Step E: N-[1(S)-1-phenyl-3-(4-[2-ethyl-4,5,6,7-tetrahydropyrazolo(1,5-α)pyridin-3-yl]piperidin-1-yl)propyl]cyclobutanecarboxamide, bis-TFA salt

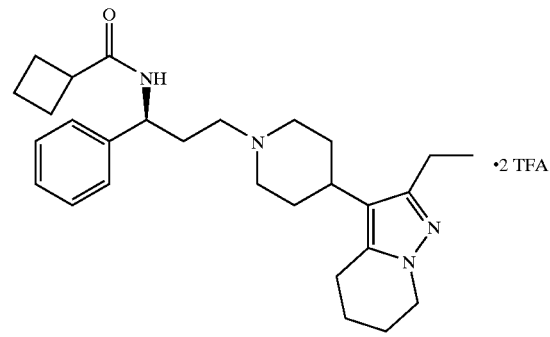

To a solution of the title aldehyde from Example 6, Step C (0.1 mmol, 23 mg), 4-(2-Ethyl-4,5,6,7-tetrahydropyrazolo [1,5-α]pyridin-3-yl) piperidine, HCl salt (Example 6, Step D, 0.1 mmol, 31 mg) and N,N-diisopropylethylamine (0.4 mmol, 70 µL) in 2 mL of DCM was added NaBH(OAc)$_3$ (0.3 mmol, 65 mg). The reaction mixture was sonicated briefly and allowed to stand at ambient temperature for 2 h, after which time HPLC analysis revealed the reaction was complete. Solvent was removed under a stream of nitrogen. The residue was taken up in 1:1 dioxane/H$_2$O and purified by reverse-phase HPLC. Lyophilization of the product afforded the title compound as a white solid. MS (ESI): m/z 449 (M+H). HPLC B: 1.04 min.

EXAMPLE 7

N-[1(S)-1-phenyl-3-(4-[3-ethyl-1-(4-[ethylsulfonyl] benzyl)-(1H-pyrazol-5-yl)-piperidin-1-yl)propyl] cyclobutanecarboxamide, bis-TFA salt

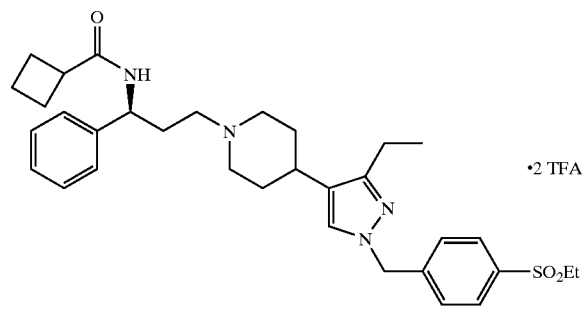

Step A: N-tert-Butoxycarbonyl-4-piperidylacetaldehyde

A solution of oxalyl chloride (2.4 mL, 27.5 mmol) in 125 mL DCM was cooled to −78° C. and DMSO (3.3 mL, 47.1 mmol) was added slowly. After 10 min a solution of 2-(N-tert-butoxycarbonyl-4-piperidyl)ethanol (4.5 grams, 19.6 mmol) in 10 mL DCM was added. The mixture was stirred for 20 min then triethylamine (13.6 mL, 98.1 mmol) was added and the mixture was warmed to room temperature. After 30 min the mixture was diluted with ethyl acetate and washed with water (3×). The organic portion was dried over sodium sulfate and concentrated. Flash chromatography (3/1 hexane/EtOAc) afforded the desired aldehyde. $^1$H NMR (400 MHz, CDCl$_3$). δ 1.13–1.43 (m, 2H), 1.48 (s, 9H), 1.68–1.77 (m, 2H), 2.04–2.11 (m, 1H), 2.38–2.41 (d, 2H), 2.71–2.8 (m, 2H), 4.04–4.14 (m, 2H), 9.8 (s, 1H).

Step B: 3-Ethyl-4-(N-t-butoxycarbonylpiperid4-yl)-1H-pyrazole

A solution of N-tert-Butoxycarbonyl-4-piperidylacetaldehyde (4.5 grams, 19.8 mmol, from Step A), and morpholine (1.7 mL, 19.8 mmol) in 100 mL benzene was refluxed using a dean-stark apparatus. After refluxing over night the mixture was concentrated to provide the examine. The crude examine was dissolved in 40 mL DCM and the solution was cooled to 10° C. Propionyl chloride (1.7 mL, 19.8 mmol) and then triethylamine (1.4 mL, 9.9 mmol) were added. The mixture was gradually warmed to room temperature and stirred for 40 h then concentrated. The residue was dissolved in 60 mL of ethanol and hydrazine (6.2 mL, 198 mmol) was added. The solution was refluxed for 5 h. The solvent was removed and ethyl acetate was added. The organic was washed with water and sat'd sodium chloride then dried over magnesium sulfate and concentrated. Flash chromatography (0.5% MeOH/DCM →2% MeOH/DCM) afforded the title compound. $^1$H NMR (400 MHz, CDCl$_3$): δ1.25–1.31 (t, 3H), 1.44–1.57 (m, 1H), 1.46 (s, 9H), 1.78–1.83 (s, 2H), 2.53–2.6 (m, 1H), 2.62–2.7 (q, 2H), 2.77–2.82 (m, 2H), 4.12–4.23 (m, 2H), 7.32 (s, 1H).

Step C: 4-(Ethylthio)benzyl chloride

Aluminum chloride (2 g, 15 mmol) was suspended in 8 mL 1,2-dichloroethane and the solution was cooled to 5° C. Dimethoxymethane (0.69 mL, 7.8 mmol) over 10 min. Ethylphenylsulfide (0.88 mL, 6.5 mmol) was added and the mixture was warmed to rt. After 15 h ice water was added and the mixture was extracted with methylene chloride (3×). The combined organic fractions were dried over magnesium sulfate and concentrated. The crude material was used directly in the next step.

Step D: tert-Butyl 4-{3-ethyl-1-[4-(methylthio)benzyl]-1H-pyrazol-4-yl }-piperidine-1-carboxylate A solution of 3-ethyl-4-(N-t-butoxycarbonylpiperid-4-yl)-1H-pyrazole (0.83 g, 2.97 mmol, from Step B) in 4 mL DMF was cooled to 0° C. and sodium hydride (155 mg, 3.87 mmol, 60% dispersion in mineral oil) was added cautiously. The mixture was warmed to rt and 4-(ethylthio)benzyl chloride (crude material from Step C) in 6 mL DMF was added. The mixture was stirred for 14 h. The mixture was concentrated and the residue was taken up in methylene chloride. The solution was washed with water and sat'd sodium chloride then dried over magnesium sulfate and concentrated. Flash chromatography (40 g silica, 4/1 hexane/EtOAc) afforded the product.

Step E: 4-{3-Ethyl-1-[4-(ethylsulfonyl)benzyl]-1H-pyrazol-4-yl}piperidine trifluoroacetate

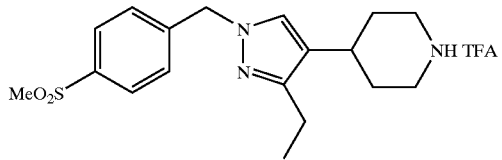

A solution of tert-Butyl 4-{3-ethyl-1-[4-(methylthio)benzyl]-1H -pyrazol-4-yl}-piperidine-1-carboxylate (300 mg, 0.7 mmol, from Step D) in 8 mL methanol was cooled to 5° C. Oxone® (645 mg, 1.05 mmol) in 3 mL water was added and the mixture was warmed to rt. After 50 min the reaction was quenched with sat'd sodium thiosulfite. The mixture was extracted with methylene chloride (4×) and the organic portions were dried over magnesium sulfate then concentrated. Flash chromatography (45 g silica, 3/1 methylene chloride/ether) gave the product. $^1$H NMR (500 MHz, CDCl$_3$). δ 1.07–1.17 (m, 4H), 1.25–1.37 (m, 2H), 1.33 (s, 9H), 1.65–1.72 (br d, 2H), 2.4–2.55 (m, 3H), 2.6–2.75 (m, 2H), 2.9–2.97 (q, 2H), 3.99–4.1 (m, 2H), 5.18 (s, 2H), 7.05 (s, 1H), 7.17–7.19 (d, 2H), 7.67–7.69 (d, 2H). The material was stirred in 1/1 methylene chloride/TFA for 1 h. Removal of solvent followed by drying under vacuum gave the desired trifluoroacetate.

Step F: N-[1(S)-1-phenyl-3-(4-[3-ethyl-1-(4-[ethylsulfonyl]benzyl)-(1H-pyrazol-5-yl)-piperidin-1-yl)propyl]cyclobutanecarboxamide, bis-TFA salt

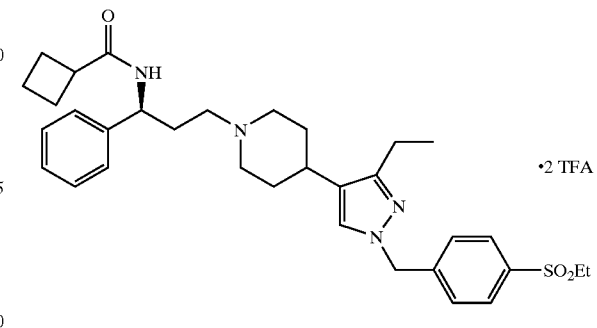

To a solution of the title compound from Example 6, Step C (0.1 mmol, 23 mg), 4-(3-ethyl-1-[4-(ethylsulfonyl)benzyl]-1H-pyrazol-4-yl)piperidine trifluoroacetate (Example 7, Step E, 0.13 mmol, 93 mg) and N,N-diisopropylethylamine (0.6 mmol, 110 μL) in 2 mL of DCM was added NaBH(OAc)$_3$ (0.3 mmol, 65 mg). The reaction mixture was sonicated briefly and allowed to stand at ambient temperature for 2 h, after which time HPLC analysis revealed the reaction was complete. Solvent was removed under a stream of nitrogen, and the residue was resuspended in 1:1 dioxane/H$_2$O and purified by reverse-phase HPLC. Lyophilization of the product afforded the title compound as a white solid. MS(ESI): m/z 577 (M+H). HPLC B: 1.47 min.

EXAMPLE 8

N-[1(S)-1-phenyl-3-(4-[1,3-diethyl-5-methyl(1H-pyrazol-4-yl]piperidin-1-yl)propyl]cyclobutanecarboxamide, bis-TFA salt

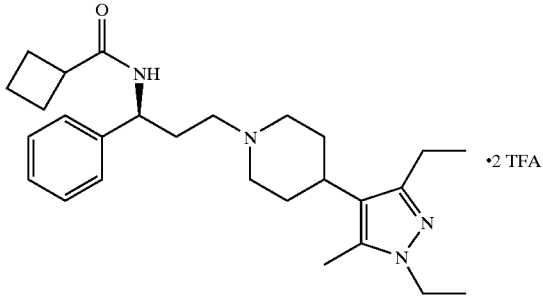

Step A: (±)-Hex-4-yn-3-ol

Propionaldehyde (18.0 mL, 0.25 mol) was added to 500 mL of 0.5 M 1-propynylmagnesium bromide solution in THF at 0° C. The resulting mixture was warmed to rt and stirred for 18 h. The reaction was quenched by pouring it into a well stirred mixture of 300 g of sat'd $NH_4Cl$ and 300 g of ice. The resulting mixture was extracted with 2×1 L of ether. The ether extracts were dried over $MgSO_4$, combined and concentrated to afford the title compound which was used without further purification.

Step B: Hex-4-yn-3-one

A mixture of 24 g (0.25 mol) of (±)-hex-4-yn-3-ol (from Step A), 40 g (0.34 mol) of N-methylmorpholine N-oxide and 75 g of 4 A molecular sieves in 250 mL of $CH_2Cl_2$ at 0° C. was treated with 2 g (5.7 mmol) of tetrapropylammonium perruthenate. The resulting mixture was warmed to rt and stirred for 1 h. The reaction was filtered through a pad of 400 g of silica gel; the flask and pad were rinsed well with $CH_2Cl_2$ (400 mL). The filtrate was concentrated. Distillation at reduced pressure (45 mmHg) afforded the title compound, bp=70–75° C.

Step C: 1,3-Diethyl-5-methylpyiazole

A solution of 18.9 g (0.2 mol) of hex-4-yn-3-one (from Step B) in 120 mL of n-butanol was treated with 40 mL (0.227 mol) of ethyl hydrazine, 34% solution in water. The resulting mixture was heated at reflux for 1.5 h, then cooled to rt. The mixture was concentrated to ~150 mL volume; this was partitioned between 1 L of ether and 250 mL of water. The layers were separated and the organic layer was dried and concentrated to afford the title compound, which was used without further purification. $^1$H-NMR (400 MHz) δ 1.22 (t, J=7.6, 3H), 1.37 (t, J=7.2, 3H), 2.23 (s, 3H), 2.59 (q, J=7.6, 2H), 4.01 (q, J=7.2, 2H), 5.81 (s, 1H).

Step D: 1,3-Diethyl-4-iodo-5-methylpyrazole

A mixture of 13.2 g (95.7 mmol) of 1,3-diethyl-4-5-methylpyrazole (from Step C) and 1.50 g (3.7 mmol) of sorbitan monopalmtate in 200 mL of 2.5 N NaOH was treated with 44 g (0.17 mol) of iodine. Additional portions of sorbitan monopahnitate and iodine were added after 30 min and 60 min. The mixture was partitioned between 1 L of ether and 500 mL of water and the layers were separated. The organic layer was washed with 500 mL of 5% $Na_2S_2O_3$, dried over $MgSO_4$ and concentrated. Chromatography on a Biotage 75L using 9:1 heptane/EtOAc as the eluant afforded the title compound. $^1$H-NMR (400 MHz) δ1.22 (t, J=7.6, 3H), 1.36 (t, J=7.2, 3H), 2.27 (s, 3H), 2.58 (q, J=7.6, 2H), 4.10 (q, J=7.2, 2H).

Step E: 1,3-Diethyl-4-(4-pyridyl)-5-methylpyrazole

A mixture of 17.05 g (64.6 mmol) of 1,3-diethyl-4-iodo-5-methylpyrazole (from Step D) and 11.9 g (105.4 mmol) of pyridine 4-boronic acid in 300 mL of dioxane was treated with a solution of 44 g (392 mmol) of potassium t-butoxide in 100 mL of water. The resulting mixture was treated with 3.75 g (3.2 mmol) of tetrakis(triphenylphosphine)palladium (0), put under an argon atmosphere and heated at 100° C. for 18 h. The mixture was cooled and partitioned between 1 L of ether and 500 mL of water. The organic layer was separated, dried over $MgSO_4$ and concentrated. Flash chromatography on a Biotage 75S afforded the title compound. $^1$H-NMR (500 MHz) δ 1.19 (t, J=7.5, 3H), 1.48 (t, J=7.5, 3H), 2.27 (s, 3H), 2.67 (q, J=7.5, 2H), 4.09 (q, J=7.5, 2H), 7.18 (dd, J=2.0, 4.5, 2H), 8.60 (dd, J=2.0, 4.5, 2H).

Step F: 1-Benzyl-4-(1,3-diethyl-5-methyl-pyrazol-4-yl)-1,2,3,6-tetrahydropyridine A solution of 7.55 g (35.0 mmol) of 1,3-diethyl-4-(4-pyridyl)-5-methylpyrazole (from Step E) and 4.20 mL (35.0 mmol) of benzyl bromide in 50 mL of MeOH was heated at reflux for 30 min. The mixture was cooled to 0° C. and treated with 2.65 g (70.0 mmol) of sodium borohydride in portions so as to maintain the internal at ~0° C. The resulting mixture was stirred cold for 30 min, then concentrated. The residue was partitioned between 300 mL of $CH_2Cl_2$ and 150 mL of 1.0 N NaOH and the layers were separated. The organic layer was dried over $MgSO_4$. The organic layer was extracted with 300 mL of ether; the extract was dried over $MgSO_4$. The organic layers were combined and concentrated. Chromatography on a Biotage 75L using 9:1 v/v heptane/acetone as the eluant afforded the title compound. $^1$H-NMR (400 MHz) δ 1.19 (t, J=7.6, 3H), 1.37 (t, J=7.6, 3H), 2.17 (s, 3H), 2.31–2.35 (m, 2H), 2.58 (q, J=7.6, 2H), 2.66 (t, J=5.6, 2H), 3.13 (app q, J=2.8, 2H), 3.65 (s, 2H), 4.01 (q, J=7.6, 2H), 5.46–5.48 (m, 1H), 7.26–7.39 (5H).

Step G: 4-(1,3-Diethyl-5-methyl-[1H-pyrazol-4-yl])piperidine

A mixture of 5.70 g (18.4 mmol) of 1-benzyl-4-(1,3-diethyl-5-methyl-pyrazol-4-yl)-1,2,3,6-tetrahydropyridine (from Step F), 25 g (0.4 mol) of ammonium formate and 2.0 g of 20% palladium hydroxide on carbon in 100 mL of methanol was heated at reflux for 1 h. The mixture was cooled and filtered through a pad of Celite. The filtrated was concentrated. The residue was partitioned between 200 mL of $CH_2Cl_2$ and 100 mL of 10% $NH_4OH$ and the layers were separated. The organic layer was dried over $MgSO_4$. The aqueous layer was extracted with 2×200 mL of $CH_2Cl_2$; the extracts were dried over $MgSO_4$ and all were combined and concentrated. Chromtography on a Biotage 40L using 40:1:0.1, then 20:1:0.1, then 10:1:0.1 v/v/v $CH_2Cl_2$/MeOH/$NH_4OH$ as the eluant afforded the title compound. $^1$H-NMR (500 MHz) δ 1.21 (t, J=7.5, 3H), 1.35 (t, J=7.5, 3H), 1.64 (br d, J=12.5, 2H), 1.78 (dq, J=4.0, 13.0, 2H), 2.24 (s, 3H), 2.50 (tt, J=4.0, 12.5, 1H), 2.62 (q, J=7.5, 2H), 2.69 (dt, J=2.5, 12.0, 2H), 3.16 (app d, J=12.0, 2H), 4.02 (q, J=7.5, 2H); ESI-MS 222 (M+H).

Step H: N-[1(S)-1-phenyl-3-(4-[1,3-diethyl-5-methyl(1H-pyrazol-4-yl]piperidin-1-yl)propyl] cyclobutanecarboxamide, bis-TFA salt

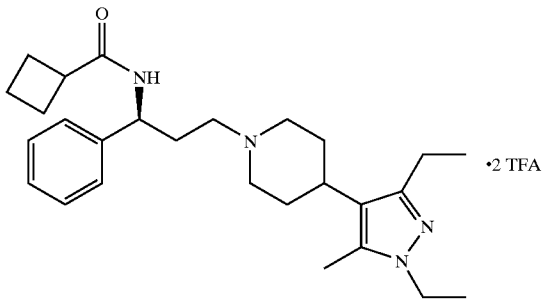

To a solution of the title aldehyde from Example 6, Step C (0.1 mmol, 23 mg), 4-(1,3-diethyl-5-methyl-[1H-pyrazol-4-yl])piperidine (Example 8, Step G, 1.1 mmol, 24 mg) and N,N-diisopropylethylamine (0.17 mmol, 30 µL) in 2 mL of DCM was added NaBH(OAc)₃ (0.3 mmol, 65 mg). The reaction mixture was sonicated briefly and allowed to stand at ambient temperature for 2 h, after which time HPLC analysis revealed the reaction was complete. Solvent was removed under a stream of nitrogen, and the residue was resuspended in 1:1 dioxane/H₂O and purified by reverse-phase HPLC. Lyophilization of the product afforded the title compound as a white solid. MS (ESI): m/z 437 (M+H). HPLC B: 1.04 min.

EXAMPLE 9

N-[1(S)-1-(3-fluorophenyl)-3-(4-[2-ethyl-4,5,6,7-tetrahydropyrazolo(1,5-α)pyridin-3-yl]piperidin-1-yl)propyl]cyclobutanecarboxamide, bis-TFA salt

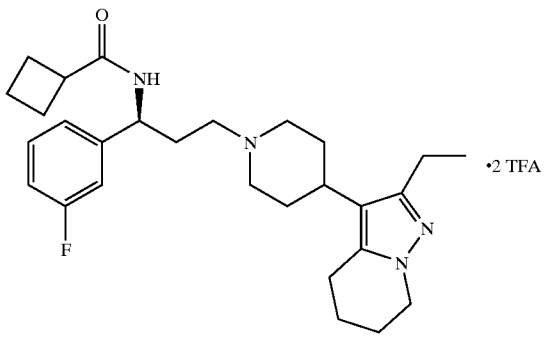

Step A: Methyl (3S)-3-amino-3-phenylpropionate, HCl salt

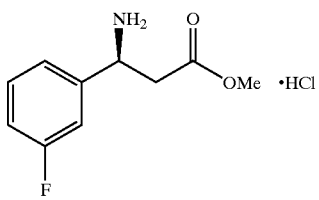

The title compound was prepared as described in WO 00/39125, pp. 58–60. ¹H NMR (500 MHz, CDCl₃): δ 7.36–7.41 (m, 1H), 7.32–7.34 (m, 1H), 7.26–7.28 (m, 1H), 7.04–7.08 (m, 1H), 4.67 (t, 1H), 3.65 (s, 3H), 3.30–3.34 (m, 1H), 3.01–3.06 (overlapping m, 3H).

Step B: Methyl (3S)-3-[(cyclobutylcarbonyl) amino]-3-(3-fluorophenyl)propanoate

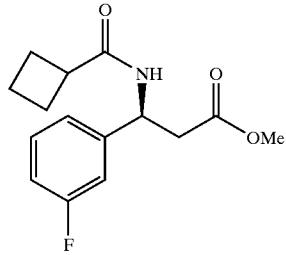

To a solution of the title compound in Example 9, Step A (1.5 mmol, 350 mg), cyclobutylcarboxylic acid (2.5 mmol, 250 mg) and N,N-diisopropylethylamine (2.5 mmol, 435 µL) in 5 mL of DMF was added EDC (2.5 mmol, 479 mg). After 4 h 40 mL of DCM was added to the reaction mixture and the resulting solution was extracted with 50 mL of 1 M citrate and 50 mL of saturated NaHCO₃. The organic phase was dried with MgSO₄, filtered, and the solvent removed under reduced pressure. The residue was run through a silica plug eluting with DCM. Removal of solvent under reduced pressure afforded the title product as a clear oil. ¹H NMR (500 MHz, CDCl₃): δ 7.27–7.32 (m, 1H), 7.07 (d, J=7.8 Hz, 1H), 6.99 (d, J=10.1 Hz, 1H), 6.93–6.97 (m, 1H), 6.67 (br m, 1H), 5.40–5.44 (m, 1H), 3.64 (s, 3H), 3.05–3.09 (m, 1H), 2.89–2.93 (m, 1H), 2.81–2.85 (m, 1H), 2.22–2.32 (m, 2H), 2.16–2.21 (m, 2H), 1.87–2.01 (m, 2H). MS (ESI): m/z 280 (M+H). MS(ESI): m/z 280 (M+H). HPLC B: 1.69 min.

Step C: N-[(1S)-3-Oxo-1-phenylpropyl] cyclobutanecarboxamide

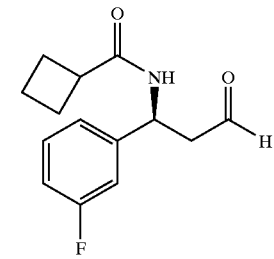

To a stirring solution of the methyl ester from Example 9, Step B (1.2 mmol, 330 mg) in 10 mL of DCM cooled to –78° C. was added dropwise over 20 min. diisobutylaluminum hydride (2.4 mmol, 2.4 mL of 1 M solution in DCM). The solution was stirred at –78° C. for 2 h. Methanol (2 mL) cooled to –78° C. was canulated dropwise to the reaction mixture over 5 min. After 10 min. the reaction was allowed to warm to room temperature, during which time a white precipitate formed. DCM (30 mL) was added, and the solution was poured into 2 N HCl (50 mL). The organic phase was collected and the aqueous phase was extracted with DCM (2×25 mL). The combined organic phase was dried with MgSO₄ and the solvent removed under reduced pressure. The oily residue was dissolved in DCM and passed through a silica plug eluting with DCM. Removal of solvent under reduced pressure afforded the title compound as a clear oil. MS(ESI): m/z 250 (M+H). HPLC B: 1.31 min.

Step D: N-[1(S)-1-(3-fluorophenyl)-3-(4-[2-ethyl4,5,6,7-tetrahydropyrazolo(1,5-α)pyridin-3-yl]piperidin-5-yl)propyl]cyclobutanecarboxamide, bis-TFA salt

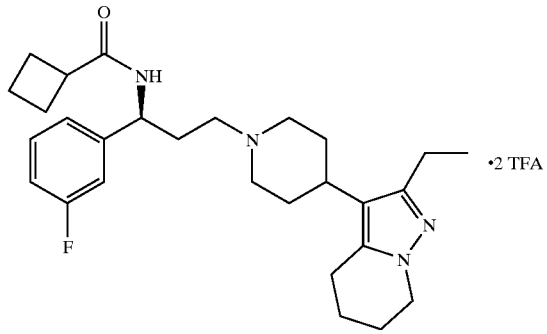

To a solution of the title aldehyde from Example 9, Step C (0.1 mmol, 25 mg), 4-(2-Ethyl-4,5,6,7-tetrahydropyrazolo[1,5-α]pyridin-3-yl) piperidine, HCl salt (Example 6, Step D, 0.1 mmol, 31 mg) and N,N-diisopropylethylamine (0.4 mmol, 70 μL) in DCM (2 mL) was added NaBH(OAc)$_3$ (0.15 mmol, 32 mg). The reaction mixture was sonicated briefly and allowed to stand at ambient temperature for 3 h. Solvent was removed under a stream of nitrogen, and the residue was resuspended in 1:1 dioxane/H$_2$O and purified by reverse-phase HPLC. Lyophilization of the product afforded the title compound as a white solid. MS (ESI): m/z 455 (M+H). BPLC B: 1.12 min.

EXAMPLE 10

N-[1(S)-1-(3-fluorophenyl)-3-(4-[3-benzyl-1-ethyl(1H-pyrazol-5-yl]piperidin-1-yl)propyl]cyclobutanecarboxamide, bis-TFA salt

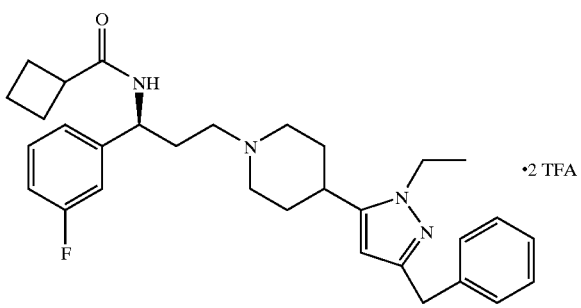

To a solution of the title aldehyde from Example 9, Step C (0.1 mmol, 25 mg), 4-(3-benzyl-1-ethylpyrazol-5-yl) piperidine, HCl salt (Example 1, Step E, 0.1 mmol, 34 mg) and N,N-diisopropylethylamine (0.4 mmol, 70 μL) in DCM (2 mL) was added NaBH(OAc)$_3$ (0.15 mmol, 32 mg). The reaction mixture was sonicated briefly and allowed to stand at ambient temperature for 3 h. Solvent was removed under a stream of nitrogen, and the residue was resuspended in 1:1 dioxane/H$_2$O and purified by reverse-phase HPLC. Lyophilization of the product afforded the title compound as a white solid. MS (ESI): m/z 503 (M+H). HPLC B: 1.62 min.

EXAMPLE 11

N-[1(S)-1-(3-fluorophenyl)-3-(4-[1,3-diethyl-5-methyl(1H-pyrazol-4-yl]piperidin-1-yl)propyl]cyclobutanecarboxamide, bis-TFA salt

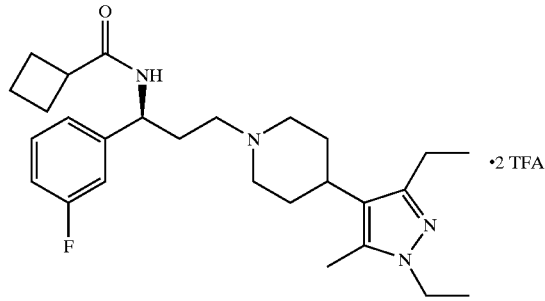

Step A: Methyl (3S)-3-[(tert-butoxycarbonyl)amino]-3-(3-fluorophenyl)propanoate

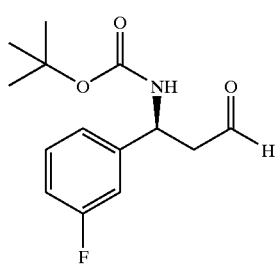

The compound was obtained from the title compound in Example 9, Step A as a white solid as described in WO 00/39125, p. 60. $^1$H NMR (500 MHz, CDCl$_3$): δ 7.27–7.35 (m, 1H), 7.10 (d, J=7.8 Hz, 1H), 7.04 (dd, J=9.9 Hz, 2.0 Hz, 1H), 6.95–7.0 (m, 1H), 5.58 (br s, 1H), 5.12 (br s, 1H), 3.66 (s, 3H), 2.8–2.95 (m, 2H), 1.46 (s, 9H). MS(ESI): m/z 320 (M+Na). HPLC B: 2.21.

Step B: tert-Butyl(1S)-3-oxo-1-(3-fluorophenyl)propylcarbamate

To a stirring solution of the methyl ester from Example 11, Step A (2.0 mmol, 594 mg) in 20 mL of dry DCM cooled to −78° C under nitrogen was added dropwise over 20 min. Diisobutylaluminum hydride (4 mmol, 4 mL of a 4 M solution in toluene). The reaction was stirred for 2 h at −78° C. after which time MeOH (4 mL) cooled to −78° C. was canulated into the reaction mixture. After 10 min. the solution was allowed to reach room temperature. DCM (30 mL) was added to the reaction, and the solution was poured into 60 mL of 2N HCl. The organic phase was collected and the aqueous phase was extracted with DCM (2×20 mL). The combined organic phase was dried with MgSO$_4$ and concentrated under reduced pressure. The aldehyde was further purified by flash chromatography on silica gel (40 g) using a step gradient of 0% to 16% EtOAc/hexanes, increasing in 4% increments. The aldehyde eluted in 12–16% EtOAc/hexanes, affording a white waxy solid. $^1$H NMR (500 MHz, CDCl$_3$): δ 9.76 (s, 1H), 7.28–7.4 (m, 1H); 7.11 (d, 1H, J=7.7 Hz); 7.04 (dd, 1H, J=9.8 Hz, 2.0 Hz), 6.96–7.02 (m, 1H), 5.25 (br s, 1H), 2.92–3.1 (2H, m), 1.45 (s, 9H). MS (ESI): m/z 250 (M+H).

Step C: (1S)-1-(3-fluorophenyl)-3-(4-[1,3-diethyl-5-methyl(1H-pyrazol-4-yl]piperidin-1-yl)propylamine, tris-HCl salt

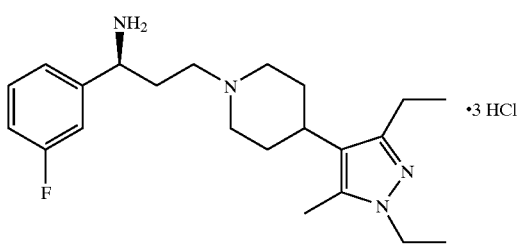

To a solution of the title compound from Example 10, Step B (0.8 mmol, 21 mg), 4-[1,3-diethyl-5-methyl(1H-pyrazol-4-yl]piperidine (Example 8, Step G, 0.1 mmol, 22 mg) and triethylamine (0.4 mmol, 56 μL) in 2 mL of DCM was added NaBH(OAc)$_3$ (0.15 mmol, 32 mg). The slurry was sonicated briefly and the reaction mixture was allowed to stand at ambient temperature for 16 h. The solvent was removed under a stream of nitrogen. The residue was taken up in 1:1 dioxane/H$_2$O and purified by reverse-phase chromatography (HPLC B: 1.36 min). The solvent was removed under reduced pressure and the residue was treated for 2 h at ambient temperature in 3 mL of a premixed solution of 1:8 (v/v) acetyl chloride/methanol. The solvent was removed under reduced pressure affording the title compound as a white solid. MS (ESI): m/z 473 (M+H). HPLC B: 0.58 min.

Step D: N-[1(S)-1-phenyl-3-(4-[3-benzyl-1-ethyl(1H-pyrazolyl]piperidin-5-yl)propyl] cyclobutanecarboxamide, bis-TFA salt

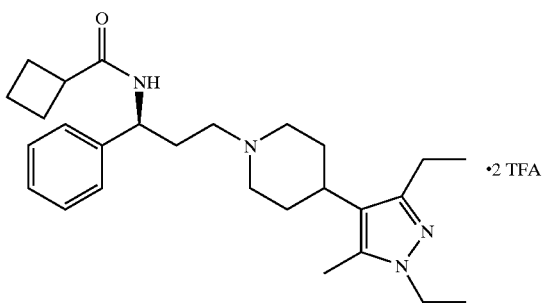

To a solution of the title compound from Example 10, Step C (0.06 mmol, 31 mg), cyclobutanecarboxylic acid (0.2 mmol, 20 μL) and N,N-diisopropylethylamine (0.34 mmol, 60 μL) in 2 mL of DCM was added EDC (0.19 mmol, 40 mg). The reaction mixture was allowed to stand at room temperature for 2 h, after which time the solvent was removed under a stream of nitrogen. The residue was taken up in 1:1 dioxane/H$_2$O and purified by reverse-phase chromatography. Lyophilization afforded the product as a white solid. MS(ESI): m/z 455 (M+H). HPLC B 1.12 min.

EXAMPLE 12

N-cyclopentyl-N'-{(1S)-3-[4-(2-ethyl-4,5,6,7-tetrahydropyrazolo[1,5-α]pyridin-3-yl)piperidin-1-yl]-1-phenylpropyl}urea bis(trifluoroacetate)

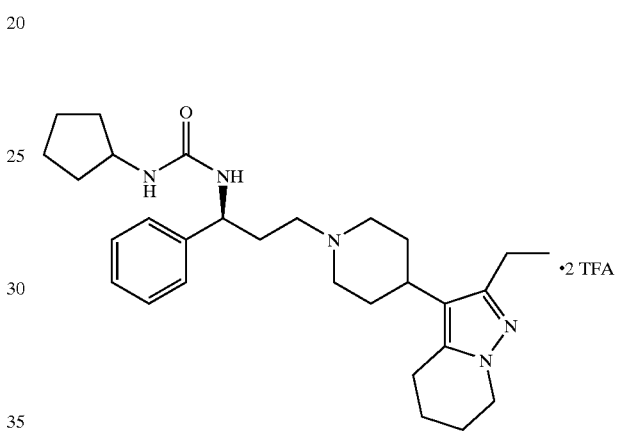

To the a solution of the title amine from Example 1, Step G (0.06 mmol, 31 mg) and DIEA (0.24 mmol, 42 μL) in 2 mL of DCM in an icebath was added p-nitrophenylchloroformate (0.07 mmol, 14 mg). After 1.5 h cyclopenylamine (0.12 mmol, 92 μL) was added to the reaction. Formation of a precipitate was observed, and 0.12 mmol of DIEA and 1 mL of DMF was added to the reaction, which was allowed to stand overnight. Methanol (0.5 mL) was added to the reaction, and the mixture was loaded onto a Varian Bond Elut® SCX ion-exchange cartridge (2 g) and washed with 25 mL of methanol. The product was eluted with 25 mL of 2M ammonia in methanol. The solvent was removed under a stream of nitrogen, and the residue was purified by reverse-phase chromatography. Lyophilization afforded the title compound as a white solid. MS (ESI): m/z 514 (M+1). HPLC B: 1.73 min.

EXAMPLES 13–16

The following compounds were prepared from the title compound in Example 1, Step G by an analogous procedure as described in Example 12.

| Structure | MS (ESI) | HPLC B |
|---|---|---|
| 13: 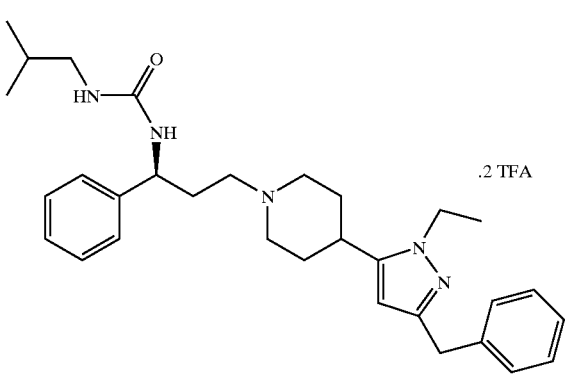 .2 TFA | 502 (M + H) | 1.70 min |
| 14: 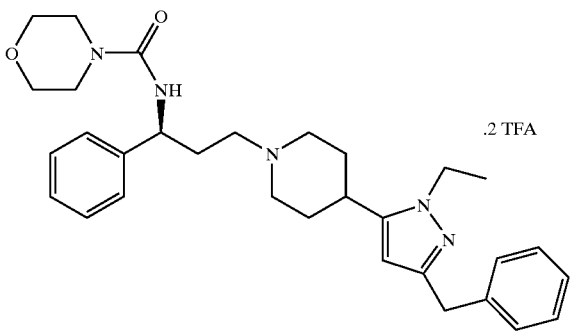 .2 TFA | 516 (M + H) | 1.41 min |
| 15: 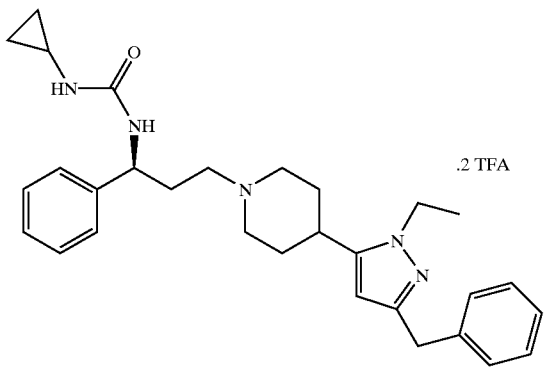 .2 TFA | 486 (M + H) | 1.46 min |
| 16: 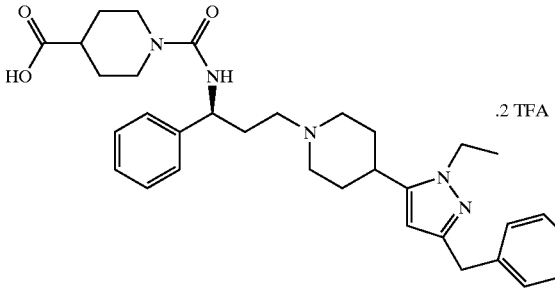 .2 TFA | 551 (M + H) | 1.24 min |

EXAMPLE 17

4-(3-benzyl-1-ethyl-1H-pyrazol-1-ium-5-yl)-1-((3S)-3-{[(cyclohexylamino)carbonyl]amino}-3-phenylpropyl)piperidinium bis(trifluoroacetate)

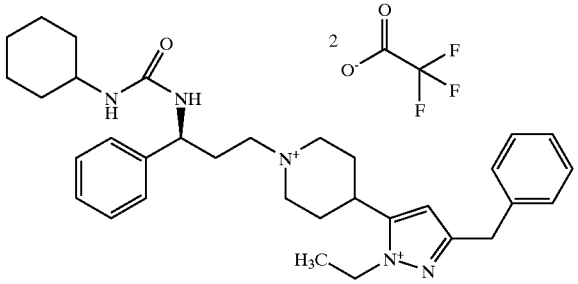

To the a solution of the title amine from Example 1, Step G (0.06 mmol, 31 mg) and DIEA (0.24 mmol, 42 µL) in 1 mL of DCM was added cyclohexylisocyanate (0.08 mmol, 10 mg). After 1 h the mixture was loaded onto a Varian Bond Elut® SCX ion-exchange cartridge (2 g) and washed with 25 mL of methanol. The product was eluted with 25 mL of 2M ammonia in methanol. The solvent was removed under a stream of nitrogen, and the residue was purified by reverse-phase chromatography. Lyophilization afforded 27 mg of the title compound as a white solid. MS (ESI): m/z 528 (M+1). HPLC B: 1.83 min.

EXAMPLE 18

4-(3-benzyl-1-ethyl-1H-pyrazol-1-ium-5-yl)-1-[(3S)-3-phenyl-3-({[(phenylsulfonyl)amino]carbonyl}amino)propyl]piperidinium bis(trifluoroacetate)

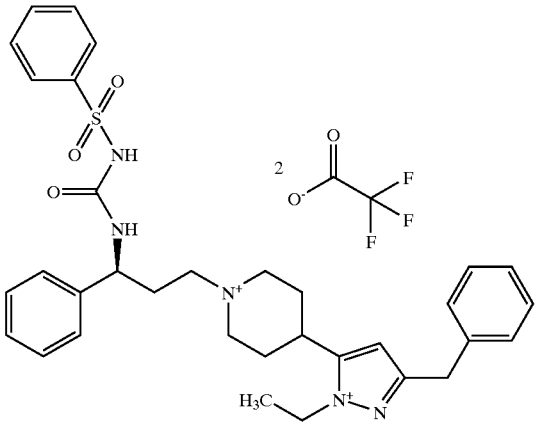

To the a solution of the title amine from Example 1, Step G (0.06 mmol, 31 mg) and DIEA (0.24 mmol, 42 µL) in 1 mL of DCM was added phenylsulfonylisocyanate (0.08 mmol, 15 mg). After 30 min and additional 0.08 mmol of phenylsulfonylisocyanate was added to the reaction. After 1 h the mixture was loaded onto a Varian Bond Elut® SCX ion-exchange cartridge (2 g) and washed with 25 mL of methanol. The product was eluted with 25 mL of 2M ammonia in methanol. The solvent was removed under a stream of nitrogen, and the residue was purified by reverse-phase chromatography. Lyophilization afforded 33 mg of the title compound as a white solid. MS (ESI): ml/z 586 (M+1). HPLC B: 1.69 min.

EXAMPLES 19–66

Automated Synthesis of a One Dimensional Amide Library

To each of a total of 48 dry, 10 mL fritted Myriad reaction vessels under nitrogen was added the amine core (1.0 mL, 0.1 mmoles, 0.1 M in DMSO, containing 4 equiv of dimetnylethylamine). To reaction vessel 1 was then added the appropriate acid subunit (1.0 mL, 0.1 mmoles, 0.1 M in DMSO); this was repeated for the remaining 47 reactions until the acids had been enumerated to all 48 reaction vessels. Finally, to each of the 48 reaction vessels was added the EDC/HOBt cocktail (0.4 mL, 0.1 mmoles, 0.25 M each in deuterated chloroform). The reactions were then aged for 24 hours at room temperature (20–25 C.) with nitrogen sparging agitation (1 s pulse of nitrogen every 20 minutes.) The crude reactions were analyzed by HPLC-MS method 1 (see below.)

All 48 crude reactions were purified by preparative HPLC using UV based detection (Method 2). The collected fractions were then analyzed for purity by LC-MS (Method 3); fractions found to be greater than 90% purity were pooled into tared 40 mL EPA vials and lyophilized.

HPLC Conditions for the Library
Analytical LC Method 1
Column: MetaChem Polaris C-18A, 30 mm×4.6 mm, 5.0 um
Eluent A: 0.1% TFA in Water
Eluent B: 0.1% TFA in Acetonitrile
Gradient: 5% B to 95% B in 3.3 minutes, ramp back to 5% B in 0.3 min
Flow: 2.5 mL/min.
Column Temperature: 50 C.
Injection amount: 5 ul of undiluted crude reaction mixture.
Detection:
    UV at 220 and 254 nm.
    MS: API-ES ionization mode, mass scan range (100–600)
    ELSD: Light Scattering Detector
Preparative LC Method 2
Column: MetaChem Polaris C-18A, 100 mm×21.2 mm, 10 um
Eluent A: 0.1% TFA in Water
Eluent B: 0.1% TFA in Acetonitrile
Pre-inject Equilibration: 1.0 min
Post-Inject Hold: 0.0 min
Gradient: 10% B to 100% B in 6.0 minutes, hold at 100% B for an additional 2.0 minutes, ramp back from 100% B to 10% B in 1.5 minutes.
Flow: 25 ml/min.
Column Temperature: ambient
Injection amount: 1.5 ml of undiluted crude reaction mixture.
Detection: UV at 220 and 254 nm.
Analytical LC Method 3
Column: MetaChem Polaris C-18A, 30 mm×2.0 mm, 3.0 um
Eluent A: 0.1% TFA in Water
Eluent B: 0.1% TFA in Acetonitrile
Gradient: 5% B to 95% B in 2.0 minutes, ramp back to 5% B in 0.1 min
Flow: 1.75 mL/min.
Column Temperature: 60 C.
Injection amount: 5 ul of undiluted fraction.
Detection:
    UV at 220 and 254 nm.
    MS: API-ES ionization mode, mass scan range (100–600)
    ELSD: Light Scattering Detector
The compounds prepared by this method are given in the following Table:

| Example | R | Retention Time (Method 3, min) | Observed Mass by ESI (M + H) |
|---|---|---|---|
| 19 | cyclobutyl-CH2- | 0.987 | 485.43 |
| 20 | N-acetyl-azetidin-3-yl- | 0.877 | 528.6 |
| 21 | cyclopentyl-CH2- | 1.034 | 499.83 |
| 22 | $CH_3-$ | 0.889 | 445.22 |
| 23 | $CH_3CH_2-$ | 0.931 | 459.58 |
| 24 | $(CH_3)_2CH-$ | 0.968 | 473.55 |
| 25 | sec-butyl | 1.003 | 487.53 |
| 26 | cyclopropyl | 0.953 | 471.27 |
| 27 | 2-methylcyclopropyl | 0.999 | 485.4 |
| 28 | 1-methylcyclopropyl | 0.999 | 485.4 |
| 29 | cyclohexyl | 1.071 | 513.56 |
| 30 | tetrahydrofuran-3-yl | 0.914 | 501.4 |
| 31 | tetrahydrofuran-2-yl | 0.941 | 501.54 |
| 32 | tetrahydropyran-4-yl | 0.924 | 515.55 |
| 33 | cyclopropyl-CH2-CH2- | 0.984 | 485.41 |
| 34 | cyclopentyl-CH2-CH2- | 1.067 | 513.5 |
| 35 | cyclohexyl-CH2-CH2- | 1.109 | 527.64 |
| 36 | $CF_3CH_2CH_2-$ | 0.981 | 513.59 |
| 37 | cyclohex-3-en-1-yl | 1.045 | 511.32 |
| 38 | $NC-CH_2-CH_2-$ | 0.915 | 470.44 |
| 39 | $CH_3CH_2-O-CH_2-$ | 0.959 | 489.55 |
| 40 | $CH_3-S-O-CH_2CH_2-$ | 0.966 | 505.34 |
| 41 | $CH_3-SO_2-CH_2CH_2-$ | 0.9 | 523.53 |
| 42 | 2-oxopyrrolidin-4-yl-CH2- | 0.867 | 528.65 |
| 43 | furan-2-yl | 0.967 | 497.26 |
| 44 | furan-3-yl | 0.974 | 497.36 |

-continued

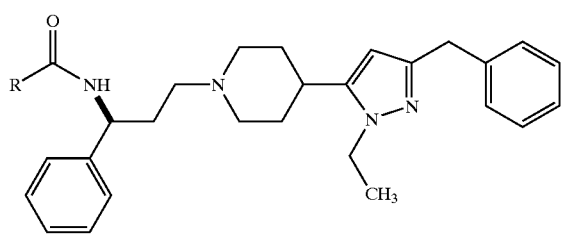

| Example | R | Retention Time (Method 3, min) | Observed Mass by ESI (M + H) |
|---|---|---|---|
| 45 | 2-thienyl | 1.036 | 513.57 |
| 46 | 3-thienyl | 1.004 | 513.44 |
| 47 | 1-methyl-1H-pyrazol-4-yl | 0.922 | 511.54 |
| 48 | 5-methyloxazol-... | 0.908 | 498.59 |
| 49 | 2-methyl-4-ethylthiazol-... | 0.954 | 542.2 |
| 50 | 4-methyl-2-oxoimidazolidin-... | 0.853 | 515.18 |
| 51 | 4-methyl-2-oxothiazolidin-... | 0.907 | 532.28 |
| 52 | (S)-5-oxotetrahydrofuran-... | 0.907 | 515.46 |
| 53 | 4,5,5-trimethyl-2-oxotetrahydrofuran-... | 0.955 | 543.66 |
| 54 | N-propylmaleimide | 0.944 | 554.69 |
| 55 | phenyl | 1.021 | 507.6 |

-continued

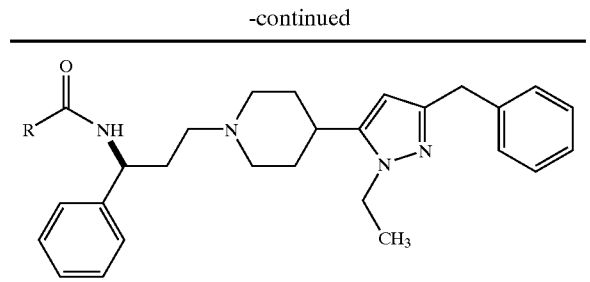

| Example | R | Retention Time (Method 3, min) | Observed Mass by ESI (M + H) |
|---|---|---|---|
| 56 | pyridin-2-yl | 0.991 | 508.58 |
| 57 | pyridin-3-yl | 0.877 | 508.41 |
| 58 | pyridin-4-yl | 0.863 | 508.56 |
| 59 | (S)-3-methyl-2-oxoazetidin-... | 0.873 | 500.5 |
| 60 | cyclopent-2-enyl | 1.045 | 511.38 |
| 61 | 3,4,5-trimethylisoxazol-... | 0.978 | 526.53 |
| 62 | 1-hydroxycyclopropyl | 0.913 | 487.12 |
| 63 | 2,2,4-trimethyltetrahydropyran-... | 0.987 | 543.49 |
| 64 | 2,3-dimethylfuran-... | 1.024 | 511.39 |
| 65 | 3-sulfamoylpropyl | 0.889 | 552.52 |

-continued

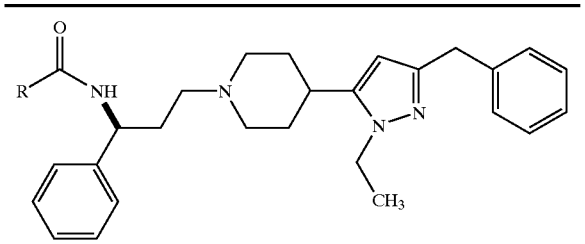

EXAMPLES 67–73

| Example | R | Retention Time (Method 3, min) | Observed Mass by ESI (M + H) |
|---|---|---|---|
| 66 |  | 0.905 | 515.49 |

The following compounds were prepared in accordance with the general procedure set forth in Example 1, Step H.

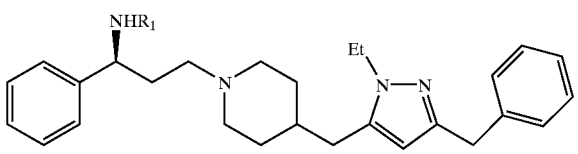

| Example No. | R₁ | MS m/Z (M + 1) | HPLC B (min.) |
|---|---|---|---|
| 67 | 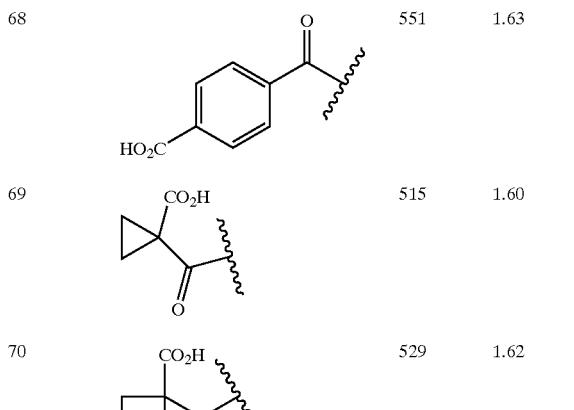 | 551 | 1.63 |
| 68 | | 551 | 1.63 |
| 69 | | 515 | 1.60 |
| 70 | | 529 | 1.62 |

-continued

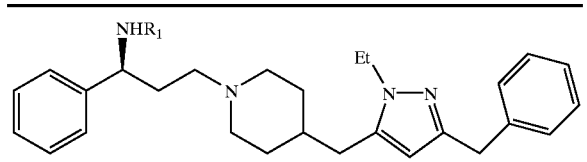

| Example No. | R₁ | MS m/Z (M + 1) | HPLC B (min.) |
|---|---|---|---|
| 71 | 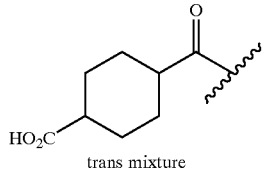 trans mixture | 557 | 1.59 |
| 72 | 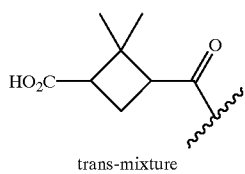 cis/trans mixture | 557 | 1.64 |
| 73 | trans-mixture | 557 | 1.60 |

EXAMPLE 74

N-[1(S)-1-phenyl-3-(4-[3-benzyl-1-ethyl(1H-pyrazol-5-yl)]piperidin-1-yl)propyl]N-acetyl-3-azetadinecarboxamide, bis-TFA salt

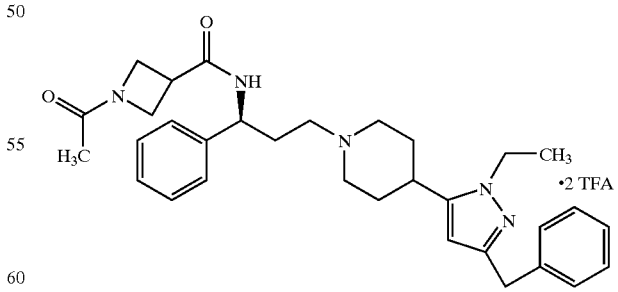

The compound was obtained from the title compound in Example 1, Step G by a procedure analogous to that set forth in Example 1, Step H. MS (ESI): m/z 528 (M+H). HPLC B: 1.25 min.

EXAMPLE 75

N-[1(S)-1-phenyl-3-(4-[3-benzyl-1-ethyl(1H-pyrazol-5-yl)]piperidin-1-yl)propyl]-3-carboxypropylcarboxamide, bis-TFA salt

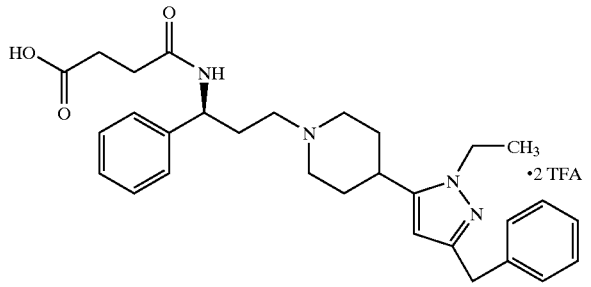

To a solution of the title compound in Example 1, Step G (0.06 mmol, 32 mg) and N,N-diisopropylethylamine (0.4 mmol, 70 μL) in 1 mL of DCM was added succinic anhydride (1 mmol, 100 mg). After 1 h methanol (0.15 mL) was added and the reaction was allowed to stand for 15 h. The solvent was removed under a stream of nitrogen. The residue was taken up in 1:1 dioxane/H$_2$O and purified by reverse-phase chromatography. The product was lyophilized affording the title compound as a white solid. MS (ESI): m/z 503 (M+H). HPLC B: 1.32 min.

EXAMPLES 76–78

The following compounds were prepared according to the general procedure set forth in Example 3.

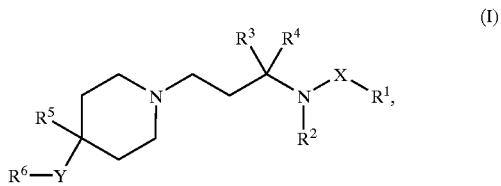

| Example No. | R$^1$ | MS m/Z (M + 1) | HPLC B |
|---|---|---|---|
| 76 | HO$_2$C–(CH$_2$)$_3$–C(O)– | 517 | 1.50 |
| 77 | cyclopentyl(CO$_2$H)(CH$_2$C(O)–) | 571 | 1.73 |
| 78 | cyclohexyl(CO$_2$H)(C(O)–) cis-mixture | 557 | 1.70, 1.77 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of Formula (I):

(I)

wherein "⌇" denotes the point of attachment;

R$^1$ is C$_{1-8}$ alkyl, C$_{2-8}$ alkenyl, C$_{2-8}$ alkynyl, C$_{3-8}$ cycloalkyl, C$_{5-8}$ cycloalkenyl, —O—C$_{3-8}$ cycloalkyl, —NR$^a$R$^b$, phenyl, naphthyl, or heterocycle; wherein any one of which except —NR$^a$R$^b$ is optionally substituted with one or more substituents independently selected from:
 (a) halo,
 (b) cyano,
 (c) —OH,
 (d) C$_{1-6}$ alkyl,
 (e) —O—C$_{1-6}$ alkyl,
 (f) C$_{1-6}$ haloalkyl,
 (g) —O—C$_{1-6}$ haloalkyl,
 (h) C$_{3-6}$ cycloalkyl,
 (i) —O—C$_{3-6}$ cycloalkyl,
 (j) C$_{2-6}$ alkenyl,
 (k) —NO$_2$,
 (l) phenyl, which is optionally substituted with one or more substituents independently selected from C$_{1-4}$ alkyl, —O—C$_{1-4}$ alkyl, halo, and —CO$_2$R$^c$,
 (m) —CO$_2$R$^c$,
 (n) —NR$^c$R$^d$,
 (o) —NR$^c$—COR$^d$,
 (p) —NR$^c$—CO$_2$R$^d$,
 (q) —CO—NR$^c$R$^d$,
 (r) —OCO—NR$^c$R$^d$,
 (s) —NR$^c$CO—NR$^c$R$^d$,
 (t) —S(O)$_p$—R$^c$,
 (u) —S(O)$_2$—NR$^c$R$^d$,
 (v) —NR$^c$S(O)$_2$—R$^d$,
 (w) —NR$^c$S(O)$_2$—NR$^c$R$^d$,
 (x) oxo,
 (y) heterocyclyl, which is optionally substituted with one or more substituents independently selected from C$_{1-4}$ alkyl, —O—C$_{1-4}$ alkyl, halo, —CO$_2$R$^c$, and oxo, (z) —$C_{5-7}$ cycloalkenyl, and
(aa) —C(=O)$R^c$;

X is a direct single bond, —C(=O)—, —C(=O)O—, —$SO_2$—, or —C(=O)N($R^e$)$SO_2$—;

$R^2$ is hydrogen or $C_{1-8}$ alkyl which is optionally substituted with one or more substituents independently selected from halo, —$C_{1-6}$ haloalkyl, —O—$C_{1-6}$ alkyl, —O—$C_{1-6}$ haloalkyl, $C_{3-6}$ cycloalkyl, and —O—$C_{3-6}$ cycloalkyl;

or alternatively $R^1$ and $R^2$ together with the N to which $R^2$ is attached and the X, as defined above, to which $R^1$ is attached, form a 4- to 8-membered monocyclic ring containing from 1 to 3 nitrogen atoms, zero to 2 oxygen atoms, and zero to 2 sulfur atoms; wherein the ring is optionally substituted on one or more ring carbons with one or more substituents independently selected from:
(a) halo,
(b) cyano,
(c) —OH,
(d) $C_{1-6}$ alkyl,
(e) —O—$C_{1-6}$ alkyl,
(f) $C_{1-6}$ haloalkyl, and
(g) —S(O)$_p$—$R^c$;

$R^3$ is hydrogen, —CO—NR$^c$R$^d$, or $C_{1-4}$ alkyl; wherein the alkyl is optionally substituted with one or more substituents independently selected from halo, —OH, —O—$C_{1-4}$ alkyl, or —O—$C_{1-4}$ haloalkyl;

$R^4$ is phenyl, naphthyl, or heterocycle, any one of which is optionally substituted with one or more substituents independently selected from
(a) halo,
(b) —CN,
(c) —OH,
(d) $C_{1-6}$ alkyl,
(e) —O—$C_{1-6}$ alkyl,
(f) $C_{1-6}$ haloalkyl,
(g) —$NO_2$,
(h) phenyl,
(i) —$CO_2R^c$,
(j) —NR$^c$R$^d$,
(k) —NR$^c$—COR$^d$,
(l) —NR$^c$—$CO_2$R$^d$,
(m) —CO—NR$^c$R$^d$,
(n) —OCO—NR$^c$R$^d$,
(o) —NR$^c$CO—NR$^c$R$^d$,
(p) —S(O)$_p$—$R^c$, wherein p is an integer selected from 0, 1 and 2,
(q) —S(O)$_2$—NR$^c$R$^d$,
(r) —NR$^c$S(O)$_2$—R$^d$,
(s) —NR$^c$S(O)$_2$—NR$^c$R$^d$,
(t) $C_{3-6}$ cycloalkyl,
(u) —O—$C_{3-6}$ cycloalkyl,
(v) —O—$C_{1-6}$ haloalkyl,
(w) $C_{2-6}$ alkenyl and
(x) oxo;

$R^5$ is:
(1) hydrogen,
(2) $C_{1-6}$ alkyl, which is optionally substituted with 1–4 substituents independently selected from —OH, cyano, and halo,
(3) cyano,
(4) —OH, or
(5) halo;

Y is:
(1) a direct single bond;
(2) —$C_{1-10}$ alkyl- or —($C_{0-6}$ alkyl)$C_{3-6}$cycloalkyl($C_{0-6}$ alkyl)-, either of which is optionally substituted with 1–7 substituents independently selected from:
(a) halo,
(b) —OH,
(c) —O—$C_{1-3}$ alkyl,
(d) trifluoromethyl,
(e) —($C_{1-3}$ alkyl)hydroxy, and
(f) ethylenedioxy;
(3) —($C_{0-6}$ alkyl)-$Z^1$—($C_{0-6}$ alkyl)-, wherein each alkyl is optionally substituted with 1–7 substituents independently selected from:
(a) halo,
(b) —OH,
(c) —O—$C_{1-3}$ alkyl, and
(d) trifluoromethyl;
and where $Z^1$ is selected from —$SO_2$—, —N($R^f$)—, —N($R^f$)C(=CHR″)N($R^f$)—, —N($R^f$)C(=NR″)N($R^f$)—, —S—, —O—, —SO—, —N($R^f$)$SO_2$—, and —$PO_2$—;
(4) —($C_{0-6}$ alkyl)-$Z^2$—($C_{0-6}$ alkyl)-, wherein each alkyl is optionally substituted with 1–7 substituents independently selected from:
(a) halo,
(b) —OH,
(c) —O—$C_{1-3}$ alkyl, and
(d) trifluoromethyl;
and where $Z^2$ is selected from —C(=O)—, —C(=O)O—, —OC(=O)—, —NR$^g$C(=O)—, and —NR$^g$C(=O)O—;

$R^6$ is phenyl, naphthyl, indanyl, tetrahydronaphthyl, biphenyl, or heterocycle; wherein any one of which is optionally substituted with 1–7 substituents independently selected from:
(a) halo,
(b) cyano,
(c) —OH,
(d) $C_{1-6}$ alkyl, which is unsubstituted or substituted with 1–5 of $R^7$,
(e) —O—$C_{1-6}$ alkyl, which is unsubstituted or substituted with 1–5 of $R^7$,
(f) —O-phenyl, which is unsubstituted or substituted with 1–5 of $R^8$,
(g) —O-heterocycle, which is unsubstituted or substituted with 1–5 of $R^8$,
(h) —$NO_2$,
(i) phenyl,
(j) —$CO_2R^s$,
(k) tetrazolyl,
(l) —NR$^s$R$^t$,
(m) —NR$^s$—COR$^t$,
(n) —NR$^s$—$CO_2$R$^t$,
(o) —CO—NR$^s$R$^t$,
(p) —OCO—NR$^s$R$^t$,
(q) —NR$^s$CO—NR$^s$R$^t$,
(r) —S(O)$_p$—$R^s$,
(s) —S(O)$_2$—NR$^s$R$^t$,
(t) —NR$^s$S(O)$_2$—R$^t$,
(u) —NR$^s$S(O)$_2$—NR$^s$R$^t$,
(v) $C_{2-6}$ alkenyl,
(w) furanyl, which is unsubstituted or substituted with benzyl which is unsubstituted or substituted with 1–7 of $R^8$,
(x) —$C_{3-6}$ cycloalkyl, and
(y) —O—$C_{3-6}$ cycloalkyl;

each $R^7$ is independently halo, cyano, —OH, —O—$C_{1-6}$ alkyl, —$C_{3-6}$ cycloalkyl, —$CO_2$H, —$CO_2$—($C_{1-6}$ alkyl), —$CF_3$, —$SO_2R^s$, —NR$^s$R$^t$, phenyl, naphthyl, biphenyl, or heterocycle; wherein phenyl, naphthyl, biphenyl, or heterocycle is optionally substituted with 1–7 of $R^8$;

each $R^8$ is independently halo, cyano, —OH, $C_{1-6}$ alkyl, $C_{1-6}$ haloalkyl, —O—$C_{1-6}$ alkyl, —O—$C_{1-6}$ haloalkyl, —$CO_2H$, —$CO_2(C_{1-6}$ alkyl), —$NR^sR^t$, —($C_{1-6}$ alkyl)-$NR^sR^t$, —$SO_2R^s$, —$N(R^s)SO_2R^t$, —$N(R^s)COR^t$, —($C_{1-6}$ alkyl)-OH, —O—$C_{3-6}$ cycloalkyl, benzyloxy, phenoxy, or —$NO_2$;

each of $R^a$ and $R^b$ is independently $C_{1-6}$ alkyl which is optionally substituted with one or more substituents independently selected from $C_{3-6}$ cycloalkyl, halo, $CF_3$, —O—$C_{1-6}$ alkyl, and —O—$C_{3-6}$ cycloalkyl;

each $R^c$ is independently hydrogen or $C_{1-4}$ alkyl;

each $R^d$ is independently hydrogen or $C_{1-4}$ alkyl;

$R^e$ is hydrogen or $C_{1-4}$ alkyl;

$R^f$ is hydrogen, $C_{1-6}$ alkyl, $C_{2-6}$ alkenyl, benzyl, phenyl, (CO)$C_{1-6}$ alkyl, —$SO_2$—$C_{1-6}$ alkyl, —$SO_2$-phenyl, —$SO_2$-heterocycle, or $C_{1-6}$ alkyl-$C_{3-6}$ cycloalkyl; wherein any of which except hydrogen is optionally substituted with 1–3 substituents independently selected from halo, $C_{1-3}$ alkyl, —O—$C_{1-3}$ alkyl and trifluoromethyl;

$R^g$ is hydrogen, $C_{1-6}$ alkyl, $C_{2-6}$ alkenyl, $C_{2-6}$ alkynyl, benzyl, phenyl, or $C_{1-6}$ alkyl-$C_{3-6}$ cycloalkyl; wherein any of which except hydrogen is optionally substituted with 1–3 substituents independently selected from halo, $C_{1-3}$ alkyl, —O—$C_{1-3}$ alkyl and trifluoromethyl;

$R^h$ is hydrogen or $C_{1-6}$ alkyl;

each $R^s$ is independently hydrogen, $C_{1-6}$ alkyl, $C_{5-6}$ cycloalkyl, benzyl or phenyl; wherein any of which except hydrogen is optionally substituted with 1–3 substituents independently selected from halo, $C_{1-3}$ alkyl, —O—$C_{1-3}$ alkyl and trifluoromethyl;

each $R^t$ is independently hydrogen, $C_{1-6}$ alkyl, $C_{5-6}$ cycloalkyl, benzyl or phenyl; wherein any of which except hydrogen is optionally substituted with 1–3 substituents independently selected from halo, $C_{1-3}$ alkyl, —O—$C_{1-3}$ alkyl and trifluoromethyl;

$R^u$ is hydrogen, $C_{1-4}$ alkyl, —$NO_2$ or —CN; and each p is independently an integer equal to 0, 1, or 2;

and with the proviso that when Y is a direct single bond, then $R^6$ is phenyl, naphthyl, indanyl, tetrahydronaphthyl, biphenyl, or a heterocycle selected from pyrazolyl and tetrahydropyridopyrazolyl; wherein any one of which is optionally substituted as defined above;

or a pharmaceutically acceptable salt thereof.

2. The compound according to claim 1, wherein $R^1$ is $C_{1-8}$ alkyl, —O—$C_{1-8}$ alkyl, $C_{2-8}$ alkenyl, $C_{2-8}$ alkynyl, $C_{3-8}$ cycloalkyl, $C_{5-8}$ cycloalkenyl, —O—$C_{3-8}$ cycloalkyl, —$NR^aR^b$, phenyl, naphthyl, or a heterocycle selected from:

(i) a 4- to 6-membered saturated heterocycle containing from 1 to 3 heteroatoms selected from nitrogen, oxygen and sulfur, (ii) a 5- to 6-membered heteroaromatic ring containing from 1 to 3 heteroatoms selected from nitrogen, oxygen, and sulfur; and (iii) an 8- to 10-membered bicyclic heterocycle containing from 1 to 4 heteroatoms selected from nitrogen, oxygen and sulfur, either ring of which is saturated or unsaturated;

wherein any one of $R^1$ is optionally substituted with one or more substituents independently selected from:

(a) halo,
(b) cyano,
(c) —OH,
(d) $C_{1-4}$ alkyl,
(e) —O—$C_{1-4}$ alkyl,
(f) $C_{1-4}$ haloalkyl,
(g) —O—$C_{1-4}$ haloalkyl,
(h) —$NO_2$,
(i) phenyl,
(j) —$CO_2R^c$,
(k) —$NR^cR^d$,
(l) —$NR^cCOR^d$,
(m) —$NR^c$—$CO_2R^d$,
(n) —CO—$NR^cR^d$,
(o) —OCO—$NR^cR^d$,
(p) —$NR^cCO$—$NR^cR^d$,
(q) —$S(O)_p$—$R^c$, wherein p is an integer selected from 0, 1 and 2,
(r) —$S(O)_2$—$NR^cR^d$,
(s) —$NR^cS(O)_2$—$R^d$,
(t) —$NR^cS(O)_2$—$NR^cR^d$,
(u) oxo, and
(v) C(=O)$R^c$;

and with the proviso that when Y is a direct single bond, then $R^6$ is phenyl, naphthyl, indanyl, tetrahydronaphthyl, biphenyl, or a heterocycle selected from pyrazolyl and tetrahydropyridopyrazolyl; wherein any one of which is optionally substituted as defined in claim 1;

or a pharmaceutically acceptable salt thereof.

3. The compound according to claim 1, wherein $R^1$ is:

(i) $C_{1-4}$ alkyl which is optionally substituted with a substituent selected from:
 (a) cyano,
 (b) —O—$C_{1-4}$ alkyl,
 (c) —$C_{3-6}$ cycloalkyl,
 (d) —$C_{5-6}$ cycloalkenyl,
 (e) —$CO_2H$,
 (f) —$S(O)_2$—$NR^cR^d$,
 (g) —S—$C_{1-4}$ alkyl, and
 (h) a 5- or 6-membered saturated or unsaturated heterocycle containing from 1 to 3 heteroatoms selected from N, O and S, wherein the heterocycle is optionally substituted with 1 or 2 substituents independently selected from —$C_{1-6}$ alkyl and oxo;

(ii) cycloalkyl selected from cyclopropyl, cyclobutyl, cyclopentyl, and cyclohexyl, which is optionally substituted with from 1 to 3 substituents independently selected from:
 (a) halo,
 (b) —OH,
 (c) cyano,
 (d) $C_{1-6}$ alkyl, and
 (e) —$CO_2H$;

(iii) phenyl which is optionally substituted with from 1 to 3 substituents independently selected from:
 (a) halo,
 (b) cyano,
 (c) $C_{1-6}$ alkyl,
 (d) —O—$C_{1-6}$ alkyl,
 (e) $C_{1-6}$ haloalkyl,
 (f) —O—$C_{1-4}$ haloalkyl, and
 (g) —$CO_2H$;

(iv) a 4- to 6-membered saturated heterocycle selected from the group consisting of azetidinyl, oxacyclobutyl, pyrrolidinyl, tetrahydrofuranyl, 1,3-dioxacyclopentyl, morpholinyl, thiomorpholinyl, thiazolidinyl, oxazolidinyl, isooxazolidinyl, imidazolidinyl, piperazinyl, tetrahydrofuranyl, 1,4-dioxanyl, 1,3- dioxanyl, oxacyclohexyl, piperidinyl, and oxacyclopentyl; wherein the heterocycle is optionally substituted with from 1–3 substituents independently selected from:
(a) halo,
(b) cyano,
(c) $C_{1-6}$ alkyl,
(d) —O—$C_{1-6}$ alkyl,
(e) $C_{1-6}$ haloalkyl,
(f) —O—$C_{1-4}$ haloalkyl,
(g) $C_{3-6}$ cycloalkyl,
(h) —O—$C_{3-6}$ cycloalkyl,
(i) $C_{2-6}$ alkenyl,
(j) phenyl,
(k) oxo, and
(l) —C(=O)$R^c$;
(v) a 5- to 6-membered heteroaromatic selected from the group consisting of thienyl, pyridyl, imidazolyl, pyrrolyl, pyrazolyl, thiazolyl, isothiazolyl, pyrazinyl, pyrimidinyl, triazolyl, tetrazolyl, furanyl, oxazolyl, and isoxazolyl; wherein the heteroaromatic is optionally substituted with from 1–3 substituents independently selected from:
(a) halo,
(b) cyano,
(c) $C_{1-6}$ alkyl,
(d) —O—$C_{1-6}$ alkyl,
(e) $C_{1-6}$ haloalkyl,
(f) —O—$C_{1-4}$ haloalkyl,
(g) $C_{3-6}$ cycloalkyl,
(h) —O—$C_{3-6}$ cycloalkyl,
(i) $C_{2-6}$ alkenyl,
(j) phenyl, and
(k) oxo;
(vi) an 8- to 10-membered bicyclic heterocycle selected from the group consisting of benzimidazolyl, pyridoimidazolyl, indolyl, isoindolyl, phthalazinyl, purinyl, quinoxalinyl, quinazolinyl, cinnolinyl, quinolinyl, isoquinolinyl, indazolyl, dihydroindolyl, dihydroisoindolyl, tetrahydroquinolyl, tetrahydroisoquinolyl, and pyridopyrazolyl; wherein the bicyclic heterocycle is optionally substituted with from 1–3 substituents independently selected from:
(a) halo,
(b) cyano,
(c) $C_{1-6}$ alkyl,
(d) —O—$C_{1-6}$ alkyl,
(e) $C_{1-6}$ haloalkyl,
(f) —O—$C_{1-4}$ haloalkyl,
(g) $C_{3-6}$ cycloalkyl,
(h) —O—$C_{3-6}$ cycloalkyl,
(i) $C_{2-6}$ alkenyl,
(j) phenyl, and
(k) oxo;
and with the proviso that when Y is a direct single bond, then $R^6$ is phenyl, naphthyl, indanyl, tetrahydronaphthyl, biphenyl, or a heterocycle selected from pyrazolyl and tetrahydropyridopyrazolyl; wherein any one of which is optionally substituted as defined in claim 1;
or a pharmaceutically acceptable salt thereof.

4. The compound according to claim 1, wherein $R^2$ is hydrogen or $C_{1-6}$ alkyl which is optionally substituted with one or more substituents independently selected from fluoro, —$CF_3$, —O—$C_{1-4}$ alkyl, $C_{3-6}$ cycloalkyl, and —O—$C_{3-6}$ cycloalkyl;
and with the proviso that when Y is a direct single bond, then $R^6$ is phenyl, naphthyl, indanyl, tetrahydronaphthyl, biphenyl, or a heterocycle selected from pyrazolyl and tetrahydropyridopyrazolyl; wherein any one of which is optionally substituted as defined in claim 1;
or a pharmaceutically acceptable salt thereof.

5. The compound according to claim 1, wherein $R^3$ is hydrogen;
and with the proviso that when Y is a direct single bond, then $R^6$ is phenyl, naphthyl, indanyl, tetrahydronaphthyl, biphenyl, or a heterocycle selected from pyrazolyl and tetrahydropyridopyrazolyl; wherein any one of which is optionally substituted as defined in claim 1;
or a pharmaceutically acceptable salt thereof.

6. The compound according to claim 1, wherein $R^4$ is phenyl or heterocycle, wherein the phenyl or heterocycle is optionally substituted with from 1 to 4 substituents independently selected from
(a) halo,
(b) —CN,
(c) —OH,
(d) $C_{1-4}$ alkyl,
(e) —O—$C_{1-4}$ alkyl,
(f) $CF_3$,
(g) —$NO_2$,
(h) phenyl,
(i) —$CO_2R^c$,
(j) —$NR^cR^d$,
(k) —$NR^c$—$COR^d$,
(l) —$NR^c$—$CO_2R^d$,
(m) —CO—$NR^cR^d$,
(n) —OCO—$NR^cR^d$,
(o) —$NR^c$CO—$NR^cR^d$,
(p) —$S(O)_p$—$R^c$,
(q) —$S(O)_2$—$NR^cR^d$,
(r) —$NR^cS(O)_2$—$R^d$,
(s) —$NR^cS(O)_2$—$NR^cR^d$,
(t) $C_{3-6}$ cycloalkyl, and
(u) —O—$C_{3-6}$ cycloalkyl;
and with the proviso that when Y is a direct single bond, then $R^6$ is phenyl, naphthyl, indanyl, tetrahydronaphthyl, biphenyl, or a heterocycle selected from pyrazolyl and tetrahydropyridopyrazolyl; wherein any one of which is optionally substituted as defined in claim 1;
or a pharmaceutically acceptable salt thereof.

7. The compound according to claim 1, wherein $R^5$ is hydrogen or fluoro;
and with the proviso that when Y is a direct single bond, then $R^6$ is phenyl, naphthyl, indanyl, tetrahydronaphthyl, biphenyl, or a heterocycle selected from pyrazolyl and tetrahydropyridopyrazolyl; wherein any one of which is optionally substituted as defined in claim 1;
or a pharmaceutically acceptable salt thereof.

8. The compound according to claim 1, wherein $R^5$ is hydrogen;
and with the proviso that when Y is a direct single bond, then $R^6$ is phenyl, naphthyl, indanyl, tetrahydronaphthyl, biphenyl, or a heterocycle selected from pyrazolyl and tetrahydropyridopyrazolyl; wherein any one of which is optionally substituted as defined in claim 1;

or a pharmaceutically acceptable salt thereof.

9. The compound according to claim 1, wherein Y is
(1) a direct single bond;
(2) —$C_{1-6}$ alkyl-, which is optionally substituted with 1–7 substituents independently selected from:
 (a) halo,
 (b) —OH,
 (c) —O—$C_{1-3}$ alkyl, and
 (d) trifluoromethyl;
(3) —($C_{0-2}$ alkyl)-$Z^1$—($C_{0-2}$ alkyl)-, wherein the alkyl is unsubstituted;
 $Z^1$ is selected from —$SO_2$—, —SO—, —N($R^f$)—, —S—, and —O—;
 and $R^f$ is $C_{1-4}$ alkyl, $C_{2-5}$ alkenyl, or $C_{1-3}$ alkyl-$C_{3-6}$ cycloalkyl; or
(4) —($C_{0-2}$ alkyl)-$Z^2$—($C_{0-2}$ alkyl)-, wherein the alkyl is optionally substituted with 1–4 substituents independently selected from:
 (a) halo,
 (b) —OH,
 (c) —O—$C_{1-3}$ alkyl, and
 (d) trifluoromethyl;
 and wherein
 $Z^2$ is selected from —$NR^gC$(=O)—, and —$NR^gC$(=O)O—;
 $R^g$ is hydrogen, $C_{1-6}$ alkyl, $C_{2-6}$ alkenyl, $C_{2-6}$ alkynyl, benzyl, phenyl, or $C_{1-6}$ alkyl-$C_{3-6}$ cycloalkyl; wherein any of which except hydrogen is optionally substituted with from 1 to 3 substituents independently selected from halo, $C_{1-3}$ alkyl, —O—$C_{1-3}$ alkyl and trifluoromethyl; and
 $R^h$ is —H or $C_{1-6}$ alkyl;
and with the proviso that when Y is a direct single bond, then $R^6$ is phenyl, naphthyl, indanyl, tetrahydronaphthyl, biphenyl, or a heterocycle selected from pyrazolyl and tetrahydropyridopyrazolyl; wherein any one of which is optionally substituted as defined in claim 1;
or a pharmaceutically acceptable salt thereof.

10. The compound according to claim 1, wherein Y is
(1) a direct single bond;
(2) —$C_{2-4}$ alkyl-, which is optionally substituted with 1–6 substituents independently selected from:
 (a) halo,
 (b) —O—$C_{1-3}$ alkyl, and
 (c) trifluoromethyl;
(3) selected from
 —($C_{0-2}$ alkyl)-$SO_2$—($C_{0-2}$ alkyl)-,
 —($C_{0-2}$ alkyl)-SO—($C_{0-2}$ alkyl)-,
 —($C_{0-2}$ alkyl)-S—($C_{0-2}$ alkyl)-,
 —($C_{0-2}$ alkyl)-O—($C_{0-2}$ alkyl)-, and
 —($C_{0-2}$ alkyl)-N($R^f$)—($C_{0-2}$ alkyl)-; and
 where $R^f$ is $C_{2-4}$ alkyl, $C_{2-3}$ alkenyl or $C_{1-2}$ alkyl-$C_3$ cycloalkyl;
(4) —($C_{0-2}$ alkyl)-$Z^2$—($C_{0-2}$ alkyl)-, wherein the alkyl is not substituted; and where
 $Z^2$ is selected from —$NR^gC$(=O)—, and —$NR^gC$(=O)O—;
 $R^g$ is hydrogen, $C_{1-3}$ alkyl, $C_{2-3}$ alkenyl, or $C_{2-3}$ alkynyl; and
 $R^h$ is —H or $C_{1-4}$ alkyl;
and with the proviso that when Y is a direct single bond, then $R^6$ is phenyl, naphthyl, indanyl, tetrahydronaphthyl, biphenyl, or a heterocycle selected from pyrazolyl and tetrahydropyridopyrazolyl; wherein any one of which is optionally substituted as defined in claim 1;

or a pharmaceutically acceptable salt thereof.

11. The compound according to claim 1, wherein Y is
(1) a direct single bond;
(2) $C_{2-4}$ alkyl, which is optionally substituted with from 1 to 6 fluoros; or
(3) selected from:
 (a) —$SO_2CH_2CH_2$—,
 (b) —SO—$CH_2CH_2$—,
 (c) —$SCH_2CH_2$—,
 (d) —$CH_2$—O—$CH_2$—,
 (e) —N($CH_2CH_3$)—,
 (f) —N($CH_2CH_2CH_3$)—, and
 (g) —N($CH_2$-cyclopropyl)-,
and with the proviso that when Y is a direct single bond, then $R^6$ is phenyl, naphthyl, indanyl, tetrahydronaphthyl, biphenyl, or a heterocycle selected from pyrazolyl and tetrahydropyridopyrazolyl; wherein any one of which is optionally substituted as defined in claim 1;
or a pharmaceutically acceptable salt thereof.

12. The compound according to claim 1, wherein Y is a direct single bond;
and $R^6$ is phenyl, naphthyl, indanyl, tetrahydronaphthyl, biphenyl, or a heterocycle selected from pyrazolyl and tetrahydropyridopyrazolyl; wherein any one of which is optionally substituted as defined in claim 1;
or a pharmaceutically acceptable salt thereof.

13. The compound according to claim 1, wherein $R^6$ is phenyl, benzoimidazolyl, imidazolyl, pyridoimidazolyl, isoxazolyl, oxazolyl, pyrazolyl, pyridyl, thiazolyl, imidazothiophenyl, indazolyl, tetrahydropyridoimidazolyl, tetrahydroindazolyl, dihydrothiopyranopyrazolyl, dihydrodioxothiopyranopyrazolyl, dihydropyranopyrazolyl, tetrahydropyridopyrazolyl, or triazolyl; wherein any of which is optionally substituted with from 1 to 7 substituents independently selected from:
(a) halo,
(b) cyano,
(c) —OH,
(d) $C_{1-6}$ alkyl, which is unsubstituted or substituted with 1–5 of $R^7$
(e) —O—$C_{1-6}$ alkyl, which is unsubstituted or substituted with 1–5 of $R^7$,
(f) —$NO_2$,
(g) phenyl,
(h) —$CO_2R^s$,
(i) tetrazolyl,
(j) —$NR^sR^t$,
(k) —$NR^s$—$COR^t$,
(l) —$NR^s$—$CO_2R^t$,
(m) —CO—$NR^sR^t$,
(n) —OCO—$NR^sR^t$,
(o) —$NR^sCO$—$NR^sR^t$,
(p) —$S(O)_p$—$R^s$,
(q) —$S(O)_2$—$NR^sR^t$,
(r) —$NR^sS(O)_2$—$R^t$,
(s) —$NR^sS(O)_2$—$NR^sR^t$,
(t) —$C_{3-5}$ cycloalkyl, and
(t) —O—$C_{3-5}$ cycloalkyl;
 each $R^7$ is independently halo, cyano, —OH, —O—$C_{1-6}$ alkyl, —$C_{3-5}$ cycloalkyl, —$CO_2H$, —$CO_2(C_{1-6}$ alkyl), —$CF_3$, —$SO_2R^s$, —$NR^sR^t$, phenyl, naphthyl, biphenyl, or heterocycle; wherein phenyl, naphthyl, biphenyl, or heterocycle is optionally substituted with 1–7 of $R^8$;

each $R^8$ is independently halo, cyano, —OH, $C_{1-4}$ alkyl, —O—$C_{1-4}$ alkyl, —O—$C_{3-5}$ cycloalkyl, —$CO_2H$, —$CO_2(C_{1-6}$ alkyl), —$CF_3$, —$OCF_3$, —$SO_2R^a$, —$N(R^a)SO_2R^b$, or —$NR^sR^t$;

each $R^s$ is independently hydrogen, $C_{1-6}$ alkyl, $C_{5-6}$ cycloalkyl, benzyl or phenyl, wherein any of which except hydrogen is optionally substituted with 1–3 substituents independently selected from halo, $C_{1-3}$ alkyl, —O—$C_{1-3}$ alkyl, $C_{1-3}$ fluoroalkyl, and —O—$C_{1-3}$ fluoroalkyl; and each $R^t$ is independently hydrogen, $C_{1-6}$ alkyl, $C_{5-6}$ cycloalkyl, benzyl or phenyl, wherein any of which except hydrogen is optionally substituted with 1–3 substituents independently selected from halo, $C_{1-3}$ alkyl, —O—$C_{1-3}$ alkyl, $C_{1-3}$ fluoroalkyl, and —O—$C_{1-3}$ fluoroalkyl;

and with the proviso that when Y is a direct single bond, then $R^6$ is phenyl or a heterocycle selected from pyrazolyl and tetrahydropyridopyrazolyl; wherein the phenyl or heterocycle is optionally substituted as defined above;

or a pharmaceutically acceptable salt thereof.

14. The compound according to claim 1, wherein $R^6$ is benzimidazolyl, imidazolyl, pyridoimidazolyl, isoxazolyl, oxazolyl, pyrazolyl, pyridyl, thiazolyl, imidazothiophenyl, indazolyl, tetrahydropyridoimidazolyl, tetrahydroindazolyl, dihydrothiopyranopyrazolyl, dihydrodioxothiopyranopyrazolyl, dihydropyranopyrazolyl, tetrahydropyridopyrazolyl, or triazolyl; wherein any of which is optionally substituted with from 1 to 5 substituents independently selected from:

(a) halo,
(b) cyano,
(c) —$NO_2$,
(d) —$CF_3$,
(e) —$CHF_2$,
(f) —$CH_2F$,
(g) —$CH_2OH$,
(h) —$CH_2OCH_3$,
(i) —$(CH_2)_{1-2}SO_2$—$(C_{1-2}$ alkyl)
(j) phenyl,
(k) $C_{1-6}$ alkyl, which is optionally substituted with phenyl, which is optionally substituted with from 1 to 4 substituents independently selected from halo, cyano, —OH, —O—$C_{1-6}$ alkyl, —O—$C_{3-5}$ cycloalkyl, —$CO_2H$, —$CO_2(C_{1-6}$ alkyl), —$CF_3$, —$OCF_3$, and —$SO_2$—$(C_{1-3}$ alkyl);
(l) —O—$C_{1-6}$ alkyl,
(m) —$C_{3-5}$ cycloalkyl,
(n) —$CH_2$—$(C_{3-5}$ cycloalkyl), and
(o) —O—$C_{3-5}$ cycloalkyl;

and with the proviso that when Y is a direct single bond, then $R^6$ is pyrazolyl or tetrahydropyridopyrazolyl, either of which is optionally substituted as defined above;

or a pharmaceutically acceptable salt thereof.

15. The compound according to claim 1, wherein Q is

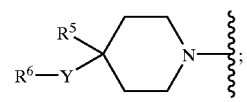

and with the proviso that when Y is a direct single bond, then $R^6$ is phenyl, naphthyl, indanyl, tetrahydronaphthyl, biphenyl, or a heterocycle selected from pyrazolyl and tetrahydropyridopyrazolyl; wherein any one of which is optionally substituted as defined in claim 1;

or a pharmaceutically acceptable salt thereof.

16. The compound according to claim 1, wherein Q is

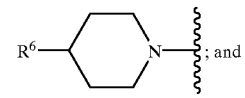

; and $R^6$ is phenyl, naphthyl, indanyl, tetrahydronaphthyl, biphenyl, or a heterocycle selected from pyrazolyl and tetrahydropyridopyrazolyl; wherein any one of which is optionally substituted as defined in claim 1;

or a pharmaceutically acceptable salt thereof.

17. The compound according to claim 1, which is a compound of Formula (II):

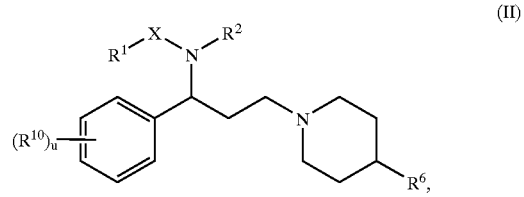

(II)

wherein
X is —C(=O)— or —$SO_2$—;
$R^1$ is $C_{1-4}$ alkyl or is:

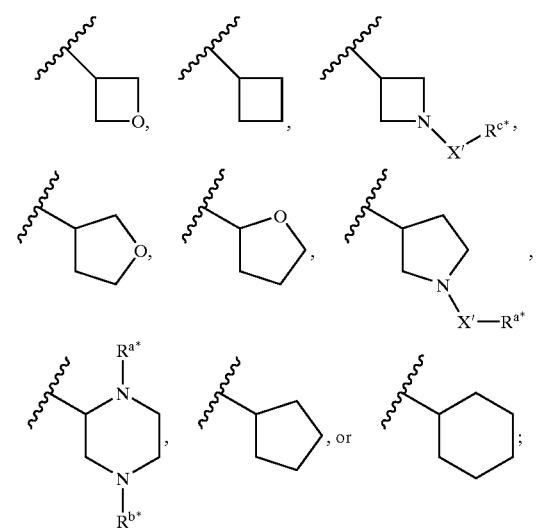

wherein
X' independently has the same definition as X;
each of $R^{a*}$ and $R^{b*}$ is independently $C_{1-6}$ alkyl which is optionally substituted with one or more substituents independently selected from $C_{3-6}$ cycloalkyl, halo, $CF_3$, —O—$C_{1-6}$ alkyl, and —O—$C_{3-6}$ cycloalkyl;

$R^{c*}$ is hydrogen or $C_{1-4}$ alkyl;

$R^2$ is hydrogen or $C_{1-8}$ alkyl;

$R^3$ is hydrogen;

$R^6$ is

[chemical structures of pyrazole groups with $R^{12}$, $R^{14}$, $R^{16}$ substituents, and a bicyclic pyrazole with $(R^{18})_v$]

each $R^{10}$ is independently $C_{1-4}$ alkyl, —O—$C_{1-4}$ alkyl, —$CF_3$, —$OCF_3$, —OH, —CN, or halo;

$R^{12}$ is —H, $C_{1-4}$ alkyl, or —$CH_2$-phenyl wherein the phenyl is optionally substituted with 1 or 2 substituents independently selected from chloro, fluoro, —CN, —$C_{1-3}$ alkyl, —O—$C_{1-3}$ alkyl, —O—cyclopropyl, —O—cyclobutyl, —$CF_3$, —$OCF_3$, —$SO_2$—($C_{1-3}$ alkyl), and —N(H)$SO_2$—($C_{1-3}$ alkyl);

each of $R^{14}$ and $R^{16}$ is independently —H, $C_{1-4}$ alkyl, —O—$C_{1-4}$ alkyl, $CF_3$, —OH, —CN, halo, or —$CH_2$-phenyl wherein the phenyl is optionally substituted with 1 or 2 substituents independently selected from chloro, fluoro, —CN, —$C_{1-3}$ alkyl, —O—$C_{1-3}$ alkyl, —O—cyclopropyl, —O—cyclobutyl, —$CF_3$, —$OCF_3$, —$SO_2$—($C_{1-3}$ alkyl), and —N(H)$SO_2$—($C_{1-3}$ alkyl);

each $R^{18}$ is independently $C_{1-4}$ alkyl, —O—$C_{1-4}$ alkyl, —$CF_3$, —$OCF_3$, —OH, —CN, or halo;

u is an integer from zero to 4; and v is an integer from zero to 3;

or a pharmaceutically acceptable salt thereof.

18. The compound according to claim 17, which is a compound of Formula (II):

[chemical structure of Formula (II)]

(II)

wherein

X is —C(=O)— or —$SO_2$—;

$R^1$ is:

[chemical structures: oxetane, cyclobutyl, azetidine with $X'$—$R^{c*}$, tetrahydrofuran, tetrahydrofuran, pyrrolidine with $X'$—$R^{a*}$, or piperazine with $R^{a*}$ and $R^{b*}$]

wherein $X'$ independently has the same definition as X;

each of $R^{a*}$ and $R^{b*}$ is independently $C_{1-6}$ alkyl which is optionally substituted with one or more substituents independently selected from $C_{3-6}$ cycloalkyl, halo, $CF_3$, —O—$C_{1-6}$ alkyl, and —O—$C_{3-6}$ cycloalkyl;

$R^{c*}$ is hydrogen or $C_{1-4}$ alkyl;

$R^2$ is hydrogen or $C_{1-8}$ alkyl;

$R^3$ is hydrogen;

$R^6$ is

[chemical structures of pyrazole groups with $R^{12}$, $R^{14}$, $R^{16}$ substituents, and a bicyclic pyrazole with $(R^{18})_v$]

each $R^{10}$ is independently $C_{1-4}$ alkyl, —O—$C_{1-4}$ alkyl, —$CF_3$, —$OCF_3$, —OH, —CN, or halo;

$R^{12}$ is —H, $C_{1-4}$ alkyl, or —$CH_2$-phenyl wherein the phenyl is optionally substituted with 1 or 2 substituents independently selected from chloro, fluoro, —CN, —$C_{1-3}$ alkyl, —O—$C_{1-3}$ alkyl, —O—cyclopropyl, —O—cyclobutyl, —$CF_3$, —$OCF_3$, —$SO_2$—($C_{1-3}$ alkyl), and —N(H)$SO_2$—($C_{1-3}$ alkyl);

each of $R^{14}$ and $R^{16}$ is independently —H, $C_{1-4}$ alkyl, —O—$C_{1-4}$ alkyl, $CF_3$, —OH, —CN, halo, or —$CH_2$-phenyl wherein the phenyl is optionally substituted with 1 or 2 substituents independently selected from chloro, fluoro, —CN, —$C_{1-3}$ alkyl, —O—$C_{1-3}$ alkyl, —O—cyclopropyl, —O—cyclobutyl, —CF$_3$, —OCF$_3$, —SO$_2$—(C$_{1-3}$ alkyl), and —N(H)SO$_2$—(C$_{1-3}$ alkyl);

each R$^{18}$ is independently C$_{1-4}$ alkyl, —O—C$_{1-4}$ alkyl, —CF$_3$, —OCF$_3$, —OH, —CN, or halo;

u is an integer from zero to 4; and v is an integer from zero to 3;

or a pharmaceutically acceptable salt thereof.

19. The compound according to claim 17, which is a compound of Formula (III):

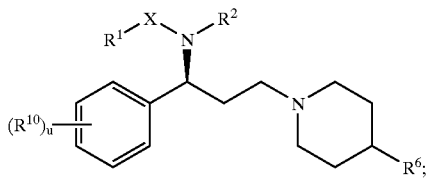

(III)

or a pharmaceutically acceptable salt thereof.

20. The compound according to claim 1, which is a compound selected from the group consisting of:

N-[1(S)-1-phenyl-3-(4-[3-benzyl-1-ethyl(1H-pyrazol-5-yl)]piperidin-1-yl)propyl]cyclobutanecarboxamide;

N-[1(S)-1-phenyl-3-(4-[3-benzyl-1-ethyl(1H-pyrazol-5-yl)]piperidin-1-yl)propyl]N-acetyl-3-azetadinecarboxamide;

N-[1(S)-1-phenyl-3-(4-[3-benzyl-1-ethyl(1H-pyrazol-5-yl)]piperidin-1-yl)propyl]-3-carboxypropylcarboxamide;

N-[1(S)-1-phenyl-3-(4-[3-benzyl-1-ethyl(1H-pyrazol-5-yl)]piperidin-1-yl)propyl]methylsulfonamide;

N-{(1S)-3-[4-(3-benzyl-1-ethyl-1H-pyrazol-5-yl)piperidin-1-yl]-1-phenylpropyl}ethanesulfonamide;

N-{(1S)-3-[4-(3-benzyl-1-ethyl-1H-pyrazol-5-yl)piperidin-1-yl]-1-phenylpropyl}thiophene-2-sulfonamide;

2(+/−)-(N-[1(S)-1-phenyl-3-(4-[3-benzyl-1-ethyl(1H-pyrazol-5-yl)]piperidin-1-yl)propyl]amino)butanoic acid;

N-{(1S)-3-[4-(3-benzyl-1-ethyl-1H-pyrazol-5-yl)piperidin-1-yl]-1-phenylpropyl}isoleucine;

({(1S)-3-[4-(3-benzyl-1-ethyl-1H-pyrazol-5-yl)piperidin-1-yl]-1-phenylpropyl}amino)(2-furyl)acetic acid;

3-[1-({(1S)-3-[4-(3-benzyl-1-ethyl-1H-pyrazol-5-yl)piperidin-1-yl]-1-phenylpropyl}amino)ethyl]benzoic acid;

N-[1(S)-1-phenyl-3-(4-[2-ethyl-4,5,6,7-tetrahydropyrazolo(1,5-α)pyridin-3-yl]piperidin-1-yl)propyl]cyclobutanecarboxamide;

N-[1(S)-1-phenyl-3-(4-[3-ethyl-1-(4-[ethylsulfonyl]benzyl)-(1H-pyrazol-5-yl)-piperidin-1-yl)propyl]cyclobutanecarboxamide;

N-[1(S)-1-phenyl-3-(4-[1,3-diethyl-5-methyl(1H-pyrazol-4-yl]piperidin-1-yl)propyl]cyclobutanecarboxamide;

N-[1(S)-1-(3-fluorophenyl)-3-(4-[2-ethyl-4,5,6,7-tetrahydropyrazolo(1,5-α)pyridin-3-yl]piperidin-1-yl)propyl]cyclobutanecarboxamide;

N-[1(S)-1-(3-fluorophenyl)-3-(4-[3-benzyl-1-ethyl(1H-pyrazol-5-yl]piperidin-1-yl)propyl]cyclobutanecarboxamide;

N-[1(S)-1-(3-fluorophenyl)-3-(4-[1,3-diethyl-5-methyl(1H-pyrazol-4-yl]piperidin-1-yl)propyl]cyclobutanecarboxamide;

and pharmaceutically acceptable salts thereof.

21. A pharmaceutical composition which comprises an effective amount of a compound according to claim 1 or a pharmaceutically acceptable salt thereof and a pharmaceutically acceptable carrier.

22. A method for modulating chemokine CCR5 receptor activity in a subject which comprises administering to the subject an effective amount of the compound according to claim 1 or a pharmaceutically acceptable salt thereof.

23. A method for preventing infection by HIV, treating infection by HIV, delaying of the onset of AIDS, or treating AIDS in a patient, which comprises administering to the patient of an effective amount of the compound according to claim 1 or a pharmaceutically acceptable salt thereof.

24. A compound of formula:

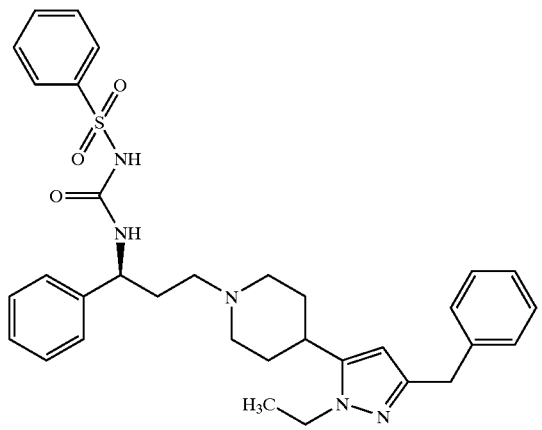

or a pharmaceutically acceptable salt thereof.

* * * * *